(12) United States Patent
Nelles

(10) Patent No.: US 12,152,239 B2
(45) Date of Patent: Nov. 26, 2024

(54) RNA EDITING VIA RECRUITMENT OF SPLICEOSOME COMPONENTS

(71) Applicant: Tacit Therapeutics, Inc., South San Francisco, CA (US)

(72) Inventor: David A. Nelles, San Francisco, CA (US)

(73) Assignee: Tacit Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 18/362,698

(22) Filed: Jul. 31, 2023

(65) Prior Publication Data

US 2024/0011026 A1  Jan. 11, 2024

Related U.S. Application Data

(63) Continuation of application No. PCT/US2022/042486, filed on Sep. 2, 2022.

(60) Provisional application No. 63/345,660, filed on May 25, 2022, provisional application No. 63/240,428, filed on Sep. 3, 2021.

(51) Int. Cl.
C12N 15/11 (2006.01)

(52) U.S. Cl.
CPC ........ *C12N 15/111* (2013.01); *C12N 2320/33* (2013.01)

(58) Field of Classification Search
CPC . C12N 15/113; C12N 15/111; C12N 2320/33; C12N 2310/3519; C12N 15/11; C12N 2799/021
See application file for complete search history.

(56) References Cited

U.S. PATENT DOCUMENTS

| | | | |
|---|---|---|---|
| 5,994,124 A | 11/1999 | Bozzoni | |
| 8,735,366 B2 | 5/2014 | Bauer et al. | |
| 9,074,207 B2 | 7/2015 | Pagani et al. | |
| 9,217,147 B2 | 12/2015 | Singh et al. | |
| 9,303,078 B2 | 4/2016 | Garcia et al. | |
| 9,655,979 B2 | 5/2017 | Bauer et al. | |
| 10,987,433 B2 | 4/2021 | Bennett et al. | |
| 11,230,707 B2 | 1/2022 | Flanigan et al. | |
| 2002/0193580 A1 | 12/2002 | Mitchell et al. | |
| 2011/0301218 A1* | 12/2011 | Bozzoni | A61P 21/00 435/348 |
| 2013/0072541 A1 | 3/2013 | Garcia | |
| 2013/0210902 A1* | 8/2013 | Pagani | A61P 43/00 435/375 |
| 2014/0350089 A1 | 11/2014 | Selden et al. | |
| 2017/0145394 A1 | 5/2017 | Yeo et al. | |
| 2018/0028664 A1 | 2/2018 | Besin et al. | |
| 2019/0111072 A1 | 4/2019 | Patzel et al. | |
| 2019/0207890 A1 | 7/2019 | Hsu et al. | |
| 2020/0148745 A1 | 5/2020 | Keravala et al. | |
| 2020/0239863 A1 | 7/2020 | Yeo et al. | |
| 2021/0071178 A1 | 3/2021 | Borrajo | |
| 2021/0155938 A1 | 5/2021 | Johnson et al. | |
| 2021/0388351 A1 | 12/2021 | Cheng et al. | |

FOREIGN PATENT DOCUMENTS

| | | |
|---|---|---|
| WO | WO-2017099823 A1 | 6/2017 |
| WO | WO-2018161032 A1 | 9/2018 |
| WO | WO-2019204514 A1 | 10/2019 |
| WO | WO-2020051555 A1 | 3/2020 |
| WO | WO-2020160486 A1 | 8/2020 |
| WO | WO-2020205604 A1 | 10/2020 |
| WO | WO-2020214973 A1 | 10/2020 |
| WO | WO-2021076656 A1 | 4/2021 |
| WO | WO-2021216853 A1 | 10/2021 |
| WO | WO-2021242903 A2 | 12/2021 |
| WO | WO-2022067228 A1 | 3/2022 |
| WO | WO-2023034582 A1 | 3/2023 |

OTHER PUBLICATIONS

O'Reilly et al., Differentially expressed, variant U1 snRNAs regulate gene expression in human cells, Genome Research, vol. 23, pp. 281-291. (Year: 2013).*
Koller et al., Trans-splicing improvement by the combined application of antisense strategies, International Journal of Molecular Sciences, vol. 16, pp. 1179-1191. (Year: 2015).*
Coady et al., Development of a single vector system that enhances trans-splicing of SMN2 transcripts, PLoS ONE, vol. 3(10): 33468, pp. 1-11. (Year: 2008).*
Goyenvalle et al., "Enhanced exon-skipping induced by U7 snRNA carrying a splicing silencer sequence: Promising tool for DMD therapy," Mol Ther (2009) 17(7):1234-1240.
Huttner et al., "Designing Efficient Double RNA trans-Splicing Molecules for Targeted RNA Repair," Int J Mol Sci (2016) 17(10):1609, 20 pages.
Pinotti et al., "U1-snRNA-mediated rescue of mRNA processing in severe factor VII deficiency," Blood (2008) 111(5):2681-2684.
Rogalska et al., "Therapeutic activity of modified U1 core spliceosomal particles," Nat Commun (2016) 7:11168, 13 pages.
Song et al., "Functional cystic fibrosis transmembrane conductance regulator expression in cystic fibrosis airway epithelial cells by AAV6.2-mediated segmental trans-splicing," Hum Gene Ther (2009) 20(3):267-281.
Durand et al. The Inside Out of Lentiviral Vectors. Viruses 2011, 3, 132-159.
Kwon et al. Specific Regression of Human Cancer Cells by Ribozyme-Mediated Targeted Replacement of Tumor-Specific Transcript. Molecular Therapy, vol. 12, No. 5, Nov. 2005. pp. 824-834.
Lai et al. Efficient in vivo gene expression by trans-splicing adeno-associated viral vectors. Nat. Biotechnol. Nov. 2005; 23(11): pp. 1435-1439.

(Continued)

Primary Examiner — Dana H Shin
(74) Attorney, Agent, or Firm — MORRISON & FOERSTER LLP

(57) ABSTRACT

Disclosed are methods and compositions for promoting trans-splicing. In some embodiments, the composition comprises an engineered small nuclear RNA that promotes trans-splicing of a target RNA molecule. The composition may further comprise an RNA donor molecule.

13 Claims, 10 Drawing Sheets

Specification includes a Sequence Listing.

(56) References Cited

OTHER PUBLICATIONS

PCT/US2021/052315 International Search Report and Written Opinion dated Mar. 4, 2022.
PCT/US2022/042486 International Search Report and Written Opinion dated Dec. 8, 2022.
Prondzynski et al. Evaluation of MYBPC3 trans-Splicing and Gene Replacement as Therapeutic Options in Human iPSC-Derived Cardiomyocytes. Molecular Therapy—Nucleic Acids, vol. 7, Jun. 2017. pp. 475-486.
Shi et al. SUMOylation of DDX39A Alters Binding and Export of Antiviral Transcripts to Control Innate Immunity. The Journal of Immunology, 2020, 205: pp. 168-180.

* cited by examiner

Spliceosome recruitment to edit internal RNA sequences

Stabilized trans-splicing molecule for 5' terminal trans-splicing

SEQUENCE LISTING

```
Sequence total quantity: 97
SEQ ID NO: 1                    moltype = RNA   length = 10
FEATURE                         Location/Qualifiers
source                          1..10
                                mol_type = other RNA
                                organism = synthetic construct
SEQUENCE: 1
cgagctctct                                                                    10

SEQ ID NO: 2                    moltype = RNA   length = 10
FEATURE                         Location/Qualifiers
source                          1..10
                                mol_type = other RNA
                                organism = synthetic construct
SEQUENCE: 2
aacgagctct                                                                    10

SEQ ID NO: 3                    moltype = RNA   length = 10
FEATURE                         Location/Qualifiers
source                          1..10
                                mol_type = other RNA
                                organism = synthetic construct
SEQUENCE: 3
cgcaacgagc                                                                    10

SEQ ID NO: 4                    moltype = RNA   length = 10
FEATURE                         Location/Qualifiers
source                          1..10
                                mol_type = other RNA
                                organism = synthetic construct
SEQUENCE: 4
tatcgcaacg                                                                    10

SEQ ID NO: 5                    moltype = RNA   length = 10
FEATURE                         Location/Qualifiers
source                          1..10
                                mol_type = other RNA
                                organism = synthetic construct
SEQUENCE: 5
aataatatcg                                                                    10

SEQ ID NO: 6                    moltype = RNA   length = 10
FEATURE                         Location/Qualifiers
source                          1..10
                                mol_type = other RNA
                                organism = synthetic construct
SEQUENCE: 6
taagagagct                                                                    10

SEQ ID NO: 7                    moltype = RNA   length = 10
FEATURE                         Location/Qualifiers
source                          1..10
                                mol_type = other RNA
                                organism = synthetic construct
SEQUENCE: 7
aagagagctc                                                                    10

SEQ ID NO: 8                    moltype = RNA   length = 14
FEATURE                         Location/Qualifiers
source                          1..14
                                mol_type = other RNA
                                organism = synthetic construct
SEQUENCE: 8
agagagctcg ttgc                                                               14

SEQ ID NO: 9                    moltype = RNA   length = 10
FEATURE                         Location/Qualifiers
source                          1..10
                                mol_type = other RNA
                                organism = synthetic construct
SEQUENCE: 9
gagagctcgt                                                                    10

SEQ ID NO: 10                   moltype = RNA   length = 14
FEATURE                         Location/Qualifiers
source                          1..14
                                mol_type = other RNA
                                organism = synthetic construct
```

```
SEQUENCE: 10
agagctcgtt gcga                                                                    14

SEQ ID NO: 11          moltype = RNA   length = 10
FEATURE                Location/Qualifiers
source                 1..10
                       mol_type = other RNA
                       organism = synthetic construct
SEQUENCE: 11
gagctcgttg                                                                         10

SEQ ID NO: 12          moltype = RNA   length = 10
FEATURE                Location/Qualifiers
source                 1..10
                       mol_type = other RNA
                       organism = synthetic construct
SEQUENCE: 12
cgagctctct                                                                         10

SEQ ID NO: 13          moltype = RNA   length = 10
FEATURE                Location/Qualifiers
source                 1..10
                       mol_type = other RNA
                       organism = synthetic construct
SEQUENCE: 13
aacgagctct                                                                         10

SEQ ID NO: 14          moltype = RNA   length = 10
FEATURE                Location/Qualifiers
source                 1..10
                       mol_type = other RNA
                       organism = synthetic construct
SEQUENCE: 14
tatcgcaacg                                                                         10

SEQ ID NO: 15          moltype = RNA   length = 10
FEATURE                Location/Qualifiers
source                 1..10
                       mol_type = other RNA
                       organism = synthetic construct
SEQUENCE: 15
aataatatcg                                                                         10

SEQ ID NO: 16          moltype = RNA   length = 10
FEATURE                Location/Qualifiers
source                 1..10
                       mol_type = other RNA
                       organism = synthetic construct
SEQUENCE: 16
taagagagct                                                                         10

SEQ ID NO: 17          moltype = RNA   length = 10
FEATURE                Location/Qualifiers
source                 1..10
                       mol_type = other RNA
                       organism = synthetic construct
SEQUENCE: 17
aagagagctc                                                                         10

SEQ ID NO: 18          moltype = RNA   length = 14
FEATURE                Location/Qualifiers
source                 1..14
                       mol_type = other RNA
                       organism = synthetic construct
SEQUENCE: 18
agagagctcg ttgc                                                                    14

SEQ ID NO: 19          moltype = RNA   length = 10
FEATURE                Location/Qualifiers
source                 1..10
                       mol_type = other RNA
                       organism = synthetic construct
SEQUENCE: 19
gagagctcgt                                                                         10

SEQ ID NO: 20          moltype = RNA   length = 14
FEATURE                Location/Qualifiers
source                 1..14
                       mol_type = other RNA
```

```
                            organism = synthetic construct
SEQUENCE: 20
agagctcgtt gcga                                                           14

SEQ ID NO: 21           moltype = RNA   length = 10
FEATURE                 Location/Qualifiers
source                  1..10
                        mol_type = other RNA
                        organism = synthetic construct
SEQUENCE: 21
gagctcgttg                                                                10

SEQ ID NO: 22           moltype = RNA   length = 161
FEATURE                 Location/Qualifiers
source                  1..161
                        mol_type = other RNA
                        organism = synthetic construct
SEQUENCE: 22
cgagctctct gcaggggaaa gcgcgaacgc agtaccacta ccacaaatta tgcaatcgag         60
tttcccacat ttggggaaat cgcaggggtc aacacatctg gagtgcaatg gataagcctc        120
gccctgggaa aaccaccttc gtgatcatgt tatctcccct g                            161

SEQ ID NO: 23           moltype = RNA   length = 163
FEATURE                 Location/Qualifiers
source                  1..163
                        mol_type = other RNA
                        organism = synthetic construct
SEQUENCE: 23
cgagctctct gtccagggga aagcacaaac agttccccac tgccacaaat tatgtagtcg         60
agattccctc atttggggaa atcacagggg tcagcacatc cagagtaaaa ttgctaagcc        120
ttgccctgga aaaaccacct tcgtgatcat aacatttctt ctg                          163

SEQ ID NO: 24           moltype = RNA   length = 163
FEATURE                 Location/Qualifiers
source                  1..163
                        mol_type = other RNA
                        organism = synthetic construct
SEQUENCE: 24
cgagctctct gcagggaaaa acacagacac agttccccac tgccacaaat tatgtaatca         60
agattcccac attcggggaa atcacagggg tcagcacatc cacagtaaaa ctgctaagcc        120
ttgctctgga aaaaccacct tcgtgatcat aacatttctt ctg                          163

SEQ ID NO: 25           moltype = RNA   length = 163
FEATURE                 Location/Qualifiers
source                  1..163
                        mol_type = other RNA
                        organism = synthetic construct
SEQUENCE: 25
cgagctctct gcaggggaaa gcgcggacgc agtcccccac taccacaaat tatgcagtcg         60
agtttcccac atttggggaa atcgcagggg tcagcacatc cggagtgcaa tggataagcc        120
tcgccctggg aaaaccacct tcgtgatcat ggtatctccc ctg                          163

SEQ ID NO: 26           moltype = RNA   length = 163
FEATURE                 Location/Qualifiers
source                  1..163
                        mol_type = other RNA
                        organism = synthetic construct
SEQUENCE: 26
cgagctctct gggggaaaaa gagcgaacgc agtctcccac taccacaaat tatgcagtcg         60
agcttcccac atttgggaa gttgcacgaa ttagcttcgc cctgcgaaaa ccaccttcgt        120
aaacacgatt tttcttctgc taggtaaatg tgagtctgca cgc                          163

SEQ ID NO: 27           moltype = RNA   length = 163
FEATURE                 Location/Qualifiers
source                  1..163
                        mol_type = other RNA
                        organism = synthetic construct
SEQUENCE: 27
cgagctctct gcagaggaca gcgcgaacgc agtcccccac taccacaaat tatgcagtcg         60
agtttcccac atttggggaa acggcagggg tcagcacatc cggagtgcaa tggataagcc        120
tctccctggg aaaaccacct tcgtgatcat cgtatctccc ctg                          163

SEQ ID NO: 28           moltype = RNA   length = 167
FEATURE                 Location/Qualifiers
source                  1..167
                        mol_type = other RNA
                        organism = synthetic construct
SEQUENCE: 28
cgagctctct gcagaggaaa gcgcgaacgc agtcccccac taccacaaat tatgcaatcg         60
```

```
agtttcccac gtttggggaa atcgcagagg tcagcacatc cggaacacaa tggataaccc    120
tcgccctgag aaaaaccacc ttcgtttaga taatagtatc tcccctg                   167

SEQ ID NO: 29          moltype = RNA   length = 164
FEATURE                Location/Qualifiers
source                 1..164
                       mol_type = other RNA
                       organism = synthetic construct
SEQUENCE: 29
cgagctctct gcaagagaaa gcgcgaacgt agttccctac tatcacaaat tatgcactcg    60
agtttcccac acttggggaa atcgcagggg tcagcacatc ggaacgcaa tggataagct     120
tcgccctgag aaaaaccacc ttcgtgatca tggtatctcc cctt                     164

SEQ ID NO: 30          moltype = RNA   length = 164
FEATURE                Location/Qualifiers
source                 1..164
                       mol_type = other RNA
                       organism = synthetic construct
SEQUENCE: 30
cgagctctct gcaggggaaa gcgcgaacgc agtccctac tatcacaagt tatgcagtcg     60
agttcctcac attggggaa aatggcaggg gtcagtacac ccggaacata acggataagc     120
ctcgccctga gaaaaccacc ttcgtgatca tggtatctcc cccg                     164

SEQ ID NO: 31          moltype = RNA   length = 164
FEATURE                Location/Qualifiers
source                 1..164
                       mol_type = other RNA
                       organism = synthetic construct
SEQUENCE: 31
cgagctctct gcaggggaaa acgcgaacac agtccctac tatcacaagt tatgcagtcg     60
agttcctcac attggggaa aatggcaggg gtcagtacac ccggaacata acggataagc     120
ctcgccctga gaaaaccacc ttcgtgatca tggtatctcc cccg                     164

SEQ ID NO: 32          moltype = RNA   length = 163
FEATURE                Location/Qualifiers
source                 1..163
                       mol_type = other RNA
                       organism = synthetic construct
SEQUENCE: 32
cgagctctct gcaggggaga tagtatgatc atgaaagtgg ttttttccaga gcgaggctta    60
tccattgcac tccggatgtg ttgacctctg cgatttcccc aactgtggga aactcgactg    120
cgtaatttgt ggtagtgggg gactgcgttc gcgctttccc ctg                      163

SEQ ID NO: 33          moltype = RNA   length = 166
FEATURE                Location/Qualifiers
source                 1..166
                       mol_type = other RNA
                       organism = synthetic construct
SEQUENCE: 33
cgagctctct gcaggggaga tactattatc aaacgaaggt ggttttttctc agggcgaggc   60
ttatccattg tgttccggat gtgctgacct ctgcgatttc cccaaacgtg ggaaactcga    120
ctgcataatt tgtggtagtg ggggactgcg ttcgcgcttt cctctg                   166

SEQ ID NO: 34          moltype = RNA   length = 163
FEATURE                Location/Qualifiers
source                 1..163
                       mol_type = other RNA
                       organism = synthetic construct
SEQUENCE: 34
cgagctctct gcagaagaaa tgttatgatc acgaaggtgg ttttttccaga gcaaggctta    60
gcagttttac tgtggatgtg ctgaccctg tgatttcccc gaatgtggga atcttgatta     120
cataatttgt ggcagtgggg aactgtgtct gtgttttccc ctg                      163

SEQ ID NO: 35          moltype = RNA   length = 163
FEATURE                Location/Qualifiers
source                 1..163
                       mol_type = other RNA
                       organism = synthetic construct
SEQUENCE: 35
cgagctctct gcaggggaaa gcgcgaacgc agtaccacta ccacaacagg gcgaggctta    60
tccattgcac tccggatgtg ctgacccctg cgatttcccc aaatgtggga aactcgactg    120
cataatttgt ggtagtgggg gactgcgttc gcgctttccc ctg                      163

SEQ ID NO: 36          moltype = RNA   length = 163
FEATURE                Location/Qualifiers
source                 1..163
                       mol_type = other RNA
                       organism = synthetic construct
SEQUENCE: 36
```

```
cgagctctct gcagggggga aagcacaaac agttccccac tgccaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163
```

SEQ ID NO: 37          moltype = RNA   length = 163
FEATURE                 Location/Qualifiers
source                  1..163
                        mol_type = other RNA
                        organism = synthetic construct
SEQUENCE: 37

```
cgagctctct gcagggaaaa acacagacac agttccccac tgccaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163
```

SEQ ID NO: 38          moltype = RNA   length = 163
FEATURE                 Location/Qualifiers
source                  1..163
                        mol_type = other RNA
                        organism = synthetic construct
SEQUENCE: 38

```
cgagctctct gcagggaaa gcgcggacgc agtcccccac taccaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163
```

SEQ ID NO: 39          moltype = RNA   length = 163
FEATURE                 Location/Qualifiers
source                  1..163
                        mol_type = other RNA
                        organism = synthetic construct
SEQUENCE: 39

```
cgagctctct gcagggaaaa gagcgaacgc agtctcccac taccaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163
```

SEQ ID NO: 40          moltype = RNA   length = 163
FEATURE                 Location/Qualifiers
source                  1..163
                        mol_type = other RNA
                        organism = synthetic construct
SEQUENCE: 40

```
cgagctctct gcaggggaca gcgcgaacgc agtcccccac taccaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163
```

SEQ ID NO: 41          moltype = RNA   length = 163
FEATURE                 Location/Qualifiers
source                  1..163
                        mol_type = other RNA
                        organism = synthetic construct
SEQUENCE: 41

```
cgagctctct gcaggggaaa gcgcgaacgc agtcccccac taccaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163
```

SEQ ID NO: 42          moltype = RNA   length = 163
FEATURE                 Location/Qualifiers
source                  1..163
                        mol_type = other RNA
                        organism = synthetic construct
SEQUENCE: 42

```
cgagctctct gcaggggaaa gcgcgaacgt agttccctac tatcaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163
```

SEQ ID NO: 43          moltype = RNA   length = 163
FEATURE                 Location/Qualifiers
source                  1..163
                        mol_type = other RNA
                        organism = synthetic construct
SEQUENCE: 43

```
cgagctctct gcaggggaaa gcgcgaacgc agtccctac tatcaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163
```

SEQ ID NO: 44          moltype = RNA   length = 163
FEATURE                 Location/Qualifiers
source                  1..163
                        mol_type = other RNA
                        organism = synthetic construct

```
SEQUENCE: 44
cgagctctct gcaggggaaa acgcgaacac agtcccctac tatcaccagg gcgaggctta    60
tccattgcac tccggatgtg ctgacccctg cgatttcccc aaatgtggga aactcgactg   120
cataatttgt ggtagtgggg gactgcgttc gcgctttccc ctg                     163

SEQ ID NO: 45           moltype = RNA   length = 163
FEATURE                 Location/Qualifiers
source                  1..163
                        mol_type = other RNA
                        organism = synthetic construct
SEQUENCE: 45
cgagctctct gcaggggaga tagtatgatc atgaaagtgg ttttttccagg gcgaggctta   60
tccattgcac tccggatgtg ctgacccctg cgatttcccc aaatgtggga aactcgactg   120
cataatttgt ggtagtgggg gactgcgttc gcgctttccc ctg                     163

SEQ ID NO: 46           moltype = RNA   length = 163
FEATURE                 Location/Qualifiers
source                  1..163
                        mol_type = other RNA
                        organism = synthetic construct
SEQUENCE: 46
cgagctctct gcaggggaga tactattatc aaacgaaggt ggttttcagg gcgaggctta    60
tccattgcac tccggatgtg ctgacccctg cgatttcccc aaatgtggga aactcgactg   120
cataatttgt ggtagtgggg gactgcgttc gcgctttccc ctg                     163

SEQ ID NO: 47           moltype = RNA   length = 163
FEATURE                 Location/Qualifiers
source                  1..163
                        mol_type = other RNA
                        organism = synthetic construct
SEQUENCE: 47
cgagctctct gcaggggaaa tgttatgatc acgaaggtgg ttttttccagg gcgaggctta   60
tccattgcac tccggatgtg ctgacccctg cgatttcccc aaatgtggga aactcgactg   120
cataatttgt ggtagtgggg gactgcgttc gcgctttccc ctg                     163

SEQ ID NO: 48           moltype = RNA   length = 163
FEATURE                 Location/Qualifiers
source                  1..163
                        mol_type = other RNA
                        organism = synthetic construct
SEQUENCE: 48
cgagctctct gcaggggaga taccatgatc acgaaggtgg ttttccatta tgcaatcgag    60
tttcccacat ttgggaaaat cgcagggggtc cgatttcccc aaatgtggga aactcgactg  120
cataatttgt ggtagtgggg gactgcgttc gcgctttccc ctg                     163

SEQ ID NO: 49           moltype = RNA   length = 163
FEATURE                 Location/Qualifiers
source                  1..163
                        mol_type = other RNA
                        organism = synthetic construct
SEQUENCE: 49
cgagctctct gcaggggaga taccatgatc acgaaggtgg ttttccaaat tatgtagtcg    60
agattccctc atttgggaa atcacagggg cgatttcccc aaatgtggga aactcgactg   120
cataatttgt ggtagtgggg gactgcgttc gcgctttccc ctg                     163

SEQ ID NO: 50           moltype = RNA   length = 163
FEATURE                 Location/Qualifiers
source                  1..163
                        mol_type = other RNA
                        organism = synthetic construct
SEQUENCE: 50
cgagctctct gcaggggaga taccatgatc acgaaggtgg ttttccaaat tatgtaatca    60
agattcccac attcggggaa atcacagggg cgatttcccc aaatgtggga aactcgactg   120
cataatttgt ggtagtgggg gactgcgttc gcgctttccc ctg                     163

SEQ ID NO: 51           moltype = RNA   length = 163
FEATURE                 Location/Qualifiers
source                  1..163
                        mol_type = other RNA
                        organism = synthetic construct
SEQUENCE: 51
cgagctctct gcaggggaga taccatgatc acgaaggtgg ttttccaaat tatgcagtcg    60
agtttcccac atttggggaa atcgcagggg cgatttcccc aaatgtggga aactcgactg   120
cataatttgt ggtagtgggg gactgcgttc gcgctttccc ctg                     163

SEQ ID NO: 52           moltype = RNA   length = 163
FEATURE                 Location/Qualifiers
source                  1..163
                        mol_type = other RNA
```

```
                        organism = synthetic construct
SEQUENCE: 52
cgagctctct gcaggggaga taccatgatc acgaaggtgg ttttccaaat tatgcagtcg    60
agcttcccac atttgggaa gttgcacgaa cgatttcccc aaatgtggga aactcgactg   120
cataatttgt ggtagtgggg gactgcgttc gcgctttccc ctg                    163

SEQ ID NO: 53            moltype = RNA   length = 163
FEATURE                  Location/Qualifiers
source                   1..163
                         mol_type = other RNA
                         organism = synthetic construct
SEQUENCE: 53
cgagctctct gcaggggaga taccatgatc acgaaggtgg ttttccaaat tatgcaatcg    60
agtttcccac gtttgggaa atcgcagagg cgatttcccc aaatgtggga aactcgactg   120
cataatttgt ggtagtgggg gactgcgttc gcgctttccc ctg                    163

SEQ ID NO: 54            moltype = RNA   length = 163
FEATURE                  Location/Qualifiers
source                   1..163
                         mol_type = other RNA
                         organism = synthetic construct
SEQUENCE: 54
cgagctctct gcaggggaga taccatgatc acgaaggtgg ttttccaaat tatgcactcg    60
agtttcccac acttgggaa atcgcagggg cgatttcccc aaatgtggga aactcgactg   120
cataatttgt ggtagtgggg gactgcgttc gcgctttccc ctg                    163

SEQ ID NO: 55            moltype = RNA   length = 163
FEATURE                  Location/Qualifiers
source                   1..163
                         mol_type = other RNA
                         organism = synthetic construct
SEQUENCE: 55
cgagctctct gcaggggaga taccatgatc acgaaggtgg ttttccaagt tatgcagtcg    60
agttcctcac attgggggaa aatggcaggg cgatttcccc aaatgtggga aactcgactg   120
cataatttgt ggtagtgggg gactgcgttc gcgctttccc ctg                    163

SEQ ID NO: 56            moltype = RNA   length = 163
FEATURE                  Location/Qualifiers
source                   1..163
                         mol_type = other RNA
                         organism = synthetic construct
SEQUENCE: 56
cgagctctct gcaggggaga taccatgatc acgaaggtgg ttttcccaga gcgaggctta    60
tccattgcac tccggatgtg ttgacctctg cgatttcccc aaatgtggga aactcgactg   120
cataatttgt ggtagtgggg gactgcgttc gcgctttccc ctg                    163

SEQ ID NO: 57            moltype = RNA   length = 163
FEATURE                  Location/Qualifiers
source                   1..163
                         mol_type = other RNA
                         organism = synthetic construct
SEQUENCE: 57
cgagctctct gcaggggaga taccatgatc acgaaggtgg ttttcctctc agggcgaggc    60
ttatccattg tgttccggat gtgctgacct cgatttcccc aaatgtggga aactcgactg   120
cataatttgt ggtagtgggg gactgcgttc gcgctttccc ctg                    163

SEQ ID NO: 58            moltype = RNA   length = 163
FEATURE                  Location/Qualifiers
source                   1..163
                         mol_type = other RNA
                         organism = synthetic construct
SEQUENCE: 58
cgagctctct gcaggggaga taccatgatc acgaaggtgg ttttcccaga gcaaggctta    60
gcagttttac tgtggatgtg ctgacccctg cgatttcccc aaatgtggga aactcgactg   120
cataatttgt ggtagtgggg gactgcgttc gcgctttccc ctg                    163

SEQ ID NO: 59            moltype = RNA   length = 163
FEATURE                  Location/Qualifiers
source                   1..163
                         mol_type = other RNA
                         organism = synthetic construct
SEQUENCE: 59
cgagctctct gcaggggaga taccatgatc acgaaggtgg ttttcccagg gcgaggctta    60
tccattgcac tccggatgtg ctgacccctg aacacatctg gagtgcaatg gataagactg   120
cataatttgt ggtagtgggg gactgcgttc gcgctttccc ctg                    163

SEQ ID NO: 60            moltype = RNA   length = 163
FEATURE                  Location/Qualifiers
source                   1..163
```

```
                            mol_type = other RNA
                            organism = synthetic construct
SEQUENCE: 60
cgagctctct gcaggggaga taccatgatc acgaaggtgg ttttcccagg gcgaggctta    60
tccattgcac tccggatgtg ctgacccctg tcagcacatc cagagtaaaa ttgctaactg    120
cataatttgt ggtagtgggg gactgcgttc gcgctttccc ctg                      163

SEQ ID NO: 61               moltype = RNA    length = 163
FEATURE                     Location/Qualifiers
source                      1..163
                            mol_type = other RNA
                            organism = synthetic construct
SEQUENCE: 61
cgagctctct gcaggggaga taccatgatc acgaaggtgg ttttcccagg gcgaggctta    60
tccattgcac tccggatgtg ctgacccctg tcagcacatc cggagtgcaa tggataactg    120
cataatttgt ggtagtgggg gactgcgttc gcgctttccc ctg                      163

SEQ ID NO: 62               moltype = RNA    length = 163
FEATURE                     Location/Qualifiers
source                      1..163
                            mol_type = other RNA
                            organism = synthetic construct
SEQUENCE: 62
cgagctctct gcaggggaga taccatgatc acgaaggtgg ttttcccagg gcgaggctta    60
tccattgcac tccggatgtg ctgacccctg ttagcttcgc cctgcgaaaa ccacctactg    120
cataatttgt ggtagtgggg gactgcgttc gcgctttccc ctg                      163

SEQ ID NO: 63               moltype = RNA    length = 163
FEATURE                     Location/Qualifiers
source                      1..163
                            mol_type = other RNA
                            organism = synthetic construct
SEQUENCE: 63
cgagctctct gcaggggaga taccatgatc acgaaggtgg ttttcccagg gcgaggctta    60
tccattgcac tccggatgtg ctgacccctg tcagcacatc cggaacacaa tggataactg    120
cataatttgt ggtagtgggg gactgcgttc gcgctttccc ctg                      163

SEQ ID NO: 64               moltype = RNA    length = 163
FEATURE                     Location/Qualifiers
source                      1..163
                            mol_type = other RNA
                            organism = synthetic construct
SEQUENCE: 64
cgagctctct gcaggggaga taccatgatc acgaaggtgg ttttcccagg gcgaggctta    60
tccattgcac tccggatgtg ctgacccctg tcagcacatc cggaacgcaa tggataactg    120
cataatttgt ggtagtgggg gactgcgttc gcgctttccc ctg                      163

SEQ ID NO: 65               moltype = RNA    length = 163
FEATURE                     Location/Qualifiers
source                      1..163
                            mol_type = other RNA
                            organism = synthetic construct
SEQUENCE: 65
cgagctctct gcaggggaga taccatgatc acgaaggtgg ttttcccagg gcgaggctta    60
tccattgcac tccggatgtg ctgacccctg gtcagtacac ccggaacata acggatactg    120
cataatttgt ggtagtgggg gactgcgttc gcgctttccc ctg                      163

SEQ ID NO: 66               moltype = RNA    length = 163
FEATURE                     Location/Qualifiers
source                      1..163
                            mol_type = other RNA
                            organism = synthetic construct
SEQUENCE: 66
cgagctctct gcaggggaga taccatgatc acgaaggtgg ttttcccagg gcgaggctta    60
tccattgcac tccggatgtg ctgacccctg cgatttcccc aactgtggga aactcgactg    120
cataatttgt ggtagtgggg gactgcgttc gcgctttccc ctg                      163

SEQ ID NO: 67               moltype = RNA    length = 163
FEATURE                     Location/Qualifiers
source                      1..163
                            mol_type = other RNA
                            organism = synthetic construct
SEQUENCE: 67
cgagctctct gcaggggaga taccatgatc acgaaggtgg ttttcccagg gcgaggctta    60
tccattgcac tccggatgtg ctgacccctg ctgcgatttc cccaaacgtg ggaaacactg    120
cataatttgt ggtagtgggg gactgcgttc gcgctttccc ctg                      163

SEQ ID NO: 68               moltype = RNA    length = 161
FEATURE                     Location/Qualifiers
```

```
source                         1..161
                               mol_type = other RNA
                               organism = synthetic construct
SEQUENCE: 68
cgagctctct gcaggggaga taccatgatc acgaaggtgg ttttcccagg gcgaggctta    60
tccattgcac tccggatgtg ctgacccctg cgatttcccc aaatgtggga aactcgactg   120
cataatttgt ggtagtcttc gtgatcatgt tatctcccct g                       161

SEQ ID NO: 69                  moltype = RNA   length = 163
FEATURE                        Location/Qualifiers
source                         1..163
                               mol_type = other RNA
                               organism = synthetic construct
SEQUENCE: 69
cgagctctct gcaggggaga taccatgatc acgaaggtgg ttttcccagg gcgaggctta    60
tccattgcac tccggatgtg ctgacccctg cgatttcccc aaatgtggga aactcgactg   120
cataatttgt ggtagtacct tcgtgatcat aacatttctt ctg                     163

SEQ ID NO: 70                  moltype = RNA   length = 163
FEATURE                        Location/Qualifiers
source                         1..163
                               mol_type = other RNA
                               organism = synthetic construct
SEQUENCE: 70
cgagctctct gcaggggaga taccatgatc acgaaggtgg ttttcccagg gcgaggctta    60
tccattgcac tccggatgtg ctgacccctg cgatttcccc aaatgtggga aactcgactg   120
cataatttgt ggtagtacct tcgtgatcat ggtatctccc ctg                     163

SEQ ID NO: 71                  moltype = RNA   length = 373
FEATURE                        Location/Qualifiers
source                         1..373
                               mol_type = other RNA
                               organism = synthetic construct
SEQUENCE: 71
gctctcttac gcaggggaga taccatgatc acgaaggtgg ttttcccagg gcgaggctta    60
tccattgcac tccggatgtg ctgacccctg cgatttcccc aaatgtggga aactcgactg   120
cataatttgt ggtagtgggg gactgcgttc gcgctttccc ctgactttct ggagtttcaa   180
aagtagactg tacgctaagg gtcatatctt tttttgtttt ggtttgtgtc ttggttggcg   240
tcttaaatgt taatcctaca gtggagggct gcggaatagg aagtaacatg tcgcctgcac   300
gccataggag aaaaagcgag catcagccgt atcggctttg taacacaaat tagctatcgt   360
gaagtccgct cag                                                      373

SEQ ID NO: 72                  moltype = RNA   length = 373
FEATURE                        Location/Qualifiers
source                         1..373
                               mol_type = other RNA
                               organism = synthetic construct
SEQUENCE: 72
cgagctctct gcaggggaga taccatgatc acgaaggtgg ttttcccagg gcgaggctta    60
tccattgcac tccggatgtg ctgacccctg cgatttcccc aaatgtggga aactcgactg   120
cataatttgt ggtagtgggg gactgcgttc gcgctttccc ctgactttct ggagtttcaa   180
aagtagactg tacgctaagg gtcatatctt tttttgtttt ggtttgtgtc ttggttggcg   240
tcttaaatgt taatcctaca gtggagggct gcggaatagg aagtaacatg tcgcctgcac   300
gccataggag aaaaagcgag catcagccgt atcggctttg taacacaaat tagctatcgt   360
gaagtccgct cag                                                      373

SEQ ID NO: 73                  moltype = RNA   length = 373
FEATURE                        Location/Qualifiers
source                         1..373
                               mol_type = other RNA
                               organism = synthetic construct
SEQUENCE: 73
aacgagctct gcaggggaga taccatgatc acgaaggtgg ttttcccagg gcgaggctta    60
tccattgcac tccggatgtg ctgacccctg cgatttcccc aaatgtggga aactcgactg   120
cataatttgt ggtagtgggg gactgcgttc gcgctttccc ctgactttct ggagtttcaa   180
aagtagactg tacgctaagg gtcatatctt tttttgtttt ggtttgtgtc ttggttggcg   240
tcttaaatgt taatcctaca gtggagggct gcggaatagg aagtaacatg tcgcctgcac   300
gccataggag aaaaagcgag catcagccgt atcggctttg taacacaaat tagctatcgt   360
gaagtccgct cag                                                      373

SEQ ID NO: 74                  moltype = RNA   length = 373
FEATURE                        Location/Qualifiers
source                         1..373
                               mol_type = other RNA
                               organism = synthetic construct
SEQUENCE: 74
cgcaacgagc gcaggggaga taccatgatc acgaaggtgg ttttcccagg gcgaggctta    60
tccattgcac tccggatgtg ctgacccctg cgatttcccc aaatgtggga aactcgactg   120
cataatttgt ggtagtgggg gactgcgttc gcgctttccc ctgactttct ggagtttcaa   180
```

```
aagtagactg tacgctaagg gtcatatctt tttttgtttt ggtttgtgtc ttggttggcg    240
tcttaaatgt taatcctaca gtggagggct gcggaatagg aagtaacatg tcgcctgcac    300
gccataggag aaaaagcgag catcagccgt atcggctttg taacacaaat tagctatcgt    360
gaagtccgct cag                                                      373

SEQ ID NO: 75           moltype = RNA    length = 373
FEATURE                 Location/Qualifiers
source                  1..373
                        mol_type = other RNA
                        organism = synthetic construct
SEQUENCE: 75
tatcgcaacg gcaggggaga taccatgatc acgaaggtgg ttttcccagg gcgaggctta    60
tccattgcac tccggatgtg ctgacccctg cgatttcccc aaatgtggga aactcgactg    120
cataatttgt ggtagtgggg gactgcgttc gcgctttccc ctgactttct ggagtttcaa    180
aagtagactg tacgctaagg gtcatatctt tttttgtttt ggtttgtgtc ttggttggcg    240
tcttaaatgt taatcctaca gtggagggct gcggaatagg aagtaacatg tcgcctgcac    300
gccataggag aaaaagcgag catcagccgt atcggctttg taacacaaat tagctatcgt    360
gaagtccgct cag                                                      373

SEQ ID NO: 76           moltype = RNA    length = 373
FEATURE                 Location/Qualifiers
source                  1..373
                        mol_type = other RNA
                        organism = synthetic construct
SEQUENCE: 76
aataatatcg gcaggggaga taccatgatc acgaaggtgg ttttcccagg gcgaggctta    60
tccattgcac tccggatgtg ctgacccctg cgatttcccc aaatgtggga aactcgactg    120
cataatttgt ggtagtgggg gactgcgttc gcgctttccc ctgactttct ggagtttcaa    180
aagtagactg tacgctaagg gtcatatctt tttttgtttt ggtttgtgtc ttggttggcg    240
tcttaaatgt taatcctaca gtggagggct gcggaatagg aagtaacatg tcgcctgcac    300
gccataggag aaaaagcgag catcagccgt atcggctttg taacacaaat tagctatcgt    360
gaagtccgct cag                                                      373

SEQ ID NO: 77           moltype = RNA    length = 374
FEATURE                 Location/Qualifiers
source                  1..374
                        mol_type = other RNA
                        organism = synthetic construct
SEQUENCE: 77
atctctctta cctcggggag ataccatgat cacgaaggtg gttttcccag ggcgaggctt    60
atccattgca ctccggatgt gctgacccct gcgatttccc caaatgtggg aaactcgact    120
gcataatttg tggtagtggg ggactgcgtt cgcgctttcc cctgactttc tggagtttca    180
aaagtagact gtacgctaag ggtcatatct ttttttgttt tggtttgtgt cttggttggc    240
gtcttaaatg ttaatcctac agtggagggc tgcggaatag gaagtaacat gtcgcctgca    300
cgccatagga gaaaaagcga gcatcagccg tatcggcttt gtaacacaaa ttagctatcg    360
tgaagtccgc tcag                                                     374

SEQ ID NO: 78           moltype = RNA    length = 374
FEATURE                 Location/Qualifiers
source                  1..374
                        mol_type = other RNA
                        organism = synthetic construct
SEQUENCE: 78
atagctctct tacctcggag ataccatgat cacgaaggtg gttttcccag ggcgaggctt    60
atccattgca ctccggatgt gctgacccct gcgatttccc caaatgtggg aaactcgact    120
gcataatttg tggtagtggg ggactgcgtt cgcgctttcc cctgactttc tggagtttca    180
aaagtagact gtacgctaag ggtcatatct ttttttgttt tggtttgtgt cttggttggc    240
gtcttaaatg ttaatcctac agtggagggc tgcggaatag gaagtaacat gtcgcctgca    300
cgccatagga gaaaaagcga gcatcagccg tatcggcttt gtaacacaaa ttagctatcg    360
tgaagtccgc tcag                                                     374

SEQ ID NO: 79           moltype = DNA    length = 1221
FEATURE                 Location/Qualifiers
source                  1..1221
                        mol_type = other DNA
                        organism = synthetic construct
SEQUENCE: 79
cgttacataa cttacggtaa atggcccgcc tggctgaccg cccaacgacc cccgcccatt    60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catggtgatg cggttttggc agtacatcaa tgggcgtgga tagcggtttg actcacgggg    360
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagctct ctggctaact agagaaccca ctgcttactg    540
gcttatcgaa attaatacga ctcactatag ggagacccaa gctggctagc gtttaaactt    600
aagcttggta ccgagctcgg atccactagt ccagtgtggt ggaattcaag cttggtggtc    660
atggagaccc tggaccacct ggtgcccgg tgagtgacca gggaacactg cctggtgagg    720
```

```
gtctggaagg gctgggatag gcattggcca cagctgatga gccaggcctt ctctgtgtta   780
atccctgagc cctgttccct gcccttgacc cttttctctg gatccttttc cctccaggtg   840
aagttcgagg gcgataccct ggtgaatcgc atcgagctga ccggcaccga tttcaaggag   900
gatggcaaca tcctgggcaa taagatggag tacaactaca cgcccacaa tgtgtacatc   960
atgaccgaca aggccaagaa tggcatcaag gtgaacttca agatccgcca caacatcgag  1020
gatggcagcg tgcagctggc cgaccactac cagcagaata ccccatcgg cgatggccct  1080
gtgctgctgc ccgataacca ctacctgtcc acccagagcg ccctgtccaa ggaccccaac  1140
gagaagcgcg atcacatgat ctacttcggc ttcgtgaccg ccgccgccat cacccacggc  1200
atggatgagc tgtacaagtg a                                              1221

SEQ ID NO: 80        moltype = DNA   length = 26
FEATURE              Location/Qualifiers
source               1..26
                     mol_type = other DNA
                     organism = synthetic construct
SEQUENCE: 80
taatacgact cactataggg agaccc                                          26

SEQ ID NO: 81        moltype = DNA   length = 20
FEATURE              Location/Qualifiers
source               1..20
                     mol_type = other DNA
                     organism = synthetic construct
SEQUENCE: 81
ctccatctta ttgcccagga                                                 20

SEQ ID NO: 82        moltype = DNA   length = 2189
FEATURE              Location/Qualifiers
source               1..2189
                     mol_type = other DNA
                     organism = synthetic construct
SEQUENCE: 82
gtgatgcggt tttggcagta catcaatggg cgtggatagc ggtttgactc acggggattt    60
ccaagtctcc accccattga cgtcaatggg agtttgtttt ggcaccaaaa tcaacgggac   120
tttccaaaat gtcgtaacaa ctccgcccca ttgacgcaaa tgggcggtag gcgtgtacgg   180
tgggaggtct atataagcag agctctctgg ctaactagag aacccactgc ttactggctt   240
atcgaaatta atacgactca ctatagggag acccaagctg gctagcgttt aaacttaagc   300
ttggtaccga gctcggatcc actagtccag tgtggtggaa ttcaagcttc tccgagtgtt   360
caagttggca aagtcttggc ccacactgaa tatgctcatt aagatcattg gtaactcggt   420
gggagcactg ggcaacctga ctctggtgtt ggccatcatt gtctttatt ttgccgtggt   480
tggcatgcag ctgtttggaa aaagttacaa agattgtgtc tgcaaaattg ccactgactg   540
caaactccca cgttggcaca tgaacgactt cttccactcg ttcctgatcg tgttccgcgt   600
gctgtgtggg gagtggatag agaccatgtg ggactgcatg gaggtggcag gacaagctat   660
gtgccttact gtcttcatga tggtcatggt gattgggaac cttgtggtat gtacccaagt   720
tagatatgca tttcagaaat acatcaataa cataacaaat ttgtgcccaa tttattaaaa   780
aatgactttc atgataaata attttaaatg cctctgatct taagatatgt ttatcttctt   840
attctaaaaa tataccgcaa catggcaaaa tatagtatca caatctacta tggtaatata   900
gaaatacatc ttaaaacaaa tgtatgcaca ttaatattac ctatgatatt ttactctcaa   960
atccatattt tacagctcta ttttttttaag acaaggtttc tttctgtatc cctggctgtc  1020
ctggaacttg ctctgtagat ctagctgggc ttgaactcag agatccacct gcctctccat  1080
cccaagtact tggattaaag tgattgtgcc acctggcttc tcaactctat tttattcagt  1140
cacttcattg catttagtta ttaaaattgca taggactgtt aaaaatttac acaaatatgt  1200
tatgtgcgtg tgtttgtgtg tgatgtcttat gtgtgcgtgt gcatgtgagg agaaaagggg  1260
gcaattttg ctatagaata gtgctaacaa gaatggtcca tgcatatgtt gaagactttc  1320
attctaaatt tggtcatgac tatgattttt ttcagttatc atccaacaac acaaaatcat  1380
gaagagagaa acccaaaat acatttaaat aaataattgc aaatattaat catttttaaa  1440
tttggaattg ttaaagtatc tcagtaaata tatcttcttt tactcatata atattaaata  1500
taatgataaa ctaattcatt caagttcttc atttcatgta tgggagatct tgagagcagt  1560
agaagataat cctcatgtac atagagatgg agcaatatca caattcaga gtgctcaaaa  1620
cttttctagg gcggagtgtt gaacccaggg cctcatgttt tctggtcttg gcccacttaa  1680
cttctagcaa tgcctgtgct gtatcttgct catatagcat tcggttattc attctatagc  1740
taaaggaata agccatccta tgtcctctgt gttgtggtga acacatactt atgtctgttt  1800
tcaaggtcaa gttcgagggc gataccctgg tgaatcgcat cgagctgacc ggcaccgatt  1860
tcaaggagga tggcaacatc ctgggcaata agatggagta caactacacg cccacaatgt  1920
gtacatcat gaccgacaag gccaagaatg gcatcaaggt gaacttcaag atccgccaca  1980
acatcgagga tggcagcgtg cagctggccg accactacca gcagaatacc ccatcggcg  2040
atggccctgt gctgctgccc gataaccact acctgtccac ccagagcgcc ctgtccaagg  2100
accccaacga gaagcgcgat cacatgatct acttcggctt cgtgaccgcc gccgccatca  2160
cccacggcat ggatgagctg tacaagtga                                    2189

SEQ ID NO: 83        moltype = RNA   length = 373
FEATURE              Location/Qualifiers
source               1..373
                     mol_type = other RNA
                     organism = synthetic construct
SEQUENCE: 83
cgagctctct gcaggggaga taccatgatc acgaaggtgg ttttcccagg gcgaggctta    60
tccattgcac tccggatgtg ctgacccctg cgatttcccc aaatgtggga aactcgactg   120
cataaatttgt ggtagtgggg gactgcgttc gcgcttaaaa atgactttct ggagtttcaa   180
```

```
aagtagactg tacgctaagg gtcatatctt tttttgtttt ggtttgtgtc ttggttggcg    240
tcttaaatgt taatcctaca gtggagggct gcggaatagg aagtaacatg tcgcctgcac    300
gccataggag aaaaagcgag catcagccgt atcggctttg taacacaaat tagctatcgt    360
gaagtccgct cag                                                       373

SEQ ID NO: 84          moltype = RNA   length = 344
FEATURE                Location/Qualifiers
source                 1..344
                       mol_type = other RNA
                       organism = synthetic construct
SEQUENCE: 84
cgagctctct gcaggggaga taccatgatc acgaaggtgg ttttcccagg gcgaggctta    60
tccattgcac tccggatgtg ctgacccctg cgatttcccc aaatgtggga aactcgactg    120
cataatttgt ggtaactttc tggagtttca aaagtagact gtacgctaag ggtcatatct    180
tttttgtttt tggtttgtgt cttggttggc gtcttaaatg ttaatcctac agtggagggc    240
tgcggaatag gaagtaacat gtcgcctgca cgccatagga gaaaaagcga gcatcagccg    300
tatcggcttt gtaacacaaa ttagctatcg tgaagtccgc tcag                     344

SEQ ID NO: 85          moltype = RNA   length = 350
FEATURE                Location/Qualifiers
source                 1..350
                       mol_type = other RNA
                       organism = synthetic construct
SEQUENCE: 85
cgagctctct gcaggggaga taccatggtg gttttcccag ggcgaggctt atatgtgctg    60
accccgcga tttccccaaa tgtgggaaac tcgactgcat aatttgtgt agtggggac       120
tgcgttcgcg ctttccctg actttctgga gtttcaaaag tagactgtac gctaaggtc      180
atatcttttt tgtttgggt ttgtgtcttg gttggcgtct taaatgttaa tcctacagtg    240
gagggctgcg gaataggaag taacatgtcg cctgcacgcc ataggagaaa aagcgagcat    300
cagccgtatc ggctttgtaa cacaaattag ctatcgtgaa gtccgctcag               350

SEQ ID NO: 86          moltype = RNA   length = 372
FEATURE                Location/Qualifiers
source                 1..372
                       mol_type = other RNA
                       organism = synthetic construct
SEQUENCE: 86
gagctctctg caggggagat accatgatca cgaaggtggt tttcccaggg cgaggcttat    60
ccattgcact ccggatgtgc tgacccctgc gatttccca aatgtgggaa actcgactgc    120
ataatttgtg gtagtggggg actgcgttcg cgctttcccc tgactttctg gagtttcaaa    180
agtagactgt acgctaaggg tcatatcttt ttttgttttg gtttgtgtct tggttggcgt    240
cttaaatgtt aatcctacag tggagggctg cggaatagga agtaacatgt cgcctgcacg    300
ccataggaga aaaagcgagc atcagccgta tcggctttgt aacacaaatt agctatcgtg    360
aagtccgctc ag                                                        372

SEQ ID NO: 87          moltype = RNA   length = 373
FEATURE                Location/Qualifiers
source                 1..373
                       mol_type = other RNA
                       organism = synthetic construct
SEQUENCE: 87
aagaaactct gcaggggaga taccatgatc acgaaggtgg ttttcccagg gcgaggctta    60
tccattgcac tccggatgtg ctgacccctg cgatttcccc aaatgtggga aactcgactg    120
cataatttgt ggtagtgggg gactgcgttc gcgctttccc ctgactttct ggagtttcaa    180
aagtagactg tacgctaagg gtcatatctt tttttgtttt ggtttgtgtc ttggttggcg    240
tcttaaatgt taatcctaca gtggagggct gcggaatagg aagtaacatg tcgcctgcac    300
gccataggag aaaaagcgag catcagccgt atcggctttg taacacaaat tagctatcgt    360
gaagtccgct cag                                                       373

SEQ ID NO: 88          moltype = RNA   length = 373
FEATURE                Location/Qualifiers
source                 1..373
                       mol_type = other RNA
                       organism = synthetic construct
SEQUENCE: 88
aagaaaaact gcaggggaga taccatgatc acgaaggtgg ttttcccagg gcgaggctta    60
tccattgcac tccggatgtg ctgacccctg cgatttcccc aaatgtggga aactcgactg    120
cataatttgt ggtagtgggg gactgcgttc gcgctttccc ctgactttct ggagtttcaa    180
aagtagactg tacgctaagg gtcatatctt tttttgtttt ggtttgtgtc ttggttggcg    240
tcttaaatgt taatcctaca gtggagggct gcggaatagg aagtaacatg tcgcctgcac    300
gccataggag aaaaagcgag catcagccgt atcggctttg taacacaaat tagctatcgt    360
gaagtccgct cag                                                       373

SEQ ID NO: 89          moltype = RNA   length = 57
FEATURE                Location/Qualifiers
source                 1..57
                       mol_type = other RNA
                       organism = synthetic construct
SEQUENCE: 89
```

```
gacggcaact acaagtcgcg cgccgaggtc aagttcgagg gcgatacccg ggtgaat      57

SEQ ID NO: 90            moltype = RNA   length = 163
FEATURE                  Location/Qualifiers
source                   1..163
                         mol_type = other RNA
                         organism = synthetic construct
SEQUENCE: 90
cgagctctct gtccagggga aagcacaaac agttccccac tgccacaaat tatgtagtcg   60
agattccctc atttggggaa atcacagggg tcagcacatc cagagtaaaa ttgctaagcc   120
ttgccctgga aaaaccacct tcgtgatcat aacatttctt ctg                    163

SEQ ID NO: 91            moltype = RNA   length = 163
FEATURE                  Location/Qualifiers
source                   1..163
                         mol_type = other RNA
                         organism = synthetic construct
SEQUENCE: 91
cgagctctct gcaggggga aagcacaaac agttccccac tgccaccagg gcgaggctta    60
tccattgcac tccggatgtg ctgacccctg cgatttcccc aaatgtggga aactcgactg   120
cataatttgt ggtagtgggg gactgcgttc gcgctttccc ctg                    163

SEQ ID NO: 92            moltype = RNA   length = 163
FEATURE                  Location/Qualifiers
source                   1..163
                         mol_type = other RNA
                         organism = synthetic construct
SEQUENCE: 92
cgagctctct gcaggggaga taccatgatc acgaaggtgg ttttccaaat tatgtagtcg   60
agattccctc atttggggaa atcacagggg cgatttcccc aaatgtggga aactcgactg   120
cataatttgt ggtagtgggg gactgcgttc gcgctttccc ctg                    163

SEQ ID NO: 93            moltype = RNA   length = 163
FEATURE                  Location/Qualifiers
source                   1..163
                         mol_type = other RNA
                         organism = synthetic construct
SEQUENCE: 93
cgagctctct gcaggggaga taccatgatc acgaaggtgg ttttccaagt tatgcagtcg   60
agttcctcac attggggaa aatggcaggg cgatttcccc aaatgtggga aactcgactg    120
cataatttgt ggtagtgggg gactgcgttc gcgctttccc ctg                    163

SEQ ID NO: 94            moltype = RNA   length = 163
FEATURE                  Location/Qualifiers
source                   1..163
                         mol_type = other RNA
                         organism = synthetic construct
SEQUENCE: 94
cgagctctct gcaggggaga taccatgatc acgaaggtgg ttttcccagg gcgaggctta   60
tccattgcac tccggatgtg ctgacccctg tcagcacatc cggagtgcaa tggataactg   120
cataatttgt ggtagtgggg gactgcgttc gcgctttccc ctg                    163

SEQ ID NO: 95            moltype = RNA   length = 163
FEATURE                  Location/Qualifiers
source                   1..163
                         mol_type = other RNA
                         organism = synthetic construct
SEQUENCE: 95
cgagctctct gcaggggaga taccatgatc acgaaggtgg ttttcccagg gcgaggctta   60
tccattgcac tccggatgtg ctgacccctg tcagcacatc cagagtaaaa ttgctaactg   120
cataatttgt ggtagtgggg gactgcgttc gcgctttccc ctg                    163

SEQ ID NO: 96            moltype = RNA   length = 163
FEATURE                  Location/Qualifiers
source                   1..163
                         mol_type = other RNA
                         organism = synthetic construct
SEQUENCE: 96
cgagctctct gcaggggaga taccatgatc acgaaggtgg ttttcccagg gcgaggctta   60
tccattgcac tccggatgtg ctgacccctg gtcagtacac ccggaacata acggatactg   120
cataatttgt ggtagtgggg gactgcgttc gcgctttccc ctg                    163

SEQ ID NO: 97            moltype = RNA   length = 163
FEATURE                  Location/Qualifiers
source                   1..163
                         mol_type = other RNA
                         organism = synthetic construct
SEQUENCE: 97
cgagctctct gcaggggaga taccatgatc acgaaggtgg ttttcccagg gcgaggctta   60
```

-continued

```
tccattgcac tccggatgtg ctgacccctg cgatttcccc aaatgtggga aactcgactg    120
cataatttgt ggtagtacct tcgtgatcat aacatttctt ctg                      163
```

RNA EDITING VIA RECRUITMENT OF SPLICEOSOME COMPONENTS

CROSS-REFERENCE

This application is a continuation of International Application No. PCT/US2022/042486, filed Sep. 2, 2022, which claims the benefit of U.S. Provisional Application No. 63/240,428, filed Sep. 3, 2021, and U.S. Provisional Application No. 63/345,660, filed May 25, 2022, each of which applications are incorporated herein by reference.

STATEMENT AS TO FEDERALLY SPONSORED RESEARCH

This invention was made with government support under Contract number 2112383 awarded by National Science Foundation. The government has certain rights in the invention.

SEQUENCE LISTING

The instant application contains a Sequence Listing which has been submitted electronically in XML format and is hereby incorporated by reference in its entirety. Said XML file, created on Apr. 24, 2024, is named 309222000201SUB-SEQLIST.xml and is 102,759 bytes in size.

BACKGROUND

There is a long-felt but unmet need for replacing disease-causing RNA sequences. The disclosure provides compositions and methods for replacement of specific RNA sequences in RNA molecules in human cells. In certain aspects, the present disclosure provides compositions and methods for replacement of chosen RNA sequences within target RNAs. In some embodiments, the present disclosure provides RNA donor molecules used in conjunction with engineered small nuclear RNAs that recruit components of the spliceosome to the RNA donor and promote editing of target RNAs to treat a disease in the context of a human gene therapy.

Effective treatment of human genetic disease necessitates efficient replacement of defective genetic sequences in human cells. RNA editing has been proposed as a human gene therapeutic but has not experienced success in clinical trials due to low efficiency and limited size and composition of RNA edits. Furthermore, the use of immunogenic proteins to edit RNA and DNA has posed safety issues. The present disclosure describes improvements to RNA editing that could address this long-felt but unmet need.

SUMMARY

In certain aspects, disclosed herein is a composition comprising an engineered small nuclear RNA that promotes trans-splicing of a target RNA molecule and an RNA donor molecule. In some embodiments, the RNA donor molecule comprises a engineered small nuclear RNA domain. In some embodiments, the engineered small nuclear RNA molecule is derived or isolated from a human small nuclear RNA gene chosen from a group consisting of: U1, U2, U4, U5, U6, U7, U11, and U12. In some embodiments, the engineered small nuclear RNA molecule is derived or isolated from a U1 small nuclear RNA gene or variant of a U1 small nuclear RNA gene and contains an RNA motif that begins less than 16 nucleobases from the 5' end that is partially or perfectly complementary to the RNA donor molecule. In some embodiments, the engineered small nuclear RNA molecule contains an RNA motif that is partially or perfectly complementary to the RNA donor molecule. In some embodiments, the RNA motif is chosen from a group consisting of: 5'-CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3' (SEQ ID NO: 9), 5'-AGAGCTCGTTGCGA-3' (SEQ ID NO: 10), and 5'-GAGCTCGTTG-3' (SEQ ID NO: 11). In some embodiments, the engineered small RNA molecule comprises sequences derived or isolated from a U1 small nuclear RNA gene or variant of U1 small nuclear RNA gene. In some embodiments, the engineered small RNA molecule comprises sequences derived or isolated from a U1 small nuclear RNA gene and a variant of the U1 small nuclear RNA gene. In some embodiments, the variant of the U1 small nuclear RNA gene is chosen from a group consisting of: vU1.4, vU1.11, vU1.8, vU1.7, vU1.5, vU1.12. In some embodiments, the small nuclear RNA molecule comprises RNA, DNA, a DNA/RNA hybrid, a nucleic acid analog, a chemically-modified nucleic acid, or a chimera composed of two or more nucleic acids or nucleic acid analogs. In some embodiments, the RNA donor molecule further comprises an untranslated region that enhances translation. In some embodiments, the composition further comprises an RNA-binding protein that strengthens the interaction among the RNA donor molecule and the target RNA molecule and increases trans-splicing efficiency In some embodiments, the engineered small nuclear RNA molecule contains an RNA motif that is at least 4 nucleotides long and is partially or perfectly complementary to a sequence in the RNA donor molecule. In some embodiments, the RNA motif is chosen from a group consisting of: CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3' (SEQ ID NO: 9), 5'-AGAGCTCGTTGCGA-3' (SEQ ID NO: 10), and 5'-GAGCTCGTTG-3'. (SEQ ID NO: 11). In some embodiments, the RNA donor molecule contains an RNA motif that is at least 4 nucleotides long and is partially or perfectly complementary to a sequence in the RNA donor molecule. In some embodiments, the RNA donor molecule further comprises an untranslated region that enhances translation In some embodiments, the translation-enhancing element comprises a sequence derived or isolated from the group consisting of: Woodchuck Hepatitis Virus (WHV) Posttranscriptional Regulatory Element (WPRE), triplex from MALAT1, the PRE of Hepatitis B virus (HPRE), and an iron response element In some embodiments, the composition further comprises an RNA-binding protein that strengthens the interaction among the RNA donor molecule and the target RNA molecule and increases trans-splicing efficiency In some embodiments, the RNA donor molecule comprises RNA, DNA, a DNA/RNA hybrid, a nucleic acid analog, a chemically-modified nucleic acid, or a chimera composed of two or more nucleic acids or nucleic acid analogs. In some embodiments, the nucleic acid molecule further comprises a heterologous promoter. In some embodiments, described herein is a vector comprising the composition of claims disclosed herein. In some embodiments, the vector is selected from the group consisting of: adeno-associated virus, retrovirus, lentivirus, adenovirus, nanoparticle, micelle, liposome, lipoplex, polymersome, polyplex, and dendrimer. In some embodiments, described herein is a cell comprising the vector described herein. In some embodiments, described herein is a method for treating a disease comprising administering to a patient in need of a therapeutically effective amount of a treatment comprising the composition described herein or the vector described herein. In some embodiments, described herein is a method for correcting a genetic defect in a subject comprising administering to said subject the composition described herein or the vector described herein. In some embodiments, described herein is a method for treating a disease comprising administering to a patient in need of a therapeutically effective amount of a treatment the composition described herein or the vector described herein. In some embodiments, described herein is a method for correcting a genetic defect in a subject comprising administering to said subject the composition described herein or the vector described herein.

In certain aspects, disclosed herein is a composition comprising an engineered small nuclear RNA that promotes trans-splicing of a target RNA molecule and an RNA donor molecule, the RNA donor molecule comprising: (a) one or more replacement domains that encode a therapeutic sequence operably linked to; (b) one or more intronic domains that promote RNA splicing of the replacement domain; and (c) one or more antisense domains that promote binding to a target RNA molecule. In some embodiments, the RNA donor molecule comprises a engineered small nuclear RNA domain. In some embodiments, the engineered small nuclear RNA molecule is derived or isolated from a human small nuclear RNA gene chosen from a group consisting of: U1, U2, U4, U5, U6, U7, U11, and U12. In some embodiments, the engineered small nuclear RNA molecule is derived or isolated from a U1 small nuclear RNA gene or variant of a U1 small nuclear RNA gene and contains an RNA motif that begins less than 16 nucleobases from the 5' end that is partially or perfectly complementary to the RNA donor molecule. In some embodiments, the engineered small nuclear RNA molecule contains an RNA motif that is partially or perfectly complementary to the RNA donor molecule. In some embodiments, the RNA motif is chosen from a group consisting of: CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3' (SEQ ID NO: 9), 5'-AGAGCTCGTTGCGA-3' (SEQ ID NO: 10), and 5'-GAGCTCGTTG-3'. (SEQ ID NO: 11). In some embodiments, the engineered small RNA molecule comprises sequences derived or isolated from a U1 small nuclear RNA gene or variant of U1 small nuclear RNA gene. In some embodiments, the engineered small RNA molecule comprises sequences derived or isolated from a U1 small nuclear RNA gene and a variant of the U1 small nuclear RNA gene. In some embodiments, the variant of the U1 small nuclear RNA gene is chosen from a group consisting of: vU1.4, vU1.11, vU1.8, vU1.7, vU1.5, vU1.12. In some embodiments, the small nuclear RNA molecule comprises RNA, DNA, a DNA/RNA hybrid, a nucleic acid analog, a chemically-modified nucleic acid, or a chimera composed of two or more nucleic acids or nucleic acid analogs. In some embodiments, the RNA donor molecule further comprises an untranslated region that enhances translation. In some embodiments, the composition further comprises an RNA-binding protein that strengthens the interaction among the RNA donor molecule and the target RNA molecule and increases trans-splicing efficiency In some embodiments, the engineered small nuclear RNA molecule contains an RNA motif that is at least 4 nucleotides long and is partially or perfectly complementary to a sequence in the RNA donor molecule. In some embodiments, the RNA motif is chosen from a group consisting of: CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3' (SEQ ID NO: 9), 5'-AGAGCTCGTTGCGA-3' (SEQ ID NO: 10), and 5'-GAGCTCGTTG-3'. (SEQ ID NO: 11). In some embodiments, the RNA donor molecule contains an RNA motif that is at least 4 nucleotides long and is partially or perfectly complementary to a sequence in the RNA donor molecule. In some embodiments, the RNA donor molecule further comprises an untranslated region that enhances translation In some embodiments, the translation-enhancing element comprises a sequence derived or isolated from the group consisting of: Woodchuck Hepatitis Virus (WHV) Posttranscriptional Regulatory Element (WPRE), triplex from MALAT1, the PRE of Hepatitis B virus (HPRE), and an iron response element In some embodiments, the composition further comprises an RNA-binding protein that strengthens the interaction among the RNA donor molecule and the target RNA molecule and increases trans-splicing efficiency In some embodiments, the RNA donor molecule comprises RNA, DNA, a DNA/RNA hybrid, a nucleic acid analog, a chemically-modified nucleic acid, or a chimera composed of two or more nucleic acids or nucleic acid analogs. In some embodiments, the nucleic acid molecule further comprises a heterologous promoter. In some embodiments, described herein is a vector comprising the composition of claims disclosed herein. In some embodiments, the vector is selected from the group consisting of: adeno-associated virus, retrovirus, lentivirus, adenovirus, nanoparticle, micelle, liposome, lipoplex, polymersome, polyplex, and dendrimer. In some embodiments, described herein is a cell comprising the vector described herein. In some embodiments, described herein is a method for treating a disease comprising administering to a patient in need of a therapeutically effective amount of a treatment comprising the composition described herein or the vector described herein. In some embodiments, described herein is a method for correcting a genetic defect in a subject comprising administering to said subject the composition described herein or the vector described herein. In some embodiments, described herein is a method for treating a disease comprising administering to a patient in need of a therapeutically effective amount of a treatment the composition described herein or the vector described herein. In some embodiments, described herein is a method for correcting a genetic defect in a subject comprising administering to said subject the composition described herein or the vector described herein.

In certain aspects, disclosed herein is a composition comprising an RNA donor molecule, comprising: (a) one or more replacement domains that encode a therapeutic sequence operably linked to; (b) one or more intronic domains that promote RNA splicing of the replacement domain; and (c) one or more antisense domains that promote binding to a target RNA molecule; and (d) an engineered small nuclear RNA domain that promotes trans-splicing of the RNA donor molecule. In some embodiments, the engineered small nuclear RNA domain is located less than 200 bases away from a splice donor site in the RNA donor molecule. In some embodiments, the engineered small nuclear RNA domain is isolated or derived from a human small nuclear RNA gene. In some embodiments, the human small nuclear RNA gene is chosen from a group consisting of: U1, U2, U4, U5, U6, U7, U11, and U12. In some embodiments, the engineered small nuclear RNA domain is synthetic and binds components of the spliceosome. In some embodiments, the engineered small nuclear RNA domain comprises sequences isolated or derived from a variant of the human U1 gene. In some embodiments, the engineered small nuclear RNA domain comprises sequences derived from the human U1 small nuclear RNA gene and a variant of the U1 small nuclear RNA gene. In some embodiments, the RNA donor molecule further comprises an untranslated region that enhances translation. In some embodiments, the composition further comprises an RNA-binding protein that strengthens the interaction among the RNA donor molecule and the target RNA molecule and increases trans-splicing efficiency In some embodiments, the engineered small nuclear RNA molecule contains an RNA motif that is at least 4 nucleotides long and is partially or perfectly complementary to a sequence in the RNA donor molecule. In some embodiments, the RNA motif is chosen from a group consisting of: CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3' (SEQ ID NO: 9), 5'-AGAGCTCGTTGCGA-3' (SEQ ID NO: 10), and 5'-GAGCTCGTTG-3'. (SEQ ID NO: 11). In some embodiments, the RNA donor molecule contains an RNA motif that is at least 4 nucleotides long and is partially or perfectly complementary to a sequence in the RNA donor molecule. In some embodiments, the RNA donor molecule further comprises an untranslated region that enhances translation In some embodiments, the translation-enhancing element comprises a sequence derived or isolated from the group consisting of: Woodchuck Hepatitis Virus (WHV) Posttranscriptional Regulatory Element (WPRE), triplex from MALAT1, the PRE of Hepatitis B virus (HPRE), and an iron response element In some embodiments, the composition further comprises an RNA-binding protein that strengthens the interaction among the RNA donor molecule and the target RNA molecule and increases trans-splicing efficiency In some embodiments, the RNA donor molecule comprises RNA, DNA, a DNA/RNA hybrid, a nucleic acid analog, a chemically-modified nucleic acid, or a chimera composed of two or more nucleic acids or nucleic acid analogs. In some embodiments, the nucleic acid molecule further comprises a heterologous promoter. In some embodiments, described herein is a vector comprising the composition of claims disclosed herein. In some embodiments, the vector is selected from the group consisting of: adeno-associated virus, retrovirus, lentivirus, adenovirus, nanoparticle, micelle, liposome, lipoplex, polymersome, polyplex, and dendrimer. In some embodiments, described herein is a cell comprising the vector described herein. In some embodiments, described herein is a method for treating a disease comprising administering to a patient in need of a therapeutically effective amount of a treatment comprising the composition described herein or the vector described herein. In some embodiments, described herein is a method for correcting a genetic defect in a subject comprising administering to said subject the composition described herein or the vector described herein. In some embodiments, described herein is a method for treating a disease comprising administering to a patient in need of a therapeutically effective amount of a treatment the composition described herein or the vector described herein. In some embodiments, described herein is a method for correcting a genetic defect in a subject comprising administering to said subject the composition described herein or the vector described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1A illustrates the concept of human genetic disease where mutated ("defective") DNA sequences are transcribed into RNA which directly contribute to disease ("RNA pathogenicity") or indirectly via translation into disease-causing protein ("translation of pathogenic protein"). FIG. 1B illustrates a system composed of a donor RNA and an engineered small nuclear RNA ("esnRNA"). The combination of RNA donor molecule and esnRNA correct mutated RNAs via hybridization of the RNA donor to the target RNA carrying a mutation, followed by association of the esnRNA with the RNA donor, which results in recruitment of spliceosome components and trans-splicing among the RNA donor molecule and the target RNA. This yields a corrected target RNA with the RNA donor molecule replacing a chosen sequence in the target RNA. FIG. 1C illustrates the how the components interact. Base pairing among the RNA donor and target RNA bring these molecule in close proximity. Base pairing among the esnRNA and the RNA donor brings spliceosome components in close proximity which promotes a trans-splicing reaction among the target RNA and the RNA donor.

FIG. 2A illustrates a version that results in replacement in internal sequences within a target RNA molecule. This embodiment results in retention of the 5' and 3' termini of the target RNA while replacing an internal sequence with the RNA donor molecule. FIG. 2B illustrates that results in replacement of the 5'-terminal portion of the target RNA while retaining the 3' end of the target RNA.

In FIG. 3B, the esnRNA is a domain within the RNA donor. In both cases, the esnRNA sequence acts by the same mechanism where recruitment of spliceosome components to the RNA donor drives trans-splicing among the target RNA and RNA donor.

FIG. 4A illustrates the design of a split GFP reporter that carries a N-terminal and a C-terminal portion of GFP ("C-GFP") but lacks an internal GFP sequence required for fluorescence. In the reporter, this internal GFP sequence is replaced by a short exon with a stop codon that is flanked by introns. The internal sequence is the replacement sequence within the RNA donor molecule that is flanked by one intronic domain and one antisense domain. FIG. 4B illustrates the activity of the reporter alone so that cis-splicing produces a GFP sequence interrupted by a stop codon therefore producing no GFP signal. FIG. 4C illustrates the activity of the reporter in the presence of the RNA donor molecule without inclusion of the esnRNA so that similarly cis-splicing occurs primarily and GFP signal is not produced. FIG. 4D illustrates the activity of the reporter in the presence of the RNA donor molecule with inclusion of esnRNA so that trans-splicing occurs primarily and GFP signal is produced.

FIGS. 5A-5B illustrate an experiment designed to reveal the importance of the esnRNA in the context of replacement of an 5'-terminal sequence in a target RNA. FIG. 5A illustrates the design of a split GFP reporter that carries a C-terminal portion of GFP ("C-GFP") but lacks an N-terminal GFP sequence required for fluorescence. In the reporter, this N-terminal GFP sequence is replaced by a short exon that is flanked by introns. The N-terminal sequence ("N-GFP") is the replacement sequence within an RNA donor molecule that is flanked by one intronic sequence and one antisense domain. FIG. 5B illustrates the activity of the reporter alone so that cis-splicing produces a GFP sequence lacking the N-terminal portion of GFP therefore producing no GFP signal. FIG. 5C illustrates the activity of the reporter in the presence of the RNA donor molecule without the esnRNA so that similarly cis-splicing occurs primarily and GFP signal is not efficiently produced.

DETAILED DESCRIPTION

Figure 1A:
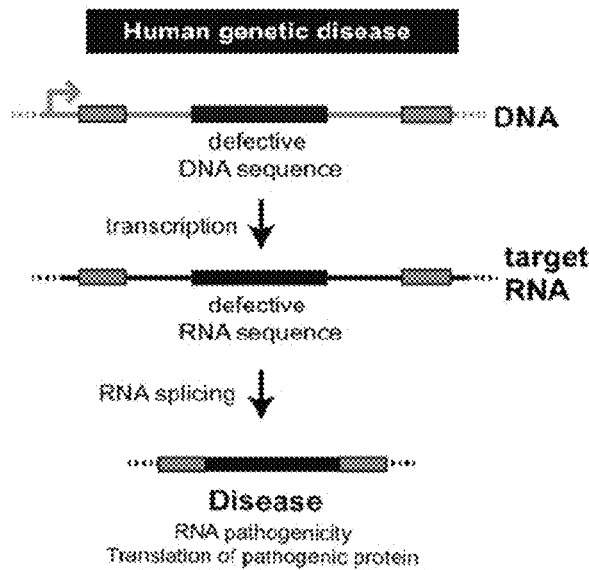
FIGS. 1A-1C illustrate one embodiments of the methods described herein.

In one aspect, disclosed herein is an RNA technology that enables replacement of arbitrary sequences within specific RNA molecules in living cells. Without being bound by theory, this technology, based on RNA trans-splicing, utilizes the naturally-existing spliceosome in human cells to provide the catalytic activity for this trans-splicing process Typically, RNA splicing occurs within RNA molecules where exons are concatenated and introns removed from immature messenger RNA molecules (pre-mRNAs) to form mature messenger RNA molecules (mRNAs). This process is referred to as cis-splicing. RNA trans-splicing is a process by which the spliceosome concatenates exons derived from distinct and separate RNA molecules. This process rarely occurs in human cells and state-of-the-art systems that promote RNA trans-splicing are active at low levels. Described herein are compositions that increase the efficiency of RNA trans-splicing. These improved RNA trans-splicing compositions could be used to replace mutated sequences within a target RNA molecule to address a human disease. Replacement of arbitrary RNA sequences is a general ability with innumerable specific applications a few of which have been explored as relevant demonstrations. RNA trans-splicing can insert engineered sequences into a target RNA to impart new activities to the target RNA such as altered RNA stability or altered RNA translation. This feature can be used to increase production of protein by a target RNA. In the broadest sense, this RNA trans-splicing technology can impart arbitrary changes to both coding and non-coding regions of target RNAs.

The presently disclosed RNA trans-splicing technology which involves the use of a RNA donor molecule and an esnRNA molecule is the first to show RNA-trans-splicing with high efficiency against multiple RNA targets. Highly efficient RNA trans-splicing has three primary advantages over previous RNA trans-splicing systems. First, this improved efficiency can replace defective RNA sequences at levels sufficient to reconstitute the activity of mutated genes to treat recessive genetic disorders. Indeed, treatment of many recessive gene disorders require at least 15% efficiency, where 100% is complete replacement of a sequence within a Target RNA. Second, this improved efficiency can replace defective RNA sequences at levels sufficient to treat genetic disorders involving a toxic gain of function mutation. As elimination of the RNA carrying a toxic mutation is required to treat these diseases, many diseases in this class require highly-efficient replacement of mutated sequences. As a result, even higher efficiency is required (50%+). Finally, the broad ability of the RNA trans-splicing technology described herein to modify multiple Target RNAs demonstrates a broadly-applicable and efficient version of this technology. This is a very general capability, with this disclosure providing demonstrations of RNA trans-splicing system that can efficiently replace sequences with multiple target RNAs.

The inclusion of an esnRNA molecule to form the present technology is a capability that further allows the alteration of both coding and non-coding sequences within target RNAs. By replacing the 5' or 3' untranslated regions of Target RNAs with high efficiency, this allows the alteration of RNA behaviors such as translation or turnover. The net result of these effects is increased production of protein from Target RNAs or other downstream effects associated with altered RNA levels.

RNA Molecules for Promoting Trans-Splicing

In certain embodiments, the compositions described herein comprise RNA molecules for promoting trans-splicing. In one aspect, described herein is an RNA donor molecule. In some embodiments, the RNA donor binds a target RNA molecule and a esnRNA molecule to promote trans-splicing. In another embodiment, the RNA donor molecule comprises an esnRNA domain.

Figure 3A:
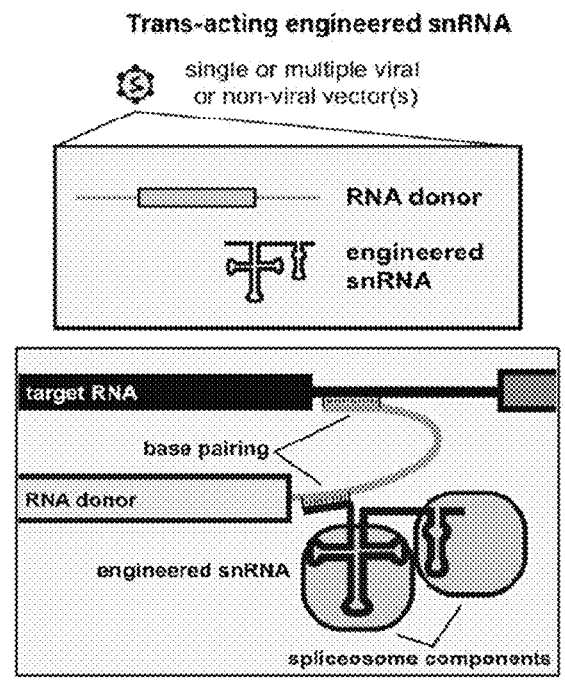
FIGS. 3A-3B illustrate two non-limiting embodiments. In one embodiment (FIG. 3A), the esnRNA and the RNA are separate molecules and the esnRNA and RNA donor associate in a manner outlined in FIG. 1C.

In some embodiments, the RNA donor molecule does not comprise a esnRNA domain. An example is depicted in FIG. 3A. In one aspect, described herein is an esnRNA molecule and an RNA donor molecule comprising three domains. In some embodiments, RNA donor molecule comprises a Replacement Domain. The Replacement Domain may be inserted into a Target RNA molecule via a trans-splicing reaction In some embodiments, RNA donor molecule comprises an Antisense Domain which is complementary to a Target RNA. In some embodiments, RNA donor molecule comprises an Intronic Domain, which promotes the trans-splicing reaction between RNA donor molecule and the Target RNA. In some embodiments, the esnRNA molecule is isolated or derived from a human small nuclear RNA gene but has been altered to contain a sequence that is complementary to the RNA donor molecule. Without being bound by theory, the combination of a trans-splicing RNA donor molecule and a esnRNA that contacts the RNA donor molecule results in replacement of chosen sequences within a target RNA in a manner that is sufficiently efficient to replace disease-causing RNA sequences in human cells to address disease. In some embodiments, the disclosure provides compositions and methods for targeting disease-causing RNA molecules in a sequence-specific manner and replacing disease-causing RNA sequences within these RNA molecules with high efficiency. In some embodiments, the RNA donor molecule and esnRNA implementations show utility in a variety of contexts including replacement of disease-causing sequences or insertion of engineered sequences into Target RNAs. In some embodiments, the engineered sequences can alter the translation or stability of Target RNAs to increase or decrease protein production or Target RNA levels. In some embodiments, this disclosure provides vectors, compositions and cells comprising or encoding RNA donor molecule and esnRNA molecule and methods of using the trans-splicing RNA compositions.

In certain aspects, described herein is a composition comprising an engineered small nuclear RNA ("esnRNA") molecule derived or isolated from a human spliceosomal snRNA gene and an RNA donor molecule comprising (a) at least one domain that promotes trans-splicing ("Intronic Domain"), (b) at least one binding domain ("Antisense Domain") that contains or consists of a sequence complementary to a pre-mRNA present in a human cells ("Target RNA"), and (c) a coding domain that is inserted into the Target RNA via trans-splicing ("Replacement Domain"). The esnRNA molecule binds the RNA donor molecule and recruits spliceosome components which promotes trans-splicing among the RNA donor molecule and the Target RNA, therefore inserting the RNA donor molecule sequence into the Target RNA. In other embodiments, the present disclosure provides a composition comprising a nucleic acid sequence encoding RNA donor molecule and the esnRNA molecule. In other embodiments, the present disclosure provides a composition comprising two nucleic acid sequences encoding the RNA donor molecule and the esnRNA, respectively.

In certain aspects, described herein is a single RNA molecule that contains two domains (the RNA donor domain and the esnRNA domain), wherein the single RNA molecule selectively binds a target RNA molecule and promotes a trans-splicing reaction with the target RNA molecule with high efficiency. In certain aspects, the disclosure provides vectors, compositions and cells comprising or encoding the single RNA molecule. In certain aspects, the disclosure provides methods of using the single RNA molecule, vectors, compositions and cells of the disclosure to treat a disease or disorder.

Figure 3B:
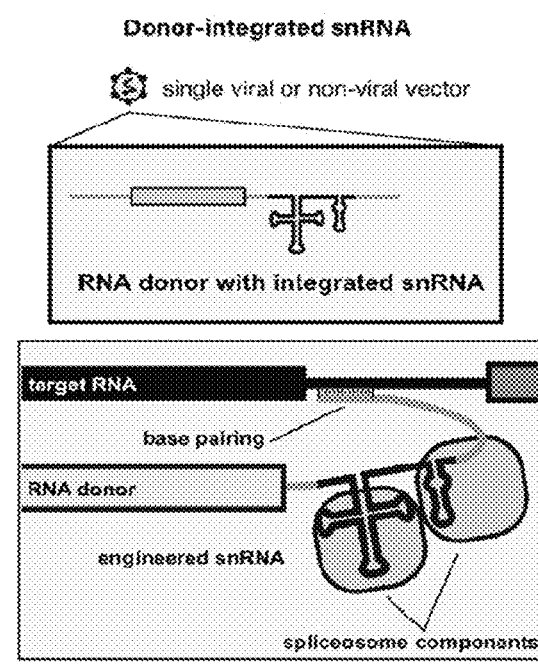
Figure 4A:
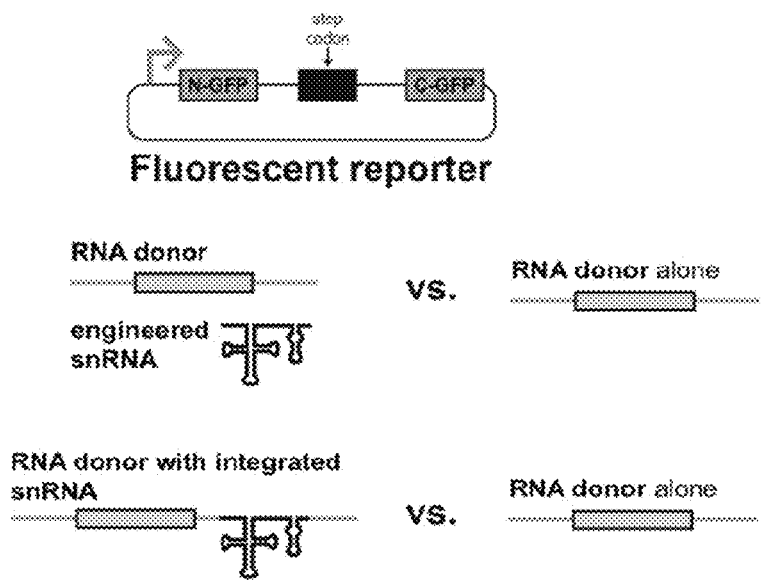
FIGS. 4A-4D illustrate an experiment designed to reveal the importance of the esnRNA in the context of replacement of an internal sequence in a target RNA.
Figure 4B:
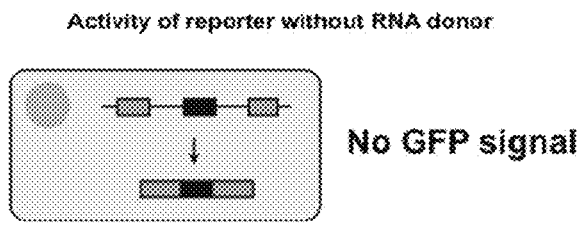
Figure 4C:
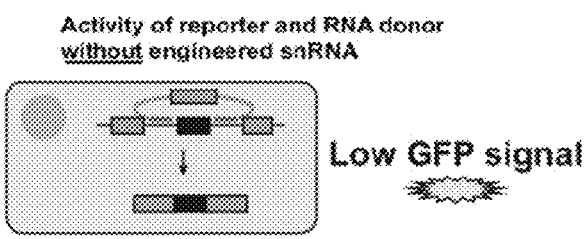
Figure 4D:
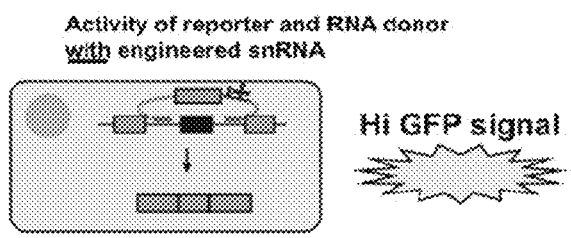
Figure 5A:
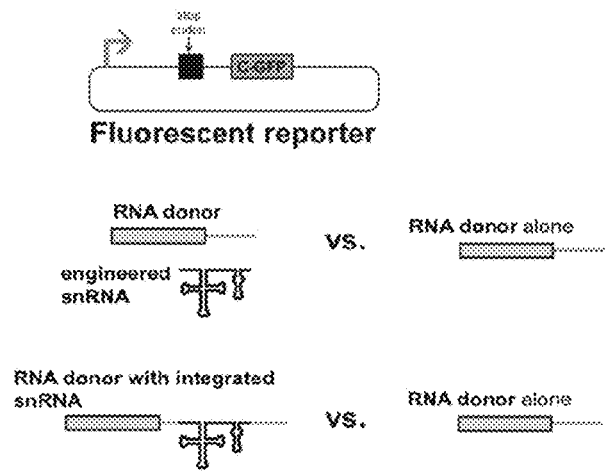
Figure 5D:
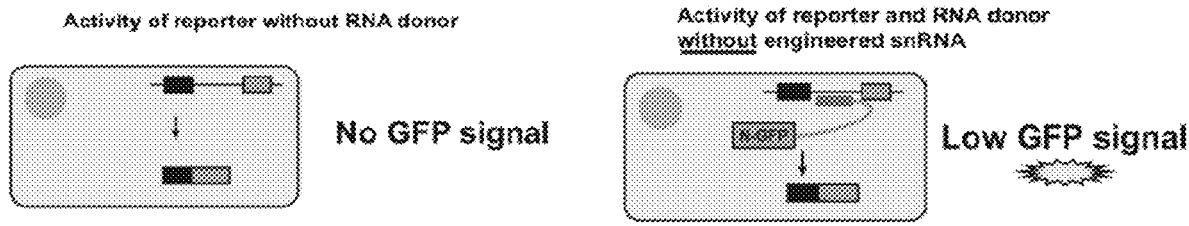
FIG. 5D illustrates the activity of the reporter in the presence of the RNA donor with inclusion of esnRNA so that trans-splicing occurs primarily and GFP signal is efficiently produced.
Figure 5D:
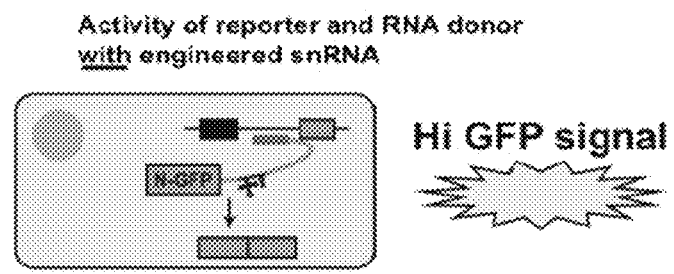

In some embodiments, the RNA donor molecule comprises a esnRNA domain. An example is depicted in FIG. 3B. In one aspect, disclosed herein is an RNA donor molecule comprising at least four domains. In some embodiments, the RNA donor molecule comprises a Replacement Domain. The Replacement Domain may be inserted into a Target RNA molecule via a trans-splicing reaction. In some embodiments, the RNA donor molecule comprises an Antisense Domain, which is complementary to a Target RNA. In some embodiments, the RNA donor molecule comprises an Intronic Domain, which promotes the trans-splicing reaction between the RNA donor molecule and the Target RNA. In some embodiments, the RNA donor molecule comprises a esnRNA domain, which is isolated or derived from a human small nuclear RNA gene.

The present disclosure provides, in some embodiments, a composition comprising an RNA donor molecule comprising (a) at least one domain that promotes trans-splicing ("Intronic Domain"), (b) at least one binding domain ("Antisense Domain") that contains or consists of a sequence complementary to a pre-mRNA present in a human cells ("Target RNA"), (c) a coding domain that is inserted into the Target RNA via trans-splicing ("Replacement Domain"), and (d) engineered small nuclear RNA ("esnRNA") domain which comprises an esnRNA sequence. The esnRNA domain recruits spliceosome components which promotes trans-splicing among the RNA donor molecule and the Target RNA, therefore inserting the RNA donor molecule sequence into the Target RNA. In other embodiments, the present disclosure provides a composition comprising a nucleic acid sequence encoding RNA donor molecule.

esnRNA Molecules and Domains

In some embodiments, the methods and compositions described herein comprise an esnRNA molecule comprising an esnRNA domain. In some embodiments, the methods and compositions described herein comprise a RNA donor molecule comprising an esnRNA domain. In some embodiments, the esnRNA domain is derived or isolated from a human small nuclear RNA gene is chosen from a group consisting of: U1, U2, U4, U5, U6, U7, U11, and U12.

Compositions comprising esnRNA molecules and esnRNA domains disclosed herein include any sequences that are derived or isolated from human small nuclear RNA genes. Small nuclear RNA genes include without limitation: U1, U2, U4, U5, U6, U7, U11, and U12. The esnRNA molecule may contain sequences that are complementary to the RNA donor molecule. This complementary sequence may be located at or near the 5' end of the esnRNA molecule. Complementary sequences incudes without limitation:

5'CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3 (SEQ ID NO: 9)', 5'-AGAGCTCGTTGCGA-3' (SEQ ID NO: 10), and 5'-GAGCTCGTTG-3' (SEQ ID NO: 11). In some embodiments, in the above complementary sequences, none, some, or all, of the thymidine bases may be replaced with uracil so that the trans-splicing enhancer sequences include without limitation: 5'-CGAGCUCUCU-3' (SEQ ID NO: 12), 5'-AACGAGCUCU-3' (SEQ ID NO: 13), 5'-CGCAACGAGC-3' (SEQ ID NO: 3), 5'-UAUCGCAACG-3' (SEQ ID NO: 14), 5'-AAUAAUAUCG-3' (SEQ ID NO: 15), 5'-UAAGAGAGCU-3' (SEQ ID NO: 16), 5'-AAGAGAGCUC-3' (SEQ ID NO: 17), 5'-AGAGAGCUCGUUGC-3' (SEQ ID NO: 18), 5'-GAGAGCUCGU-3' (SEQ ID NO: 19), 5'-AGAGCUCGUUGCGA-3' (SEQ ID NO: 20), and 5'-GAGCUCGUUG-3' (SEQ ID NO: 21).

In some embodiments, the esnRNA domain contains one or more stem-loop forming RNA sequences derived or isolated from a human small nuclear RNA gene. In one embodiment, such an esnRNA domain has at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to its corresponding wild-type or originating sequence. In one embodiment, such an esnRNA domain has at most about 80%, at most about 85%, at most about 90%, at most about 91%, at most about 92%, at most about 93%, at most about 94%, at most about 95%, at most about 96%, at most about 97%, at most about 98%, at most about 99%, or 100% sequence identity to its corresponding wild-type or originating sequence.

In some embodiments, the esnRNA molecule or esnRNA domain is not derived from any living organism and is composed of a synthetic sequence that binds spliceosomal proteins.

In some embodiments, esnRNA domain is located at least about 1 nucleotide distant from the Replacement Domain. In some embodiments, the esnRNA domain is located at least about 2 nucleotides, at least about 3 nucleotides, at least about 4 nucleotides, at least about 5 nucleotides, at least about 6 nucleotides, at least about 7 nucleotides, at least about 8 nucleotides, at least about 9 nucleotides, at least about 10 nucleotides, at least about 11 nucleotides, at least about 12 nucleotides, at least about 13 nucleotides, at least about 14 nucleotides, at least about 15 nucleotides, at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 31 nucleotides, at least about 31 nucleotides, at least about 32 nucleotides, at least about 33 nucleotides, at least about 34 nucleotides, at least about 35 nucleotides, at least about 36 nucleotides, at least about 37 nucleotides, at least about 38 nucleotides, at least about 39 nucleotides, at least about 40 nucleotides, at least about 41 nucleotides, at least about 42 nucleotides, at least about 43 nucleotides, at least about 44 nucleotides, at least about 45 nucleotides, at least about 46 nucleotides, at least about 47 nucleotides, at least about 48 nucleotides, at least about 49 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 110 nucleotides, at least about 120 nucleotides, at least about 130 nucleotides, at least about 140 nucleotides, at least about 150 nucleotides, at least about 160 nucleotides, at least about 170 nucleotides, at least about 180 nucleotides, at least about 190 nucleotides, at least about 200 nucleotides, at least about 250 nucleotides, at least about 300 nucleotides, at least about 400 nucleotides, at least about 500 nucleotides, or more than 500 nucleotides distant from the first or last nucleotide of the Replacement Sequence in the RNA donor molecule in the 5' direction. In some embodiments, the esnRNA domain is located at most about 2 nucleotides, at most about 3 nucleotides, at most about 4 nucleotides, at most about 5 nucleotides, at most about 6 nucleotides, at most about 7 nucleotides, at most about 8 nucleotides, at most about 9 nucleotides, at most about 10 nucleotides, at most about 11 nucleotides, at most about 12 nucleotides, at most about 13 nucleotides, at most about 14 nucleotides, at most about 15 nucleotides, at most about 16 nucleotides, at most about 17 nucleotides, at most about 18 nucleotides, at most about 19 nucleotides, at most about 20 nucleotides, at most about 21 nucleotides, at most about 22 nucleotides, at most about 23 nucleotides, at most about 24 nucleotides, at most about 25 nucleotides, at most about 26 nucleotides, at most about 27 nucleotides, at most about 28 nucleotides, at most about 29 nucleotides, at most about 30 nucleotides, at most about 31 nucleotides, at most about 31 nucleotides, at most about 32 nucleotides, at most about 33 nucleotides, at most about 34 nucleotides, at most about 35 nucleotides, at most about 36 nucleotides, at most about 37 nucleotides, at most about 38 nucleotides, at most about 39 nucleotides, at most about 40 nucleotides, at most about 41 nucleotides, at most about 42 nucleotides, at most about 43 nucleotides, at most about 44 nucleotides, at most about 45 nucleotides, at most about 46 nucleotides, at most about 47 nucleotides, at most about 48 nucleotides, at most about 49 nucleotides, at most about 50 nucleotides, at most about 55 nucleotides, at most about 60 nucleotides, at most about 65 nucleotides, at most about 70 nucleotides, at most about 75 nucleotides, at most about 80 nucleotides, at most about 85 nucleotides, at most about 90 nucleotides, at most about 95 nucleotides, at most about 100 nucleotides, at most about 110 nucleotides, at most about 120 nucleotides, at most about 130 nucleotides, at most about 140 nucleotides, at most about 150 nucleotides, at most about 160 nucleotides, at most about 170 nucleotides, at most about 180 nucleotides, at most about 190 nucleotides, at most about 200 nucleotides, at most about 250 nucleotides, at most about 300 nucleotides, at most about 400 nucleotides, at most about 500 nucleotides, or at most about 500 nucleotides distant from the first or last nucleotide of the Replacement Sequence in the RNA donor molecule in the 5' direction.

In some embodiments of the compositions of the disclosure, there may be an esnRNA sequence that promotes trans-splicing. In some embodiments of the compositions of the disclosure, esnRNA is derived or isolated from the human U1 snRNA gene. In some embodiments of the compositions of the disclosure, the sequences esnRNA is derived or isolated from a U1 snRNA variant. In some embodiments of the compositions of the disclosure, the U1 snRNA variant is selected from the list consisting of (name followed by genomic location in brackets according to UCSC human genome assembly 2006): tU1.1 [0:16713367-16712967], tU1.2 [chr1:16866030-16865630], vU1.1 [chr1:142438700-142438300], vU1.2 [chr1:142464813-142464413], vU1.4 [chr1:143022739-143022339], vU1.5 [chr1:143202968-143202568], vU1.7 [chr1:144680790-144680390], vU1.8 [chr1:145022927-145022527], vU1.9 [chr1:145977791-145977391], vU1.10 [chr1:146301289-146300889], vU1.11 [chr1:146327427-146327027], vU1.15 [chr1:146871696-146871296], vU1.16 [chr1:147033726-147033326], vU1.17 [chr1:147460893-147460493], vU1.18 [chr1:147490845-147490445], vU1.19 [chr1:147780880-147780480], tU1.3 [chr1:16939762-16940162], tU1.4 [chr1:17095226-17095626], vU1.3 [chr1:142478876-142479276], vU1.6 [chr1:144094114-144094514], vU1.12 [chr1:146341486-146341886], vU1.13 [chr1:146460770-146461170], vU1.14 [chr1:146608089-146608489], vU1.20 [chr1:147872535-147872935].

In some embodiments of the compositions of the disclosure, the sequences of the esnRNA comprise or consist of (esnRNA 1):

(SEQ ID NO: 22)
CGAGCTCTCTgCAGGGGAAAGCGCGAACGCAGTACCACTACCACAAATT

ATGCAATCGAGTTTCCCACATTTGGGGAAATCGCAGGGGTCAACACATC

TGGAGTGCAATGGATAAGCCTCGCCCTGGGAAAACCACCTTCGTGATCA

TGTTATCTCCCCTG

In some embodiments of the compositions of the disclosure, the sequences of the esnRNA comprise or consist of (esnRNA 2):

(SEQ ID NO: 23)
CGAGCTCTCTgTCCAGGGGAAAGCACAAACAGTTCCCCACTGCCACAAA

TTATGTAGTCGAGATTCCCTCATTTGGGGAAATCACAGGGGTCAGCACA

TCCAGAGTAAAATTGCTAAGCCTTGCCCTGGAAAAACCACCTTCGTGAT

CATAACATTTCTTCTG

In some embodiments of the compositions of the disclosure, the sequences of the esnRNA comprise or consist of (esnRNA 3):

(SEQ ID NO: 24)
CGAGCTCTCTgCAGGGAAAAACACAGACACAGTTCCCCACTGCCACAAAT

TATGTAATCAAGATTCCCACATTCGGGGAAATCACAGGGGTCAGCACATC

CACAGTAAAACTGCTAAGCCTTGCTCTGGAAAAACCACCTTCGTGATCAT

AACATTTCTTCTG

In some embodiments of the compositions of the disclosure, the sequences of the esnRNA comprise or consist of (esnRNA 4):

(SEQ ID NO: 25)
CGAGCTCTCTgCAGGGGAAAGCGCGGACGCAGTCCCCCACTACCACAAAT

TATGCAGTCGAGTTTCCCACATTTGGGGAAATCGCAGGGGTCAGCACATC

CGGAGTGCAATGGATAAGCCTCGCCCTGGGAAAACCACCTTCGTGATCAT

GGTATCTCCCCTG

In some embodiments of the compositions of the disclosure, the sequences of the esnRNA comprise or consist of (esnRNA 5):

(SEQ ID NO: 26)
CGAGCTCTCTgGGGGGAAAAGAGCGAACGCAGTCTCCCACTACCACAAAT

TATGCAGTCGAGCTTCCCACATTTGGGGAAGTTGCACGAATTAGCTTCGC

CCTGCGAAAACCACCTTCGTAAACACGATTTTTCTTCTGCTAGGTAAATG

TGAGTCTGCACGC

In some embodiments of the compositions of the disclosure, the sequences of the esnRNA comprise or consist of (esnRNA 6):

(SEQ ID NO: 27)
CGAGCTCTCTgCAGAGGACAGCGCGAACGCAGTCCCCCACTACCACAAAT

TATGCAGTCGAGTTTCCCACATTTGGGGAAACGGCAGGGGTCAGCACATC

CGGAGTGCAATGGATAAGCCTCTCCCTGGGAAAACCACCTTCGTGATCAT

CGTATCTCCCCTG

In some embodiments of the compositions of the disclosure, the sequences of the esnRNA comprise or consist of (esnRNA 7):

(SEQ ID NO: 23)
CGAGCTCTCTgTCCAGGGGAAAGCACAAACAGTTCCCCACTGCCACAAAT

TATGTAGTCGAGATTCCCTCATTTGGGGAAATCACAGGGGTCAGCACATC

CAGAGTAAAATTGCTAAGCCTTGCCCTGGAAAAACCACCTTCGTGATCAT

AACATTTCTTCTG

In some embodiments of the compositions of the disclosure, the sequences of the esnRNA comprise or consist of (esnRNA 8):

(SEQ ID NO: 28)
CGAGCTCTCTgCAGAGGAAAGCGCGAACGCAGTCCCCCACTACCACAAAT

TATGCAATCGAGTTTCCCACGTTTGGGGAAATCGCAGAGGTCAGCACATC

CGGAACACAATGGATAACCCTCGCCCTGAGAAAACCACCTTCGTTTAGA

TAATAGTATCTCCCCTG

In some embodiments of the compositions of the disclosure, the sequences of the esnRNA comprise or consist of (esnRNA 9):

(SEQ ID NO: 29)
CGAGCTCTCTgCAAGAGAAAGCGCGAACGTAGTTCCCTACTATCACAAAT

TATGCACTCGAGTTTCCCACACTTGGGGAAATCGCAGGGGTCAGCACATC

CGGAACGCAATGGATAAGCTTCGCCCTGAGAAAACCACCTTCGTGATCA

TGGTATCTCCCCTT

In some embodiments of the compositions of the disclosure, the sequences of the esnRNA comprise or consist of (esnRNA 10):

(SEQ ID NO: 30)
CGAGCTCTCTgCAGGGGAAAGCGCGAACGCAGTCCCCTACTATCACAAGT

TATGCAGTCGAGTTCCTCACATTGGGGGAAAATGGCAGGGGTCAGTACAC

CCGGAACATAACGGATAAGCCTCGCCCTGAGAAAACCACCTTCGTGATCA

TGGTATCTCCCCCG

In some embodiments of the compositions of the disclosure, the sequences of the esnRNA comprise or consist of (esnRNA 11):

(SEQ ID NO: 31)
CGAGCTCTCTgCAGGGGAAAACGCGAACACAGTCCCCTACTATCACAAGT

TATGCAGTCGAGTTCCTCACATTGGGGGAAAATGGCAGGGGTCAGTACAC

CCGGAACATAACGGATAAGCCTCGCCCTGAGAAAACCACCTTCGTGATCA

TGGTATCTCCCCCG

In some embodiments of the compositions of the disclosure, the sequences of the esnRNA comprise or consist of (esnRNA 12):

(SEQ ID NO: 32)
CGAGCTCTCTgCAGGGGAGATAGTATGATCATGAAAGTGGTTTTTCCAGA

GCGAGGCTTATCCATTGCACTCCGGATGTGTTGACCTCTGCGATTTCCCC

AACTGTGGGAAACTCGACTGCGTAATTTGTGGTAGTGGGGGACTGCGTTC

GCGCTTTCCCCTG

In some embodiments of the compositions of the disclosure, the sequences of the esnRNA comprise or consist of (esnRNA 13):

(SEQ ID NO: 33)
CGAGCTCTCTgCAGGGGAGATACTATTATCAAACGAAGGTGGTTTTTCTC

AGGGCGAGGCTTATCCATTGTGTTCCGGATGTGCTGACCTCTGCGATTTC

CCCAAACGTGGGAAACTCGACTGCATAATTTGTGGTAGTGGGGGACTGCG

TTCGCGCTTTCCTCTG

In some embodiments of the compositions of the disclosure, the sequences of the esnRNA comprise or consist of (esnRNA 14):

(SEQ ID NO: 34)
CGAGCTCTCTgCAGAAGAAATGTTATGATCACGAAGGTGGTTTTTCCAGA

GCAAGGCTTAGCAGTTTTACTGTGGATGTGCTGACCCCTGTGATTTCCCC

GAATGTGGGAATCTTGATTACATAATTTGTGGCAGTGGGGAACTGTGTCT

GTGTTTTCCCCTG

In some embodiments of the compositions of the disclosure, the sequences of the esnRNA comprise or consist of (esnRNA 15):

(SEQ ID NO: 35)
CGAGCTCTCTgcagggGAAAGCGCGAACGCAGTACCACTACCACAAcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 16):

(SEQ ID NO: 36)
CGAGCTCTCTgcagggGGGAAAGCACAAACAGTTCCCCACTGCCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 17):

(SEQ ID NO: 37)
CGAGCTCTCTgcagggAAAAACACAGACACAGTTCCCCACTGCCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 18):

(SEQ ID NO: 38)
CGAGCTCTCTgcagggGAAAGCGCGGACGCAGTCCCCCACTACCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 19):

(SEQ ID NO: 39)
CGAGCTCTCTgcagggAAAAGAGCGAACGCAGTCTCCCACTACCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 20):

(SEQ ID NO: 40)
CGAGCTCTCTgcagggGACAGCGCGAACGCAGTCCCCCACTACCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 21):

(SEQ ID NO: 91)
CGAGCTCTCTgcagggGGGAAAGCACAAACAGTTCCCCACTGCCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 22):

(SEQ ID NO: 41)
CGAGCTCTCTgcagggGAAAGCGCGAACGCAGTCCCCCACTACCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 23):

(SEQ ID NO: 42)
CGAGCTCTCTgcagggGAAAGCGCGAACGTAGTTCCCTACTATCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 24):

(SEQ ID NO: 43)
CGAGCTCTCTgcagggGAAAGCGCGAACGCAGTCCCCTACTATCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 25):

(SEQ ID NO: 44)
CGAGCTCTCTgcagggGAAAACGCGAACACAGTCCCCTACTATCACcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 26):

(SEQ ID NO: 45)
CGAGCTCTCTgcagggGAGATAGTATGATCATGAAAGTGGTTTTTCcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 27):

In some embodiments of the compositions of the disclosure, the sequences of the esnRNA comprise or consist of (esnRNA 28):

(SEQ ID NO: 46)
CGAGCTCTCTgcagggGAGATACTATTATCAAACGAAGGTGGTTTTcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 29):

(SEQ ID NO: 47)
CGAGCTCTCTgcagggGAAATGTTATGATCACGAAGGTGGTTTTTCcagg gcgaggcttatccattgcactccggatgtgctgacccctgcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 30):

(SEQ ID NO: 48)
CGAGCTCTCTgcaggggagataccaTGATCAcgaaggtggttttccATTA

TGCAATCGAGTTTCCCACATTTGGGGAAATCGCAGGGGTCcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 31):

(SEQ ID NO: 49)
CGAGCTCTCTgcaggggagataccaTGATCAcgaaggtggttttccAAAT

TATGTAGTCGAGATTCCCTCATTTGGGGAAATCACAGGGGcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 32):

(SEQ ID NO: 50)
CGAGCTCTCTgcaggggagataccaTGATCAcgaaggtggttttccAAAT

TATGTAATCAAGATTCCCACATTCGGGGAAATCACAGGGGcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 32):

(SEQ ID NO: 51)
CGAGCTCTCTgcaggggagataccaTGATCAcgaaggtggttttccAAAT

TATGCAGTCGAGTTTCCCACATTTGGGGAAATCGCAGGGGcgatttcccc aaatgtgggaaactcgactgcataatttgtggtagtgggggactgcgttc gcgctttcccctg In some embodiments of the compositions of the disclosure, the sequences of the esnRNA comprise or consist of (esnRNA 33):

(SEQ ID NO: 52)
CGAGCTCTCTgcaggggagataccaTGATCAcgaaggtggttttccAAA

TTATGCAGTCGAGCTTCCCACATTTGGGGAAGTTGCACGAAcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 34):

(SEQ ID NO: 92)
CGAGCTCTCTgcaggggagataccaTGATCAcgaaggtggttttccAAA

TTATGTAGTCGAGATTCCCTCATTTGGGGAAATCACAGGGGcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 35):

(SEQ ID NO: 53)
CGAGCTCTCTgcaggggagataccaTGATCAcgaaggtggttttccAAA

TTATGCAATCGAGTTTCCCACGTTTGGGGAAATCGCAGAGGcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 36):

(SEQ ID NO: 54)
CGAGCTCTCTgcaggggagataccaTGATCAcgaaggtggttttccAAA

TTATGCACTCGAGTTTCCCACACTTGGGGAAATCGCAGGGGcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 37):

(SEQ ID NO: 55)
CGAGCTCTCTgcaggggagataccaTGATCAcgaaggtggttttccAAG

TTATGCAGTCGAGTTCCTCACATTGGGGGAAAATGGCAGGGcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 38):

(SEQ ID NO: 93)
CGAGCTCTCTgcaggggagataccaTGATCAcgaaggtggttttccAAG

TTATGCAGTCGAGTTCCTCACATTGGGGGAAAATGGCAGGGcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 39):

(SEQ ID NO: 56)
CGAGCTCTCTgcaggggagataccaTGATCAcgaaggtggttttccCAG

AGCGAGGCTTATCCATTGCACTCCGGATGTGTTGACCTCTGcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 41):

(SEQ ID NO: 57)
CGAGCTCTCTgcaggggagataccaTGATCAcgaaggtggttttccTCT

CAGGGCGAGGCTTATCCATTGTGTTCCGGATGTGCTGACCTcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 42):

(SEQ ID NO: 58)
CGAGCTCTCTgcaggggagataccaTGATCAcgaaggtggttttccCAG

AGCAAGGCTTAGCAGTTTTACTGTGGATGTGCTGACCCCTGcgatttcc ccaaatgtgggaaactcgactgcataatttgtggtagtgggggactgcg ttcgcgctttcccctg In some embodiments of the compositions of the disclosure, the sequences of the esnRNA comprise or consist of (esnRNA 44):

(SEQ ID NO: 59)
CGAGCTCTCTgcaggggagataccaTGATCAcgaaggtggttttcccag ggcgaggcttatccattgcactccggatgtgctgacccctgAACACATC TGGAGTGCAATGGATAAGactgcataatttgtggtagtgggggactgcg ttcgcgctttcccctg In some embodiments of the compositions of the disclosure, the sequences of the esnRNA comprise or consist of (esnRNA 46):

(SEQ ID NO: 60)
CGAGCTCTCTgcaggggagataccaTGATCAcgaaggtggttttcccag ggcgaggcttatccattgcactccggatgtgctgacccctgTCAGCACA TCCAGAGTAAAATTGCTAactgcataatttgtggtagtgggggactgcg ttcgcgctttcccctg In some embodiments of the compositions of the disclosure, the sequences of the esnRNA comprise or consist of (esnRNA 47):

(SEQ ID NO: 61)
CGAGCTCTCTgcaggggagataccaTGATCAcgaaggtggttttcccag ggcgaggcttatccattgcactccggatgtgctgacccctgTCAGCACA TCCGGAGTGCAATGGATAactgcataatttgtggtagtgggggactgcg ttcgcgctttcccctg In some embodiments of the compositions of the disclosure, the sequences of the esnRNA comprise or consist of (esnRNA 48):

(SEQ ID NO: 62)
CGAGCTCTCTgcaggggagataccaTGATCAcgaaggtggttttccca gggcgaggcttatccattgcactccggatgtgctgacccctgTTAGCT TCGCCCTGCGAAAACCACCTactgcataatttgtggtagtgggggact gcgttcgcgctttcccctg In some embodiments of the compositions of the disclosure, the sequences of the esnRNA comprise or consist of (esnRNA 49):

(SEQ ID NO: 94)
CGAGCTCTCTgcaggggagataccaTGATCAcgaaggtggttttcccag ggcgaggcttatccattgcactccggatgtgctgacccctgTCAGCACA TCCGGAGTGCAATGGATAactgcataatttgtggtagtgggggactgcg ttcgcgctttcccctg In some embodiments of the compositions of the disclosure, the sequences of the esnRNA comprise or consist of (esnRNA 51):

(SEQ ID NO: 95)
CGAGCTCTCTgcaggggagataccaTGATCAcgaaggtggttttcccag ggcgaggcttatccattgcactccggatgtgctgacccctgTCAGCACA TCCAGAGTAAAATTGCTAactgcataatttgtggtagtgggggactgcg ttcgcgctttcccctg In some embodiments of the compositions of the disclosure, the sequences of the esnRNA comprise or consist of (esnRNA 52):

(SEQ ID NO: 63)
CGAGCTCTCTgcaggggagataccaTGATCAcgaaggtgg ttttcccagggcgaggcttatccattgcactccggatgtg ctgacccctgTCAGCACATCCGGAACACAATGGATAactg cataatttgtggtagtgggggactgcgttcgcgctttccc ctg In some embodiments of the compositions of the disclosure, the sequences of the esnRNA comprise or consist of (esnRNA 53):

(SEQ ID NO: 64)
CGAGCTCTCTgcaggggagataccaTGATCAcgaaggtgg ttttcccagggcgaggcttatccattgcactccggatgtg ctgacccctgTCAGCACATCCGGAACGCAATGGATAactg cataatttgtggtagtgggggactgcgttcgcgctttccc ctg In some embodiments of the compositions of the disclosure, the sequences of the esnRNA comprise or consist of (esnRNA 54):

(SEQ ID NO: 65)
CGAGCTCTCTgcaggggagataccaTGATCAcgaaggtgg ttttcccagggcgaggcttatccattgcactccggatgtg ctgacccctgGTCAGTACACCCGGAACATAACGGATactg cataatttgtggtagtgggggactgcgttcgcgctttccc ctg In some embodiments of the compositions of the disclosure, the sequences of the esnRNA comprise or consist of (esnRNA 55):

(SEQ ID NO: 96)
CGAGCTCTCTgcaggggagataccaTGATCAcgaaggtgg ttttcccagggcgaggcttatccattgcactccggatgtg ctgacccctgGTCAGTACACCCGGAACATAACGGATactg cataatttgtggtagtgggggactggttcgcgctttcccc tg In some embodiments of the compositions of the disclosure, the sequences of the esnRNA comprise or consist of (esnRNA 56):

(SEQ ID NO: 66)
CGAGCTCTCTgcaggggagataccaTGATCAcgaaggtgg ttttcccagggcgaggcttatccattgcactccggatgtg ctgacccctgCGATTTCCCCAACTGTGGGAAACTCGactg cataatttgtggtagtgggggactgcgttcgcgctttccc ctg In some embodiments of the compositions of the disclosure, the sequences of the esnRNA comprise or consist of (esnRNA 57):

(SEQ ID NO: 67)
CGAGCTCTCTgcaggggagataccaTGATCAcgaaggtgg ttttcccagggcgaggcttatccattgcactccggatgtg ctgacccctgCTGCGATTTCCCCAAACGTGGGAAACactg cataatttgtggtagtgggggactgcgttcgcgctttccc ctg In some embodiments of the compositions of the disclosure, the sequences of the esnRNA comprise or consist of (esnRNA 58):

(SEQ ID NO: 68)
CGAGCTCTCTgcaggggagataccaTGATCAcgaaggtgg ttttcccagggcgaggcttatccattgcactccggatgtg ctgacccctgcgatttccccaaatgtgggaaactcgactg cataatttgtggtagtCTTCGTGATCATGTTATCTCCCCT

G

In some embodiments of the compositions of the disclosure, the sequences of the esnRNA comprise or consist of (esnRNA 59):

(SEQ ID NO: 69)
CGAGCTCTCTgcaggggagataccaTGATCAcgaaggtgg ttttcccagggcgaggcttatccattgcactccggatgtg ctgacccctgcgatttccccaaatgtgggaaactcgactg cataatttgtggtagtACCTTCGTGATCATAACATTTCTT

CTG

In some embodiments of the compositions of the disclosure, the sequences of the esnRNA comprise or consist of (esnRNA 60):

(SEQ ID NO: 69)
CGAGCTCTCTgcaggggagataccaTGATCAcgaaggtgg ttttcccagggcgaggcttatccattgcactccggatgtg ctgacccctgcgatttccccaaatgtgggaaactcgactg cataatttgtggtagtACCTTCGTGATCATAACATTTCTT

CTG

In some embodiments of the compositions of the disclosure, the sequences of the esnRNA comprise or consist of (esnRNA 61):

(SEQ ID NO: 70)
CGAGCTCTCTgcaggggagataccaTGATCAcgaaggtgg ttttcccagggcgaggcttatccattgcactccggatgtg ctgacccctgcgatttccccaaatgtgggaaactcgactg cataatttgtggtagtACCTTCGTGATCATGGTATCTCCC

CTG

Antisense Domain

In some embodiments of the disclosure, an Antisense Domain of the disclosure binds to a target sequence. In some embodiments of the disclosure, an Antisense Domain of the disclosure binds to a target RNA.

In some embodiments of the disclosure, the Antisense Domain is chosen so that successful trans-splicing causes removal of micro open reading frames in the Target RNA. In this manner, the trans-splicing system removes micro open reading frames and increases the production of protein from the target RNA.

In some embodiments of the compositions of the disclosure, the sequence comprising the Antisense Domain has at least about 50%, at least about 55%, at least about 60%, at least about 65%, at least about 70%, at least about 75%, at least about 80%, at least about 87%, at least about 90%, at least about 91%, at least about 92%, at least about 93%, at least about 94%, at least about 95%, at least about 96%, at least about 97%, at least about 98%, at least about 99% or any percentage in between of complementarity to the Target RNA sequence. In some embodiments, the sequence comprising the Antisense Domain has at most about 50%, at most about 55%, at most about 60%, at most about 65%, at most about 70%, at most about 75%, at most about 80%, at most about 87%, at most about 90%, at most about 91%, at most about 92%, at most about 93%, at most about 94%, at most about 95%, at most about 96%, at most about 97%, at most about 98%, at most about 99% or any percentage in between of complementarity to the Target RNA sequence. In some embodiments, the Antisense Domain has 100% complementarity to the Target RNA sequence. In some embodiments, the Antisense Domain comprises or consists of at least about 20 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides, at least about 110 nucleotides, at least about 120 nucleotides, at least about 130 nucleotides, at least about 140 nucleotides, at least about 150 nucleotides, at least about 160 nucleotides, at least about 170 nucleotides, at least about 180 nucleotides, at least about 190 nucleotides, at least about 200 nucleotides, at least about 210 nucleotides, at least about 220 nucleotides, at least about 230 nucleotides, at least about 240 nucleotides, at least about 250 nucleotides, at least about 260 nucleotides, at least about 270 nucleotides, or at least about more than 270 nucleotides in between the complementary to the Target RNA sequence. In some embodiments, the Antisense Domain comprises or consists of at most about 20 nucleotides, at most about 30 nucleotides, at most about 40 nucleotides, at most about 50 nucleotides, at most about 60 nucleotides, at most about 70 nucleotides, at most about 80 nucleotides, at most about 90 nucleotides, at most about 100 nucleotides, at most about 110 nucleotides, at most about 120 nucleotides, at most about 130 nucleotides, at most about 140 nucleotides, at most about 150 nucleotides, at most about 160 nucleotides, at most about 170 nucleotides, at most about 180 nucleotides, at most about 190 nucleotides, at most about 200 nucleotides, at most about 210 nucleotides, at most about 220 nucleotides, at most about 230 nucleotides, at most about 240 nucleotides, at most about 250 nucleotides, at most about 260 nucleotides, at most about 270 nucleotides, or at most about more than 270 nucleotides in between the complementary to the Target RNA sequence.

In some embodiments of the compositions and methods of the disclosure, the target sequence comprises or consists of at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 125 nucleotides, at least about 150 nucleotides, at least about 175 nucleotides, at least about 200 nucleotides, at least about 225 nucleotides, at least about 250 nucleotides, at least about 275 nucleotides, at least about 300 nucleotides, at least about 325 nucleotides, at least about 350 nucleotides, at least about 375 nucleotides, at least about 400 nucleotides, at least about 425 nucleotides, at least about 450 nucleotides, at least about 475 nucleotides, at least about 500 nucleotides, or more than 500 nucleotides. In some embodiments, the target sequence comprises or consists of at most about 5 nucleotides, at most about 10 nucleotides, at most about 15 nucleotides, at most about 20 nucleotides, at most about 25 nucleotides, at most about 30 nucleotides, at most about 35 nucleotides, at most about 40 nucleotides, at most about 45 nucleotides, at most about 50 nucleotides, at most about 55 nucleotides, at most about 60 nucleotides, at most about 65 nucleotides, at most about 70 nucleotides, at most about 75 nucleotides, at most about 80 nucleotides, at most about 85 nucleotides, at most about 90 nucleotides, at most about 95 nucleotides, at most about 100 nucleotides, at most about 125 nucleotides, at most about 150 nucleotides, at most about 175 nucleotides, at most about 200 nucleotides, at most about 225 nucleotides, at most about 250 nucleotides, at most about 275 nucleotides, at most about 300 nucleotides, at most about 325 nucleotides, at most about 350 nucleotides, at most about 375 nucleotides, at most about 400 nucleotides, at most about 425 nucleotides, at most about 450 nucleotides, at most about 475 nucleotides, or at most about 500 nucleotides. In some embodiments, the target sequence comprises or consists of between about 5 and about 500 nucleotides. In some embodiments, the target sequence comprises or consists of between about 50 and about 250 nucleotides. In some embodiments, the target sequence comprises or consists of between about 5 and about 50 nucleotides.

In some embodiments of the compositions of the disclosure, a pathogenic RNA molecule is a target RNA. In some embodiments, the target RNA comprises a target sequence that is complementary to an antisense domain of the trans-splicing RNA of the disclosure.

In some embodiments of the compositions and methods of the disclosure, a target sequence is contained within a single contiguous stretch of the target RNA. In some embodiments, the target sequence may consist of comprise of one or more nucleotides that are not spread among a single contiguous stretch of the target RNA.

In some embodiments, the Antisense Domain is complementary to a gene (corresponding accession numbers in brackets, corresponding disease in parentheses) that encodes a Target RNA that sometimes carry disease-causing mutations and is selected from the group consisting of: TNFRSF13B [ENSG00000240505] (common variable immune deficiency); ADA, CECR1 [ENSG00000196839, ENSG00000093072] (Adenosine deaminase deficiency); IL2RG [ENSG00000147168] (X-linked severe combined immunodeficiency); HBB [ENSG00000244734] (Beta-thassalemia); HBA1, HBA2 [ENSG00000206172, ENSG00000188536] (alpha-thassalemia); U2AF1 [ENSG00000160201] (myelodysplastic syndrome); SOD1, TARDBP, FUS, MATR3, SOD1, C9ORF72 [ENSG00000142168, ENSG00000120948, ENSG00000089280, ENSG00000015479, ENSG00000142168, ENSG00000147894] (Amyotrophic lateral sclerosis); MAPT, PGRN [ENSG00000186868, ENSG00000030582] (Frontotemporal dementia with parkinsonism); CDH23, MYO7A, USH2A

[ENSG00000107736, ENSG00000137474, ENSG00000042781] (Usher's syndrome); GALC [ENSG00000054983] (Krabbe disease); SMPD1, NPC1, NPC2 [ENSG00000166311, ENSG00000141458, ENSG00000119655] (Niemann Pick disease); PRNP [ENSG00000171867](prion disease); SCN1A [ENSG00000144285] (Dravet syndrome); PINK1, ATP-GAP2 [ENSG00000158828] (early-onset Parkinson's disease); ATXN1, ATXN2, ATXN3, PLEKHG4, SPTBN2, CACNA1A, ATXN7, TTBK2, PPP2R2B, KCNC3, PRKCG, ITPR1, TBP, KCND1, FGF14 [ENSG00000124788, ENSG00000204842, ENSG00000066427, ENSG00000196155, ENSG00000173898, ENSG00000141837, ENSG00000163635, ENSG00000128881, ENSG00000156475, ENSG00000131398, ENSG00000126583, ENSG00000150995, ENSG00000112592, ENSG00000102057, ENSG00000102466] (spinocerebellar ataxias); SCN1A, SCN2A, CACNA1A, GRIN2B, GRIN2A, MECP2, FOXG1, SLC6A1, PRRT2, PTEN, KCNQ2, KCNQ3, STARD7, CLRN1 [ENSG00000144285, ENSG00000136531, ENSG00000141837, ENSG00000273079, ENSG00000183454, ENSG00000169057, ENSG00000176165, ENSG00000157103, ENSG00000167371, ENSG00000171862, ENSG00000075043, ENSG00000184156, ENSG00000084090, ENSG00000163646] (genetic epilepsy disorders); ATM [ENSG00000149311] (Ataxia-telangiectasia); GLB1 [ENSG00000170266] (GM1 gangliosidosis); GBA [ENSG00000177628] (Gaucher disease); GM2A [ENSG00000196743] (GM2 gangliosidosis); UBE3A [ENSG00000114062] (Angelman syndrome); SLC2A1 [ENSG00000117394] (glucose transporter deficiency type 1); LAMP2 [ENSG00000005893] (Danon disease); GLA [ENSG00000102393] (Fabry disease); PKD1, PKD2 [ENSG00000008710, ENSG00000118762] (Autosomal dominant polycystic kidney disease); GAA [ENSG00000171298] (Pompe disease); PCSK9, LDLR, APOB, APOE [ENSG00000169174, ENSG00000130164, ENSG00000084674, ENSG00000130203] (Familial hypercholesterolemia); MYOC, OPTN, TBK1, WDR36, CYPIB1 [ENSG00000034971, ENSG00000123240, ENSG00000183735, ENSG00000134987, ENSG00000138061] (Open Angle Glaucoma); IDUA [ENSG00000127415] (Hurler syndrome or Mucopolysaccharidosis 1); IDS [ENSG00000010404] (Hunter syndrome or Mucopolysaccharidosis 2); CLN3 [ENSG00000188603] (Batten disease); DMD [ENSG00000198947] (Duchenne muscular dystrophy); LMNA [ENSG00000160789] (Limb-girdle muscular dystrophy type 1B); DYSF [ENSG00000135636] (Limb-girdle muscular dystrophy type 2B); SGCA [ENSG00000108823](Limb-girdle muscular dystrophy type 2D); SGCB [ENSG00000163069] (Limb-girdle muscular dystrophy type 2E); SGCG [ENSG00000102683] (Limb-girdle muscular dystrophy type 2C); SGCD [ENSG00000170624] (Limb-girdle muscular dystrophy type 2F); DUX4 [ENSG00000260596] (Facioscapulohumeral muscular dystrophy); F9 [ENSG00000101981](Hemophilia B); F8 [ENSG00000185010] (Hemophilia A); USHA2A, RPGR, RP2, RHO, PRPF31, USH1F, PRPF3, PRPF6 [ENSG00000102218, ENSG00000156313, ENSG00000163914, ENSG00000105618, ENSG00000150275, ENSG00000117360, ENSG00000101161] (Retinitis pigmentosa); CFTR [ENSG00000001626] (cystic fibrosis); GJB2, GJB6, STRC, DFNA1, WFS1 [ENSG00000165474, ENSG00000121742, ENSG00000242866, ENSG00000131504, ENSG00000109501] (autosomal dominant hearing impairment); POU3F3 [ENSG00000198914] (nonsyndromic hearing loss).

Replacement Domain

In some embodiments, the methods and compositions described herein comprise an RNA donor molecule comprising a Replacement Domain. In some embodiments, the Replacement domain is derived or isolated from the Target RNA.

In some embodiments, the Replacement Domain is comprised of sequence derived or isolated from a human gene. In some embodiments, the sequence comprising the Replacement Domain has at least about 50%, at least about 55%, at least about 60%, at least about 65%, at least about 70%, at least about 75%, at least about 80%, at least about 87%, at least about 90%, at least about 95%, at least about 97%, at least about 99% or any percentage in between of identity with a human gene. In some embodiments, the sequence comprising the Replacement Domain has at most about 50%, at most about 55%, at most about 60%, at most about 65%, at most about 70%, at most about 75%, at most about 80%, at most about 87%, at most about 90%, at most about 95%, at most about 97%, at most about 99% or any percentage in between of identity with a human gene. In some embodiments, the Replacement Domain has 100% identity with a sequence derived or isolated from a human gene. In some embodiments, the Replacement Domain comprises or consists of at least about 2 nucleotides, at least about 5 nucleotides, at least about 10 nucleotides, at least about 20 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides, at least about 110 nucleotides, at least about 120 nucleotides, at least about 130 nucleotides, at least about 140 nucleotides, at least about 150 nucleotides, at least about 160 nucleotides, at least about 170 nucleotides, at least about 180 nucleotides, at least about 190 nucleotides, at least about 200 nucleotides, at least about 210 nucleotides, at least about 220 nucleotides, at least about 230 nucleotides, at least about 240 nucleotides, at least about 250 nucleotides, at least about 260 nucleotides, at least about 270 nucleotides, more than 270 nucleotides, or any number of nucleotides in between. In some embodiments, the Replacement Domain comprises or consists of at most about 2 nucleotides, at most about 5 nucleotides, at most about 10 nucleotides, at most about 20 nucleotides, at most about 30 nucleotides, at most about 40 nucleotides, at most about 50 nucleotides, at most about 60 nucleotides, at most about 70 nucleotides, at most about 80 nucleotides, at most about 90 nucleotides, at most about 100 nucleotides, at most about 110 nucleotides, at most about 120 nucleotides, at most about 130 nucleotides, at most about 140 nucleotides, at most about 150 nucleotides, at most about 160 nucleotides, at most about 170 nucleotides, at most about 180 nucleotides, at most about 190 nucleotides, at most about 200 nucleotides, at most about 210 nucleotides, at most about 220 nucleotides, at most about 230 nucleotides, at most about 240 nucleotides, at most about 250 nucleotides, at most about 260 nucleotides, at most about 270 nucleotides, or any number of nucleotides in between.

Compositions comprising replacement domains disclosed herein include any strategies where replacement or insertion of RNA sequences could be an effective therapy. Examples of replacement domains include without limitation sequences derived or isolated from the following genes (with gene accession IDs in brackets and associated diseases in parentheses) such as TNFRSF13B [ENSG00000240505] (common variable immune deficiency); ADA, CECR1 [ENSG00000196839, ENSG00000093072] (Adenosine deaminase deficiency); IL2RG [ENSG00000147168] (X-linked severe combined immunodeficiency); HBB [ENSG00000244734] (Beta-thassalemia); HBA1, HBA2 [ENSG00000206172, ENSG00000188536] (alpha-thassalemia); U2AF1 [ENSG00000160201] (myelodysplastic syndrome); SOD1, TARDBP, FUS, MATR3, SOD1, C9ORF72 [ENSG00000142168, ENSG00000120948, ENSG00000089280, ENSG00000015479, ENSG00000142168, ENSG00000147894] (Amyotrophic lateral sclerosis); MAPT, PGRN [ENSG00000186868, ENSG00000030582] (Frontotemporal dementia with parkinsonism); CDH23, MYO7A, USH2A [ENSG00000107736, ENSG00000137474, ENSG00000042781] (Usher's syndrome); GALC [ENSG00000054983] (Krabbe disease); SMPD1, NPC1, NPC2 [ENSG00000166311, ENSG00000141458, ENSG00000119655] (Niemann Pick disease); PRNP [ENSG00000171867](prion disease); SCN1A [ENSG00000144285] (Dravet syndrome); PINK1, ATP-GAP2 [ENSG00000158828] (early-onset Parkinson's disease); ATXN1, ATXN2, ATXN3, PLEKHG4, SPTBN2, CACNA1A, ATXN7, TTBK2, PPP2R2B, KCNC3, PRKCG, ITPR1, TBP, KCND1, FGF14 [ENSG00000124788, ENSG00000204842, ENSG00000066427, ENSG00000196155, ENSG00000173898, ENSG00000141837, ENSG00000163635, ENSG00000128881, ENSG00000156475, ENSG00000131398, ENSG00000126583, ENSG00000150995, ENSG00000112592, ENSG00000102057, ENSG00000102466] (spinocerebellar ataxias); SCN1A, SCN2A, CACNA1A, GRIN2B, GRIN2A, MECP2, FOXG1, SLC6A1, PRRT2, PTEN, KCNQ2, KCNQ3, STARD7, CLRN1 [ENSG00000144285, ENSG00000136531, ENSG00000141837, ENSG00000273079, ENSG00000183454, ENSG00000169057, ENSG00000176165, ENSG00000157103, ENSG00000167371, ENSG00000171862, ENSG00000075043, ENSG00000184156, ENSG00000084090, ENSG00000163646] (genetic epilepsy disorders); ATM [ENSG00000149311] (Ataxia-telangiectasia); GLB1 [ENSG00000170266] (GM1 gangliosidosis); GBA [ENSG00000177628] (Gaucher disease); GM2A [ENSG00000196743] (GM2 gangliosidosis); UBE3A [ENSG00000114062] (Angelman syndrome); SLC2A1 [ENSG00000117394] (glucose transporter deficiency type 1); LAMP2 [ENSG00000005893] (Danon disease); GLA [ENSG00000102393] (Fabry disease); PKD1, PKD2 [ENSG00000008710, ENSG00000118762] (Autosomal dominant polycystic kidney disease); GAA [ENSG00000171298] (Pompe disease); PCSK9, LDLR, APOB, APOE [ENSG00000169174, ENSG00000130164, ENSG00000084674, ENSG00000130203] (Familial hypercholesterolemia); MYOC, OPTN, TBK1, WDR36, CYPIB1 [ENSG00000034971, ENSG00000123240, ENSG00000183735, ENSG00000134987, ENSG00000138061] (Open Angle Glaucoma); IDUA [ENSG00000127415] (Hurler syndrome or Mucopolysaccharidosis 1); IDS [ENSG00000010404] (Hunter syndrome or Mucopolysaccharidosis 2); CLN3 [ENSG00000188603] (Batten disease); DMD [ENSG00000198947] (Duchenne muscular dystrophy); LMNA [ENSG00000160789] (Limb-girdle muscular dystrophy type 1B); DYSF [ENSG00000135636] (Limb-girdle muscular dystrophy type 2B); SGCA [ENSG00000108823](Limb-girdle muscular dystrophy type 2D); SGCB [ENSG00000163069] (Limb-girdle muscular dystrophy type 2E); SGCG [ENSG00000102683] (Limb-girdle muscular dystrophy type 2C); SGCD [ENSG00000170624] (Limb-girdle muscular dystrophy type 2F); DUX4 [ENSG00000260596] (Facioscapulohumeral muscular dystrophy); F9 [ENSG00000101981](Hemophilia B); F8 [ENSG00000185010] (Hemophilia A); USHA2A, RPGR, RP2, RHO, PRPF31, USH1F, PRPF3, PRPF6 [ENSG00000156313, ENSG00000102218, ENSG00000163914, ENSG00000105618, ENSG00000150275, ENSG00000117360, ENSG00000101161] (Retinitis pigmentosa); CFTR [ENSG00000001626] (cystic fibrosis); GJB2, GJB6, STRC, DFNA1, WFS1 [ENSG00000165474, ENSG00000121742, ENSG00000242866, ENSG00000131504, ENSG00000109501] (autosomal dominant hearing impairment); POU3F3 [ENSG00000198914] (nonsyndromic hearing loss).

In some embodiments, the replacement domain is codon optimized.

In addition to sequences derived from human genes, Replacement Domains can comprise sequences derived from other organisms in order to alter the stability, translation, processing, or localization of a target RNA. Examples of replacement domains derived from non-human sources include without limitation sequences that increase protein production such as those derived or isolated from Woodchuck Hepatitis Virus (WHV) Post-transcriptional Regulatory Element (WPRE), triplex from MALAT1, the PRE of Hepatitis B virus (HPRE), and an iron response element of the form CAGYCX (Y=U or A; X=U, C, or A).

Intronic Domain

In certain aspects, the RNA donor molecule described herein comprises an Intronic Domain. In some embodiments, the Intronic Domains carry binding sites that are preferentially-targeted by RNA-binding proteins with disease-causing mutations. In some embodiments, the dissociation constant of these mutated RNA-binding proteins and the Intronic Domain is lower than the dissociation constant of the non-mutated RNA-binding protein and the Intronic Domain.

RNA Motif

In some embodiments, the esnRNA molecule described herein contains an RNA motif that is complementary to the RNA donor molecule. In some embodiments of the compositions of the disclosure, the RNA motif begins at the 5' end of the esnRNA molecule. In some embodiments, at least about 3 bases, at least about 4 bases, at least about 5 bases, at least about 6 bases, at least about 7 bases, at least about 8 bases, at least about 9 bases, at least about 10 bases, at least about 11 bases, at least about 12 bases, at least about 13 bases, at least about 14 bases, at least about 15 bases, at least about 16 bases, at least about 17 bases, at least about 18 bases, at least about 19 bases, at least about 20 bases, at least about 21 bases, at least about 22 bases, at least about 23 bases, at least about 24 bases, at least about 25 bases, at least about 26 bases, at least about 27 bases, at least about 28 bases, at least about 29 bases, at least about 30 bases, at least about 31 bases, at least about 32 bases, at least about 33 bases, at least about 34 bases, at least about 35 bases, at least about 36 bases, at least about 40 bases, at least about 50 bases, at least about 60 bases, at least about 70 bases, at least about 80 bases, at least about 100 bases, or more in the esnRNA molecule are complementary to the RNA donor molecule. In some embodiments, at most about 3 bases, at most about 4 bases, at most about 5 bases, at most about 6 bases, at most about 7 bases, at most about 8 bases, at most about 9 bases, at most about 10 bases, at most about 11 bases, at most about 12 bases, at most about 13 bases, at most about 14 bases, at most about 15 bases, at most about 16 bases, at most about 17 bases, at most about 18 bases, at most about 19 bases, at most about 20 bases, at most about 21 bases, at most about 22 bases, at most about 23 bases, at most about 24 bases, at most about 25 bases, at most about 26 bases, at most about 27 bases, at most about 28 bases, at most about 29 bases, at most about 30 bases, at most about 31 bases, at most about 32 bases, at most about 33 bases, at most about 34 bases, at most about 35 bases, at most about 36 bases, at most about 40 bases, at most about 50 bases, at most about 60 bases, at most about 70 bases, at most about 80 bases, or at most about 100 bases, in the esnRNA molecule are complementary to the RNA donor molecule.

In some embodiments, the esnRNA molecule contains an RNA motif that is complementary to the RNA donor molecule that is at least about 1 nucleotide, at least about 2 nucleotides, at least about 3 nucleotides, at least about 4 nucleotides, at least about 5 nucleotides, at least about 6 nucleotides, at least about 7 nucleotides, at least about 8 nucleotides, at least about 9 nucleotides, at least about 10 nucleotides, at least about 11 nucleotides, at least about 12 nucleotides, at least about 13 nucleotides, at least about 14 nucleotides, at least about 15 nucleotides, at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 31 nucleotides, at least about 31 nucleotides, at least about 32 nucleotides, at least about 33 nucleotides, at least about 34 nucleotides, at least about 35 nucleotides, at least about 36 nucleotides, at least about 37 nucleotides, at least about 38 nucleotides, at least about 39 nucleotides, at least about 40 nucleotides, at least about 41 nucleotides, at least about 42 nucleotides, at least about 43 nucleotides, at least about 44 nucleotides, at least about 45 nucleotides, at least about 46 nucleotides, at least about 47 nucleotides, at least about 48 nucleotides, at least about 49 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 110 nucleotides, at least about 120 nucleotides, at least about 130 nucleotides, at least about 140 nucleotides, at least about 150 nucleotides, at least about 160 nucleotides, at least about 170 nucleotides, at least about 180 nucleotides, at least about 190 nucleotides, at least about 200 nucleotides, at least about 250 nucleotides, at least about 300 nucleotides, at least about 400 nucleotides, at least about 500 nucleotides, at least about more than 500 nucleotides, or any number of nucleotides in between distant from the first nucleotide of the esnRNA molecule in the 5' direction. In some embodiments, the RNA motif is at most about 1 nucleotide, at most about 2 nucleotides, at most about 3 nucleotides, at most about 4 nucleotides, at most about 5 nucleotides, at most about 6 nucleotides, at most about 7 nucleotides, at most about 8 nucleotides, at most about 9 nucleotides, at most about 10 nucleotides, at most about 11 nucleotides, at most about 12 nucleotides, at most about 13 nucleotides, at most about 14 nucleotides, at most about 15 nucleotides, at most about 16 nucleotides, at most about 17 nucleotides, at most about 18 nucleotides, at most about 19 nucleotides, at most about 20 nucleotides, at most about 21 nucleotides, at most about 22 nucleotides, at most about 23 nucleotides, at most about 24 nucleotides, at most about 25 nucleotides, at most about 26 nucleotides, at most about 27 nucleotides, at most about 28 nucleotides, at most about 29 nucleotides, at most about 30 nucleotides, at most about 31 nucleotides, at most about 31 nucleotides, at most about 32 nucleotides, at most about 33 nucleotides, at most about 34 nucleotides, at most about 35 nucleotides, at most about 36 nucleotides, at most about 37 nucleotides, at most about 38 nucleotides, at most about 39 nucleotides, at most about 40 nucleotides, at most about 41 nucleotides, at most about 42 nucleotides, at most about 43 nucleotides, at most about 44 nucleotides, at most about 45 nucleotides, at most about 46 nucleotides, at most about 47 nucleotides, at most about 48 nucleotides, at most about 49 nucleotides, at most about 50 nucleotides, at most about 55 nucleotides, at most about 60 nucleotides, at most about 65 nucleotides, at most about 70 nucleotides, at most about 75 nucleotides, at most about 80 nucleotides, at most about 85 nucleotides, at most about 90 nucleotides, at most about 95 nucleotides, at most about 100 nucleotides, at most about 110 nucleotides, at most about 120 nucleotides, at most about 130 nucleotides, at most about 140 nucleotides, at most about 150 nucleotides, at most about 160 nucleotides, at most about 170 nucleotides, at most about 180 nucleotides, at most about 190 nucleotides, at most about 200 nucleotides, at most about 250 nucleotides, at most about 300 nucleotides, at most about 400 nucleotides, at most about 500 nucleotides, at most about more than 500 nucleotides, distant from the first nucleotide of the esnRNA molecule in the 5' direction.

In some embodiments, the esnRNA molecule contains an RNA motif that is complementary to the RNA donor molecule and is selected from the group consisting of: 5'-CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3' (SEQ ID NO: 9), 5'-AGAGCTCGTTGCGA-3' (SEQ ID NO: 10), and 5'-GAGCTCGTTG-3' (SEQ ID NO: 11). In some embodiments, the RNA motif comprises 5'-CGAGCTCTCT-3' (SEQ ID NO: 1). In some embodiments, the RNA motif comprises 5'-AACGAGCTCT-3' (SEQ ID NO: 2). In some embodiments, the RNA motif comprises 5'-CGCAACGAGC-3'. (SEQ ID NO: 3) In some embodiments, the RNA motif comprises 5'-TATCGCAACG-3' (SEQ ID NO: 4). In some embodiments, the RNA motif comprises 5'-AATAATATCG-3' (SEQ ID NO: 5). In some embodiments, the RNA motif comprises 5'-TAAGAGAGCT-3' (SEQ ID NO: 6). In some embodiments, the RNA motif comprises 5'-AAGAGAGCTC-3' (SEQ ID NO: 7). In some embodiments, the RNA motif comprises 5'-AGAGAGCTCGTTGC-3' (SEQ ID NO: 8). In some embodiments, the RNA motif comprises 5'-GAGAGCTCGT-3' (SEQ ID NO: 9). In some embodiments, the RNA motif comprises 5'-AGAGCTCGTTGCGA-3' (SEQ ID NO: 10). In some embodiments, the RNA motif comprises 5'-GAGCTCGTTG-3' (SEQ ID NO: 11).

In some embodiments, the esnRNA molecule contains an RNA motif that is complementary to the RNA donor molecule that is at least about 50%, at least about 55%, at least about 60%, at least about 65%, at least about 70%, at least about 75%, at least about 80%, at least about 87%, at least about 90%, at least about 91%, at least about 92%, at least about 93%, at least about 94%, at least about 95%, at least about 96%, at least about 97%, at least about 98%, at least about 99% or any percentage in between of complementarity to the RNA donor molecule. In some embodiments, the RNA motif is at most about 50%, at most about 55%, at most about 60%, at most about 65%, at most about 70%, at most about 75%, at most about 80%, at most about 87%, at most about 90%, at most about 91%, at most about 92%, at most about 93%, at most about 94%, at most about 95%, at most about 96%, at most about 97%, at most about 98%, at most about 99% or any percentage in between of complementarity to the RNA donor molecule. In some embodiments, the RNA motif is 100% complementary to the RNA donor molecule.

In some embodiments, the esnRNA molecule and RNA donor molecule form a complex called the esnRNA-donor complex.

In some embodiments, the esnRNA-donor complex associates with a target RNA via base pairing.

UTRs

In some embodiments, the RNA donor molecule further comprises a 5' untranslated region. In some embodiments, the 5' untranslated region increases the stability of the RNA donor molecule. In some embodiments, the 5' untranslated region reduces the stability of the RNA donor molecule. In some embodiments, the 5' untranslated region alters the localization of the RNA donor molecule. In some embodiments, the 5' untranslated region alters the processing of the RNA donor molecule.

In some embodiments, the RNA donor molecule further comprises a 3' untranslated region. In some embodiments, the 3' untranslated region increases the stability of the RNA donor molecule. In some embodiments, the 3' untranslated region reduces the stability of the RNA donor molecule. In some embodiments, the 3' untranslated region alters the localization of the RNA donor molecule. In some embodiments, the 3' untranslated region alters the processing of the RNA donor molecule.

Nucleic Acid Modifications

In some embodiments, the RNA donor molecule or esnRNA is RNA, DNA, a DNA/RNA hybrid, and/or comprises at least one of a nucleic acid analog, a chemically-modified nucleic acid, or a chimera composed of two or more nucleic acids or nucleic acid analogs. As used herein, the term "nucleic acid analog" refers to a compound having structural similarity to a canonical purine or pyrimidine base occurring in DNA or RNA. The nucleic acid analog may contain a modified sugar and/or a modified nucleobase, as compared to a purine or pyrimidine base occurring naturally in DNA or RNA. In some embodiments, the nucleic acid analog is a 2'-deoxyribonucleoside, 2'-ribonucleoside, 2'-deoxyribonucleotide or a 2'-ribonucleotide, wherein the nucleobase includes a modified base (such as, for example, xanthine, uridine, oxanine (oxanosine), 7-methlguanosine, dihydrouridine, 5-methylcytidine, C3 spacer, 5-methyl dC, 5-hydroxybutynl-2'-deoxyuridine, 5-nitroindole, 5-methyl iso-deoxycytosine, iso deoxyguanosine, deoxyuradine, iso deoxycytidine, other 0-1 purine analogs, N-6-hydroxylaminopurine, nebularine, 7-deaza hypoxanthine, other 7-deazapurines, and 2-methyl purines). In some embodiments, the nucleic acid analog may be selected from the group consisting of inosine, 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In other embodiments the nucleic acid analog is a nucleic acid mimic (such as, for example, artificial nucleic acids and xeno nucleic acids (XNA).

Nucleic Acids

Also provided herein are nucleic acid sequences encoding the RNA donor molecule and esnRNA molecule disclosed herein for use in gene transfer and expression techniques described herein. It should be understood, although not always explicitly stated that the sequences provided herein can be used to provide the expression product as well as substantially identical sequences that produce a protein that has the same biological properties. These "biologically equivalent" or "biologically active" or "equivalent" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical nucleic acid sequence to the reference nucleic acid sequence when compared using sequence identity methods run under default conditions. Specific sequences are provided as examples of particular embodiments. Additionally, an equivalent polynucleotide is one that hybridizes under stringent conditions to the reference polynucleotide or its complement.

The nucleic acid sequences (e.g., polynucleotide sequences) disclosed herein may be codon-optimized. Codon optimization refers to the fact that different cells differ in their usage of particular codons. This codon bias corresponds to a bias in the relative abundance of particular tRNAs in the cell type. By altering the codons in the sequence to match with the relative abundance of corresponding tRNAs, it is possible to increase expression. It is also possible to decrease expression by deliberately choosing codons for which the corresponding tRNAs are rare in a particular cell type. Codon usage tables may be used for mammalian cells, as well as for a variety of other organisms. Based on the genetic code, nucleic acid sequences coding for various replacement domains can be generated. In some embodiments, such a sequence is optimized for expression in a host or target cell, such as a host cell used to express the RNA donor molecule containing a replacement domain in which the disclosed methods are practiced (such as in a mammalian cell, e.g., a human cell). Codon preferences and codon usage tables for a particular species can be used to engineer isolated nucleic acid molecules encoding a replacement domain (such as one encoding a protein having at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to its corresponding wild-type protein) that takes advantage of the codon usage preferences of that particular species. For example, the replacement domains disclosed herein can be designed to have codons that are preferentially used by a particular organism of interest. In one example, a replacement domain nucleic acid sequence is optimized for expression in human cells, such as one having at least about 70%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to its corresponding wild-type or originating nucleic acid sequence. In some embodiments, an isolated RNA donor molecule encoding at least one replacement domain (which can be part of a vector) includes at least one replacement domain coding sequence that is codon optimized for expression in a eukaryotic cell, or at least one replacement domain coding sequence codon optimized for expression in a human cell. In one embodiment, such a codon optimized replacement domain coding sequence has at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to its corresponding wild-type or originating sequence. In another embodiment, a eukaryotic cell codon optimized nucleic acid sequence encodes a replacement domain having at least about 80%, at least about 85%, at least about 90%, at least about 91%, at least 9 about 2%, at least about 93%, at least about 94%, at least about 95%, at least about 96%, at least about 97%, at least about 98%, at least about 99%, or 100% sequence identity to its corresponding wild-type or originating protein. In another embodiment, a variety of clones containing functionally equivalent nucleic acids may be routinely generated, such as nucleic acids which differ in sequence but which encode the same replacement domain protein sequence. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3.sup.rd Edition, W.H.5 Freeman and Co., NY).

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10× SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC;

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences described herein.

Promoters

In some embodiments of the compositions of the disclosure, the sequence encoding the RNA donor molecule further comprises a sequence encoding a promoter capable of expressing the RNA donor molecule in a eukaryotic cell.

In some embodiments of the compositions of the disclosure, the sequence encoding the engineered small nuclear RNA molecule further comprises a sequence encoding a promoter capable of expressing the engineered small nuclear RNA molecule in a eukaryotic cell.

Vectors

In some embodiments of the compositions and methods of the disclosure, a vector of the disclosure is a viral vector. In some embodiments, the viral vector comprises a sequence isolated or derived from a retrovirus. In some embodiments, the viral vector comprises a sequence isolated or derived from a lentivirus. In some embodiments, the viral vector comprises a sequence isolated or derived from an adenovirus. In some embodiments, the viral vector comprises a sequence isolated or derived from an adeno-associated virus (AAV). In some embodiments, the viral vector is replication incompetent. In some embodiments, the viral vector is isolated or recombinant. In some embodiments, the viral vector is self-complementary.

In some embodiments of the compositions and methods of the disclosure, the viral vector comprises a sequence isolated or derived from an adeno-associated virus (AAV). In some embodiments, the viral vector comprises an inverted terminal repeat sequence or a capsid sequence that is isolated or derived from an AAV of serotype AAV1, AAV2, AAV3, AAV4, AAV5, AAV6, AAV7, AAV8, AAV9, AAV10, AAV11 or AAV12. In some embodiments, the viral vector is replication incompetent. In some embodiments, the viral vector is isolated or recombinant (rAAV). In some embodiments, the viral vector is self-complementary (scAAV).

In some embodiments of the compositions and methods of the disclosure, a vector of the disclosure is a non-viral vector. In some embodiments, the vector comprises or consists of a nanoparticle, a micelle, a liposome or lipoplex, a polymersome, a polyplex, an exosome or a dendrimer. In some embodiments, the vector is an expression vector or recombinant expression system. As used herein, the term "recombinant expression system" refers to a genetic construct for the expression of certain genetic material formed by recombination.

In some embodiments of the compositions and methods of the disclosure, an expression vector, viral vector or non-viral vector provided herein, includes without limitation, an expression control element. An "expression control element" as used herein refers to any sequence that regulates the expression of a coding sequence, such as a gene. Examples of expression control elements include but are not limited to promoters, enhancers, microRNAs, post-transcriptional regulatory elements, polyadenylation signal sequences, 5' or 3' untranslated regions, and introns.

Expression control elements may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. In some embodiments, expression control by a promoter is tissue-specific. Non-limiting examples of promoters include CMV, CBA, CAG, Cbh, EF-1a, PGK, UBC, GUSB, UCOE, hAAT, TBG, Desmin, MCK, C5-12, NSE, Synapsin, PDGF, MecP2, CaMKII, mGluR2, NFL, NFH, nβ2, PPE, ENK, EAAT2, GFAP, MBP, H1 and U6 promoters. In some embodiments, the promoter is a sequence isolated or derived from a promoter capable of driving expression of a transfer RNA (tRNA). In some embodiments, the promoter is isolated or derived from an alanine tRNA promoter, an arginine tRNA promoter, an asparagine tRNA promoter, an aspartic acid tRNA promoter, a cysteine tRNA promoter, a glutamine tRNA promoter, a glutamic acid tRNA promoter, a glycine tRNA promoter, a histidine tRNA promoter, an isoleucine tRNA promoter, a leucine tRNA promoter, a lysine tRNA promoter, a methionine tRNA promoter, a phenylalanine tRNA promoter, a proline tRNA promoter, a serine tRNA promoter, a threonine tRNA promoter, a tryptophan tRNA promoter, a tyrosine tRNA promoter, or a valine tRNA promoter. In some embodiments, the promoter is isolated or derived from a valine tRNA promoter.

In some embodiments of the compositions of the disclosure, the eukaryotic cell is an animal cell. In some embodiments, the animal cell is a mammalian cell. In some embodiments, the animal cell is a human cell.

An "enhancer" is a region of DNA that can be bound by activating proteins to increase the likelihood or frequency of transcription. Non-limiting examples of enhancers and post-transcriptional regulatory elements include the CMV enhancer and WPRE.

In some embodiments of the compositions and methods of the disclosure, an expression vector, viral vector or non-viral vector provided herein, includes without limitation, vector elements such as an IRES or 2A peptide sites for configuration of "multicistronic" or "polycistronic" or "bicistronic" or tricistronic" constructs, i.e., having double or triple or multiple coding areas or exons, and as such will have the capability to express from mRNA two or more proteins from a single construct. Multicistronic vectors simultaneously express two or more separate proteins from the same mRNA. The two strategies most widely used for constructing multicistronic configurations are through the use of an IRES or a 2A self-cleaving site. An "IRES" refers to an internal ribosome entry site or portion thereof of viral, prokaryotic, or eukaryotic origin which are used within polycistronic vector constructs. In some embodiments, an IRES is an RNA element that allows for translation initiation in a cap-independent manner. The term "self-cleaving peptides" or "sequences encoding self-cleaving peptides" or "2A self-cleaving site" refer to linking sequences which are used within vector constructs to incorporate sites to promote ribosomal skipping and thus to generate two polypeptides from a single promoter, such self-cleaving peptides include without limitation, T2A, and P2A peptides or sequences encoding the self-cleaving peptides.

In some embodiments, the vector is a viral vector. In some embodiments, the vector is an adenoviral vector, an adeno-associated viral (AAV) vector, or a lentiviral vector. In some embodiments, the vector is a retroviral vector, an adenoviral/retroviral chimera vector, a herpes simplex viral I or II vector, a parvoviral vector, a reticuloendotheliosis viral vector, a poliovirval vector, a papillomaviral vector, a vaccinia viral vector, or any hybrid or chimeric vector incorporating favorable aspects of two or more viral vectors. In some embodiments, the vector further comprises one or more expression control elements operably linked to the polynucleotide. In some embodiments, the vector further comprises one or more selectable markers. In some embodiments, the AAV vector has low toxicity. In some embodiments, the AAV vector does not incorporate into the host genome, thereby having a low probability of causing insertional mutagenesis. In some embodiments, the AAV vector can encode a range of total polynucleotides from 0.3 kb to 4.75 kb. In some embodiments, examples of AAV vectors that may be used in any of the herein described compositions, systems, methods, and kits can include an AAV1 vector, a modified AAV1 vector, an AAV2 vector, a modified AAV2 vector, an AAV3 vector, a modified AAV3 vector, an AAV4 vector, a modified AAV4 vector, an AAV5 vector, a modified AAV5 vector, an AAV6 vector, a modified AAV6 vector, an AAV7 vector, a modified AAV7 vector, an AAV8 vector, an AAV9 vector, an AAV.rh10 vector, a modified AAV.rh10 vector, an AAV.rh32/33 vector, a modified AAV.rh32/33 vector, an AAV.rh43 vector, a modified AAV.rh43 vector, an AAV.rh74 vector, a modified AAV.rh74 vector, an AAV.rh64R1 vector, and a modified AAV.rh64R1 vector and any combinations or equivalents thereof. In some embodiments, the lentiviral vector is an integrase-competent lentiviral vector (ICLV). In some embodiments, the lentiviral vector can refer to the transgene plasmid vector as well as the transgene plasmid vector in conjunction with related plasmids (e.g., a packaging plasmid, a rev expressing plasmid, an envelope plasmid) as well as a lentiviral-based particle capable of introducing exogenous nucleic acid into a cell through a viral or viral-like entry mechanism. In some embodiments, examples of lentiviral vectors that may be used in any of the herein described compositions, systems, methods, and kits can include a human immunodeficiency virus (HIV) 1 vector, a modified human immunodeficiency virus (HIV) 1 vector, a human immunodeficiency virus (HIV) 2 vector, a modified human immunodeficiency virus (HIV) 2 vector, a sooty mangabey simian immunodeficiency virus (SIVSM) vector, a modified sooty mangabey simian immunodeficiency virus (SIVSM) vector, a African green monkey simian immunodeficiency virus (SIVAGM) vector, a modified African green monkey simian immunodeficiency virus (SIVAGM) vector, an equine infectious anemia virus (EIAV) vector, a modified equine infectious anemia virus (EIAV) vector, a feline immunodeficiency virus (FIV) vector, a modified feline immunodeficiency virus (FIV) vector, a Visna/maedi virus (VNV/VMV) vector, a modified Visna/maedi virus (VNV/VMV) vector, a caprine arthritis-encephalitis virus (CAEV) vector, a modified caprine arthritis-encephalitis virus (CAEV) vector, a bovine immunodeficiency virus (BIV), or a modified bovine immunodeficiency virus (BIV).

In some embodiments of the compositions and methods of the disclosure, a vector comprises or encodes an RNA donor molecule and an esnRNA molecule. In some embodiments, the vector comprises or encodes at least RNA donor molecule and an esnRNA molecule. In some embodiments, the vector comprises or encodes one or more RNA donor molecule(s) and esnRNA molecule(s) of the disclosure. In some embodiments, the vector comprises or encodes two or more RNA donor molecules and esnRNA molecules of the disclosure. In some embodiments of the compositions and methods of the disclosure, a vector comprises or encodes an RNA donor molecule. In some embodiments, the vector comprises or encodes at least RNA donor molecule. In some embodiments, the vector comprises or encodes one or more RNA donor molecule(s). In some embodiments, the vector comprises or encodes two or more RNA donor molecules.

In some embodiments of the compositions and methods of the disclosure, a vector of the disclosure is a viral vector. In some embodiments, the viral vector comprises a sequence isolated or derived from a retrovirus. In some embodiments, the viral vector comprises a sequence isolated or derived from a lentivirus. In some embodiments, the viral vector comprises a sequence isolated or derived from an adenovirus. In some embodiments, the viral vector comprises a sequence isolated or derived from an adeno-associated virus (AAV). In some embodiments, the viral vector is replication incompetent. In some embodiments, the viral vector is isolated or recombinant. In some embodiments, the viral vector is self-complementary.

In some embodiments of the compositions and methods of the disclosure, the viral vector comprises a sequence isolated or derived from an adeno-associated virus (AAV). In some embodiments, the viral vector comprises an inverted terminal repeat sequence or a capsid sequence that is isolated or derived from an AAV of serotype AAV1, AAV2, AAV3, AAV4, AAV5, AAV6, AAV7, AAV8, AAV9, AAV10, AAV11 or AAV12. In some embodiments, the viral vector is replication incompetent. In some embodiments, the viral vector is isolated or recombinant (rAAV). In some embodiments, the viral vector is self-complementary (scAAV).

In some embodiments of the compositions and methods of the disclosure, a vector of the disclosure is a non-viral vector. In some embodiments, the vector comprises or consists of a nanoparticle, a micelle, a liposome or lipoplex, a polymersome, a polyplex or a dendrimer. In some embodiments, the vector is an expression vector or recombinant expression system. As used herein, the term"recombinant expression system" refers to a genetic construct for the expression of certain genetic material formed by recombination.

In some embodiments, the liposome, lipoplex, or nanoparticle can further comprise a non-cationic lipid, a PEG conjugated lipid, a sterol, or any combination thereof.

In some embodiments, the liposome, lipoplex, or nanoparticle further comprises a non-cationic lipid, wherein the non-ionic lipid is selected from the group consisting of distearoyl-sn-glycero-phosphoethanolamine, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dieru-coylphosphatidylcholine (DEPC), palmitoyloleyolphosphatidylglycerol (POPG), dielaidoyl-phosphatidylethanolamine (DEPE), lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid,cerebrosides, dicetylphosphate, lysophosphatidylcholine, dilinoleoylphosphatidylcholine and non-cationic lipids described, for example, in WO2017/099823 or US2018/0028664.

In some embodiments, the liposome, lipoplex, or nanoparticle further comprises a conjugated lipid, wherein the conjugated lipid, wherein the conjugated-lipid is selected from the group consisting of PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-0-(2',3'-di(tetradecanoyloxy)propyl-1-0-(w-methoxy(polyethoxy)ethyl) butanedioate (PEG-S-DMG)), PEG dialkoxypropylcarbam, N-(carbonyl-methoxypoly ethylene glycol 2000)-1,2-distearoyl-sn-glycero-3-phosphoethanolamine sodium salt.

In some embodiments, the liposome, lipoplex, or nanoparticle further comprises cholesterol or a cholesterol derivative.

In some embodiments, the liposome, lipoplex, or nanoparticle further comprises an ionizable lipid, a non-cationic lipid, a conjugated lipid that inhibits aggregation of particles, and a sterol. The amount of the ionizable lipid, the non-cationic lipid, the conjugated lipid that inhibits aggregation of particles, and the sterol can be varied independently. In some embodiments, the lipid nanoparticle comprises an ionizable lipid in an amount from about 20 mol % to about 90 mol % of the total lipid present in the particle, a non-cationic lipid in an amount from about 5 mol % to about 30 mol % of the total lipid present in the particle, a conjugated lipid that inhibits aggregation of particles in an amount from about 0.5 mol % to about 20 mol % of the total lipid present in the particle, and a sterol in an amount from about 20 mol % to about 50 mol % of the total lipid present in the particle.

The ratio of total lipid to DNA vector can be varied as desired. For example, the total lipid to DNA vector (mass or weight) ratio can be from about 10:1 to about 30:1.

In some embodiments of the compositions and methods of the disclosure, an expression vector, viral vector or non-viral vector provided herein, includes without limitation, an expression control element. An "expression control element" as used herein refers to any sequence that regulates the expression of a coding sequence, such as a gene. Examples of expression control elements include but are not limited to promoters, enhancers, microRNAs, post-transcriptional regulatory elements, polyadenylation signal sequences, and introns. Expression control elements may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. In some embodiments, expression control by a promoter is tissue-specific. Non-limiting examples of promoters include CMV, CBA, CAG, Cbh, EF-1a, PGK, UBC, GUSB, UCOE, hAAT, TBG, Desmin, MCK, C5-12, NSE, Synapsin, PDGF, MecP2, CaMKII, mGluR2, NFL, NFH, nβ2, PPE, ENK, EAAT2, GFAP, MBP, and U6 promoters. An "enhancer" is a region of DNA that can be bound by activating proteins to increase the likelihood or frequency of transcription. Non-limiting examples of enhancers and posttranscriptional regulatory elements include the CMV enhancer and WPRE.

Cells and Tissues

In some embodiments of the compositions and methods of the disclosure, a cell of the disclosure is a eukaryotic cell. In some embodiments, the cell is a mammalian cell. In some embodiments, the cell is a bovine, murine, feline, equine, porcine, canine, simian, or human cell. In some embodiments, the cell is a non-human mammalian cell such as a non-human primate cell. In some embodiments, a cell of the disclosure is a somatic cell. In some embodiments, a cell of the disclosure is a germline cell. In some embodiments, a germline cell of the disclosure is not a human cell.

In some embodiments of the compositions and methods of the disclosure, a cell of the disclosure is a stem cell. In some embodiments, a cell of the disclosure is an embryonic stem cell. In some embodiments, an embryonic stem cell of the disclosure is not a human cell. In some embodiments, a cell of the disclosure is a multipotent stem cell or a pluripotent stem cell. In some embodiments, a cell of the disclosure is an adult stem cell. In some embodiments, a cell of the disclosure is an induced pluripotent stem cell (iPSC). In some embodiments, a cell of the disclosure is a hematopoietic stem cell (HSC).

In some embodiments of the compositions and methods of the disclosure, an immune cell of the disclosure is a lymphocyte. In some embodiments, an immune cell of the disclosure is a T lymphocyte (also referred to herein as a T-cell). Examples of T-cells of the disclosure include, but are not limited to, naïve T cells, effector T cells, helper T cells, memory T cells, regulatory T cells (Tregs) and Gamma delta T cells. In some embodiments, an immune cell of the disclosure is a B lymphocyte. In some embodiments, an immune cell of the disclosure is a natural killer cell. In some embodiments, an immune cell of the disclosure is an antigen-presenting cell.

In some embodiments of the compositions and methods of the disclosure, a muscle cell of the disclosure is a myoblast or a myocyte. In some embodiments, a muscle cell of the disclosure is a cardiac muscle cell, skeletal muscle cell or smooth muscle cell. In some embodiments, a muscle cell of the disclosure is a striated cell.

In some embodiments of the compositions and methods of the disclosure, a somatic cell of the disclosure is an epithelial cell. In some embodiments, an epithelial cell of the disclosure forms a squamous cell epithelium, a cuboidal cell epithelium, a columnar cell epithelium, a stratified cell epithelium, a pseudostratified columnar cell epithelium or a transitional cell epithelium. In some embodiments, an epithelial cell of the disclosure forms a gland including, but not limited to, a pineal gland, a thymus gland, a pituitary gland, a thyroid gland, an adrenal gland, an apocrine gland, a holocrine gland, a merocrine gland, a serous gland, a mucous gland and a sebaceous gland. In some embodiments, an epithelial cell of the disclosure contacts an outer surface of an organ including, but not limited to, a lung, a spleen, a stomach, a pancreas, a bladder, an intestine, a kidney, a gallbladder, a liver, a larynx or a pharynx. In some embodiments, an epithelial cell of the disclosure contacts an outer surface of a blood vessel or a vein.

In some embodiments of the compositions and methods of the disclosure, a brain cell of the disclosure is a neuronal cell. In some embodiments, a neuron cell of the disclosure is a neuron of the central nervous system. In some embodiments, a neuron cell of the disclosure is a neuron of the brain or the spinal cord. In some embodiments, a neuron cell of the disclosure is a neuron of a cranial nerve or an optic nerve. In some embodiments, a neuron cell of the disclosure is a neuron of the peripheral nervous system. In some embodiments, a neuron cell of the disclosure is a neuroglial or a glial cell. In some embodiments, a glial of the disclosure is a glial cell of the central nervous system including, but not limited to, oligodendrocytes, astrocytes, ependymal cells, and microglia. In some embodiments, a glial of the disclosure is a glial cell of the peripheral nervous system including, but not limited to, Schwann cells and satellite cells.

In some embodiments of the compositions and methods of the disclosure, a liver cell of the disclosure is a hepatocytes. In some embodiments, a liver cell of the disclosure is a hepatic stellate cell. In some embodiments, a liver cell of the disclosure is a Kupffer cell. In some embodiments, a liver cell of the disclosure is a sinusoidal endothelial cells.

In some embodiments of the compositions and methods of the disclosure, a retinal cell of the disclosure is a photoreceptor. In some embodiments, a photoreceptor cell of the disclosure is a rod. In some embodiments, a retinal cell of the disclosure is a cone. In some embodiments, a retinal cell of the disclosure is a bipolar cell. In some embodiments, a retinal cell of the disclosure is a ganglion cell. In some embodiments, a retinal cell of the disclosure is a horizontal cell. In some embodiments, a retinal cell of the disclosure is an amacrine cell.

In some embodiments of the compositions and methods of the disclosure, a heart cell of the disclosure is a cardiomyocyte. In some embodiments, a heart cell of the disclosure is a cardiac pacemaker cell.

In some embodiments of the compositions and methods of the disclosure, a somatic cell of the disclosure is a primary cell.

In some embodiments of the compositions and methods of the disclosure, a somatic cell of the disclosure is a cultured cell.

In some embodiments of the compositions and methods of the disclosure, a somatic cell of the disclosure is in vivo, in vitro, ex vivo or in situ.

In some embodiments of the compositions and methods of the disclosure, a somatic cell of the disclosure is autologous or allogeneic.

Methods of Use

In some embodiments, described herein are compositions comprising two RNA molecules (an RNA donor and an engineered small nuclear RNA or esnRNA) where the RNA donor selectively binds a target RNA molecule while the esnRNA binds the RNA donor molecule and promotes a trans-splicing reaction with the target RNA molecule. In certain aspects, described herein is a non-natural esnRNA molecule that targets a non-natural RNA donor molecule that increases the recognition of the RNA donor molecule by the endogenous spliceosome. The disclosure provides vectors, compositions and cells comprising or encoding the RNA donor molecule and the esnRNA molecule. The disclosure provides methods of using the RNA donor molecule and the esnRNA molecule, vectors, compositions and cells of the disclosure to treat a disease or disorder.

Without being bound by theory, the combination of a trans-splicing RNA donor molecule and a esnRNA that contacts the RNA donor molecule results in replacement of chosen sequences within a target RNA in a manner that is sufficiently efficient to replace disease-causing RNA sequences in human cells to address disease. In some embodiments, the disclosure provides compositions and methods for targeting disease-causing RNA molecules in a sequence-specific manner and replacing disease-causing RNA sequences within these RNA molecules with high efficiency. In some embodiments, the RNA donor molecule and esnRNA implementations show utility in a variety of contexts including replacement of disease-causing sequences or insertion of engineered sequences into Target RNAs. In some embodiments, the engineered sequences can alter the translation or stability of Target RNAs to increase or decrease protein production or Target RNA levels. In some embodiments, this disclosure provides vectors, compositions and cells comprising or encoding RNA donor molecule and esnRNA molecule and methods of using the trans-splicing RNA compositions.

In some embodiments, described herein is a RNA donor molecule comprising four domains. In some embodiments, the combination of four domains in the RNA donor molecule results in replacement of chosen sequences within a target RNA in a manner that is sufficiently efficient to replace disease-causing RNA sequences in human cells to address disease. In some embodiments, the disclosure provides compositions and methods for targeting disease-causing RNA molecules in a sequence-specific manner and replacing disease-causing RNA sequences within this RNA molecules with high efficiency. In some embodiments, the RNA donor molecule implementations show utility in a variety of contexts including replacement of disease-causing sequences or insertion of engineered sequences into Target RNAs. In some embodiments, the engineered sequences can alter the translation or stability of Target RNAs to increase or decrease protein production or Target RNA levels. In some embodiments, this disclosure provides vectors, compositions and cells comprising or encoding RNA donor molecule and methods of using the trans-splicing RNA compositions.

Figure 1B:
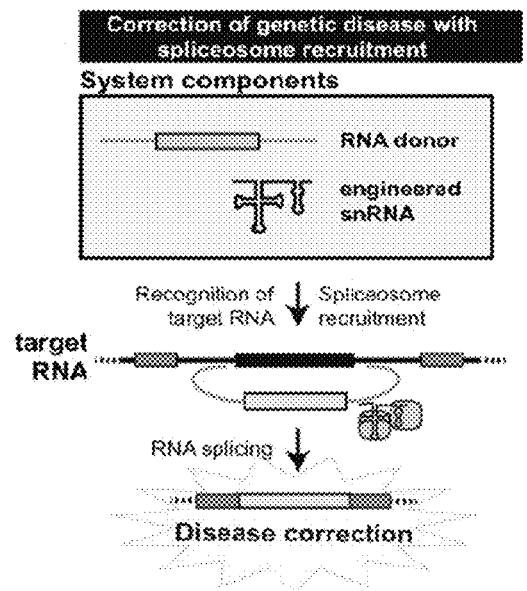
Figure 1C:
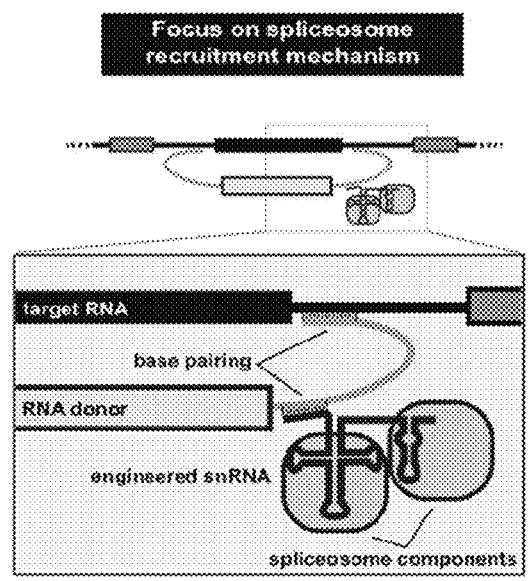

In some embodiments, a esnRNA and RNA donor are used to correct a genetic disease as illustrated in FIGS. 1A-1C. In some embodiments, the RNA donor hybridizes to the target RNA carrying a mutation. In some embodiments, base pairing among the RNA donor and target RNA bring these molecule in close proximity. In some embodiments, b pairing among the esnRNA and the RNA donor brings spliceosome components in close proximity which promotes a trans-splicing reaction among the target RNA and the RNA donor. In some embodiments, the esnRNA contacts the RNA donor. In some embodiments, contacting the RNA donor with the esnRNA results in recruitment of spliceosome components. In some embodiments, trans-splicing occurs between the RNA donor molecule and the target RNA, resulting in a corrected target RNA with the RNA donor molecule replacing a chosen sequence in the target RNA.

Figure 2A:
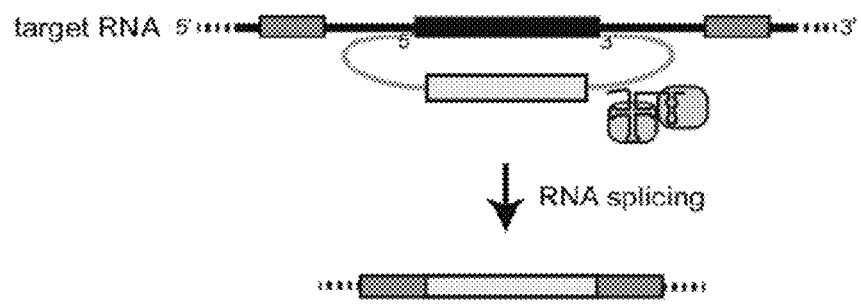
FIGS. 2A-2B illustrate two non-limiting embodiments.
Figure 2B:
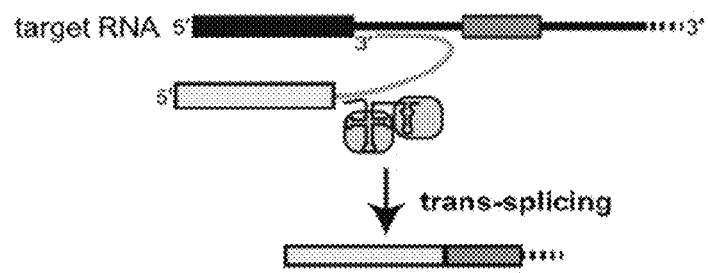

In some embodiments, the compositions described herein can edit internal sequences of a target RNA. An example is depicted in FIG. 2A. In one embodiments, a RNA donor and a esnRNA edit an internal sequence. In some embodiments, the compositions described herein can edit terminal portions of the target sequence. An example is depicted in FIG. 2B.

In some embodiments, described herein is a method of modifying the sequence of an RNA molecule or a protein encoded by the RNA molecule comprising contacting the composition and the RNA molecule under conditions suitable for binding and trans-splicing of one or more of the RNA donor molecules (or a portion thereof) to the RNA molecule.

The disclosure provides a method of modifying an activity of a protein encoded by an RNA molecule comprising contacting the composition and the RNA molecule under conditions suitable for binding and trans-splicing of one or more of the RNA donor molecules (or a portion thereof) to the RNA molecule.

The disclosure provides a method of modifying the sequence of an RNA molecule or a protein encoded by the RNA molecule with at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95, or 100% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at most about 15%, at most about 20%, at most about 25%, at most about 30%, at most about 35%, at most about 40%, at most about 45%, at most about 50%, at most about 55%, at most about 60%, at most about 65%, at most about 70%, at most about 75%, at most about 80%, at most about 85%, at most about 90%, at most about 95, or 100% efficiency comprising contacting the composition and the RNA molecule under conditions suitable for binding and trans-splicing of one or more of the RNA donor molecules (or a portion thereof) to the RNA molecule.

In some embodiments, the methods comprise modifying the sequence of an RNA molecule or a protein encoded by the RNA molecule with at least about 15% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at least about 20% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at least about 30% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at least about 40% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at least about 50% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at least about 60% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at least about 70% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at least about 80% efficiency comprising contacting the composition and the RNA molecule under conditions suitable for binding and trans-splicing of one or more of the RNA donor molecules (or a portion thereof) to the RNA molecule. In some embodiments, the methods comprise modifying the sequence of an RNA molecule or a protein encoded by the RNA molecule with at least about 90% efficiency comprising contacting the composition and the RNA molecule under conditions suitable for binding and trans-splicing of one or more of the RNA donor molecules (or a portion thereof) to the RNA molecule.

The disclosure provides a method of modifying the sequence of an untranslated region of an RNA molecule comprising contacting the composition and the RNA molecule under conditions suitable for binding and trans-splicing of one or more of the RNA donor molecules (or a portion thereof) to the RNA molecule.

The disclosure provides a method of increasing the expression of an RNA by insertion of WPRE or sequences with similar activity comprising contacting the composition and the RNA molecule under conditions suitable for binding and trans-splicing of one or more of the RNA donor molecules (or a portion thereof) to the RNA molecule.

The disclosure provides a method of modifying the composition of a protein encoded by a target RNA comprising contacting the composition and a cell comprising the target RNA under conditions suitable for trans-splicing among the composition and the target RNA.

The disclosure provides a method of modifying the composition of a target RNA with efficiency at least about 20%, wherein 100% efficiency constitutes complete replacement of a chosen sequence within the target RNA comprising contacting the composition and a cell comprising the target RNA under conditions suitable for trans-splicing among the composition and the target RNA. In some embodiments, the efficiency is at least about 20%, at least about 25%, at least about 30%, at least about 35%, at least about 40%, at least about 45%, at least about 50%, at least about 55%, at least about 60%, at least about 65%, at least about 70%, at least about 75%, at least about 89%, at least about %, at least about 85%, at least about 90%, at least about 95%, or 100%. In some embodiments, the efficiency is at most about 20%, at most about 25%, at most about 30%, at most about 35%, at most about 40%, at most about 45%, at most about 50%, at most about 55%, at most about 60%, at most about 65%, at most about 70%, at most about 75%, at most about 89%, at most about %, at most about 85%, at most about 90%, at most about 95%, or 100%. In some embodiments, the efficiency is at least about 20%. In some embodiments, the efficiency is at least about 40%. In some embodiments, the efficiency is at least about 60%. In some embodiments, the efficiency is at least about 70%. In some embodiments, the efficiency is at least about 80%. In some embodiments, the efficiency is at least about 90%. In some embodiments, the efficiency is about 100%.

As described herein is a method of modifying the composition of a protein encoded by a target RNA with efficiency at least about 20%, wherein 100% efficiency constitutes complete replacement of a chosen sequence within the Target RNA comprising contacting the composition and a cell comprising the target RNA under conditions suitable for trans-splicing among the composition and the target RNA. In some embodiments, the efficiency is at least about 20%, at least about 25%, at least about 30%, at least about 35%, at least about 40%, at least about 45%, at least about 50%, at least about 55%, at least about 60%, at least about 65%, at least about 70%, at least about 75%, at least about 89%, at least about %, at least about 85%, at least about 90%, at least about 95%, or 100%. In some embodiments, the efficiency is at most about 20%, at most about 25%, at most about 30%, at most about 35%, at most about 40%, at most about 45%, at most about 50%, at most about 55%, at most about 60%, at most about 65%, at most about 70%, at most about 75%, at most about 89%, at most about %, at most about 85%, at most about 90%, at most about 95%, or 100%. In some embodiments, the efficiency is at least about 20%. In some embodiments, the efficiency is at least about 40%. In some embodiments, the efficiency is at least about 60%. In some embodiments, the efficiency is at least about 70%. In some embodiments, the efficiency is at least about 80%. In some embodiments, the efficiency is at least about 90%. In some embodiments, the efficiency is about 100%.

The disclosure provides a method of modifying the composition of a target RNA with high efficiency comprising contacting the composition and a cell comprising the target RNA under conditions suitable for trans-splicing among the composition and the target RNA. In some embodiments, the cell is in vivo, in vitro, ex vivo or in situ. In some embodiments, the composition comprises a vector comprising or encoding a RNA donor molecule of the disclosure. In some embodiments, the composition comprises a vector comprising or encoding an RNA donor molecule and an esnRNA of the disclosure. In some embodiments, the vector is an AAV.

The disclosure provides a method of modifying the composition of a protein encoded by a target RNA with high efficiency comprising contacting the composition and a cell comprising the target RNA under conditions suitable for trans-splicing among the composition and the target RNA. In some embodiments, the cell is in vivo, in vitro, ex vivo or in situ. In some embodiments, the composition comprises a vector comprising or encoding an RNA donor molecule of the disclosure. In some embodiments, the composition comprises a vector comprising or encoding an RNA donor molecule and an esnRNA molecule of the disclosure. In some embodiments, the vector is an AAV.

The disclosure provides a method of treating a disease or disorder comprising administering to a subject a therapeutically effective amount of a composition of the disclosure.

The disclosure provides a method of treating a disease or disorder comprising administering to a subject a therapeutically effective amount of a composition of the disclosure, wherein the composition comprises a vector comprising or encoding an RNA donor molecule of the disclosure, and wherein the composition modifies a level of expression of an RNA molecule of the disclosure or a protein encoded by the RNA molecule.

The disclosure provides a method of treating a disease or disorder comprising administering to a subject a therapeutically effective amount of a composition of the disclosure, wherein the composition comprises a vector comprising or encoding an RNA donor molecule and esnRNA molecule of the disclosure, and wherein the composition modifies a level of expression of an RNA molecule of the disclosure or a protein encoded by the RNA molecule.

The disclosure provides a method of treating a disease or disorder comprising administering to a subject a therapeutically effective amount of a composition of the disclosure, wherein the composition comprises a vector comprising or encoding an RNA donor molecule of the disclosure and wherein the composition modifies an activity of a protein encoded by an RNA molecule.

The disclosure provides a method of treating a disease or disorder comprising administering to a subject a therapeutically effective amount of a composition of the disclosure, wherein the composition comprises a vector comprising or encoding an RNA donor molecule and an esnRNA molecule of the disclosure and wherein the composition modifies an activity of a protein encoded by an RNA molecule.

In some embodiments of the compositions and methods of the disclosure, a disease or disorder of the disclosure includes, but is not limited to, a genetic disease or disorder. In some embodiments, the genetic disease or disorder is a single-gene disease or disorder. In some embodiments, the single-gene disease or disorder is an autosomal dominant disease or disorder, an autosomal recessive disease or disorder, an X-chromosome linked (X-linked) disease or disorder, an X-linked dominant disease or disorder, an X-linked recessive disease or disorder, a Y-linked disease or disorder or a mitochondrial disease or disorder. In some embodiments, the singe-gene disease or disorder is, but not limited to, common variable immune deficiency, Adenosine deaminase deficiency, X-linked severe combined immunodeficiency, Beta-thassalemia, alpha-thassalemia, myelodysplastic syndrome, Amyotrophic lateral sclerosis, Frontotemporal dementia with parkinsonism, Usher's syndrome, Krabbe disease, Niemann Pick disease, prion disease, Dravet syndrome, early-onset Parkinson's disease, spinocerebellar ataxias, genetic epilepsy disorders, Ataxia-telangiectasia, GM1 gangliosidosis, Gaucher disease, GM2 gangliosidosis, Angelman syndrome, glucose transporter deficiency type 1, Danon disease, Fabry disease, Autosomal dominant polycystic kidney disease, Pompe disease, Familial hypercholesterolemia, Open Angle Glaucoma, Hurler syndrome or Mucopolysaccharidosis 1, Hunter syndrome or Mucopolysaccharidosis 2, Batten disease, Duchenne muscular dystrophy, Limb-girdle muscular dystrophy type 1B, Limb-girdle muscular dystrophy type 2B, Limb-girdle muscular dystrophy type 2D, Limb-girdle muscular dystrophy type 2E, Limb-girdle muscular dystrophy type 2C, Limb-girdle muscular dystrophy type 2F, Facioscapulohumeral muscular dystrophy, Hemophilia B, Hemophilia A, Retinitis pigmentosa, cystic fibrosis, autosomal dominant hearing impairment, and non-syndromic hearing loss. In some embodiments, the genetic disease or disorder is a multiple-gene disease or disorder. In some embodiments, the genetic disease or disorder is a multiple-gene disease or disorder. In some embodiments, the single-gene disease or disorder is an autosomal dominant disease or disorder including, but not limited to, Huntington's disease, neurofibromatosis type 1, neurofibromatosis type 2, Marfan syndrome, hereditary non-polyposis colorectal cancer, hereditary multiple exostoses, Von Willebrand disease, and acute intermittent *porphyria*. In some embodiments, the single-gene disease or disorder is an autosomal recessive disease or disorder including, but not limited to, Albinism, Medium-chain acyl-CoA dehydrogenase deficiency, cystic fibrosis, sickle-cell disease, Tay-Sachs disease, Niemann-Pick disease, spinal muscular atrophy, and Roberts syndrome. In some embodiments, the single-gene disease or disorder is X-linked disease or disorder including, but not limited to, muscular dystrophy, Duchenne muscular dystrophy, Hemophilia, Adrenoleukodystrophy (ALD), Rett syndrome, and Hemophilia A. In some embodiments, the single-gene disease or disorder is a mitochondrial disorder including, but not limited to, Leber's hereditary optic neuropathy.

In some embodiments of the compositions and methods of the disclosure, a disease or disorder of the disclosure includes, but is not limited to, an immune disease or disorder. In some embodiments, the immune disease or disorder is an immunodeficiency disease or disorder including, but not limited to, B-cell deficiency, T-cell deficiency, neutropenia, asplenia, complement deficiency, acquired immunodeficiency syndrome (AIDS) and immunodeficiency due to medical intervention (immunosuppression as an intended or adverse effect of a medical therapy). In some embodiments, the immune disease or disorder is an autoimmune disease or disorder including, but not limited to, Achalasia, Addison's disease, Adult Still's disease, Agammaglobulinemia, Alopecia areata, Amyloidosis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease, or Wegener's granulomatosis.

In some embodiments of the compositions and methods of the disclosure, a disease or disorder of the disclosure includes, but is not limited to, an inflammatory disease or disorder.

In some embodiments of the compositions and methods of the disclosure, a disease or disorder of the disclosure includes, but is not limited to, a metabolic disease or disorder.

In some embodiments of the compositions and methods of the disclosure, a disease or disorder of the disclosure includes, but is not limited to, a degenerative or a progressive disease or disorder. In some embodiments, the degenerative or a progressive disease or disorder includes, but is not limited to, amyotrophic lateral sclerosis (ALS), Huntington's disease, Alzheimer's disease, and aging.

In some embodiments of the compositions and methods of the disclosure, a disease or disorder of the disclosure includes, but is not limited to, an infectious disease or disorder.

In some embodiments of the compositions and methods of the disclosure, a disease or disorder of the disclosure includes, but is not limited to, a pediatric or a developmental disease or disorder.

In some embodiments of the compositions and methods of the disclosure, a disease or disorder of the disclosure includes, but is not limited to, a cardiovascular disease or disorder.

In some embodiments of the compositions and methods of the disclosure, a disease or disorder of the disclosure includes, but is not limited to, a proliferative disease or disorder. In some embodiments, the proliferative disease or disorder is a cancer. In some embodiments, the cancer includes, but is not limited to, Acute Lymphoblastic Leukemia (ALL), Acute Myeloid Leukemia (AML), Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Appendix Cancer, Gastrointestinal Carcinoid Tumors, Astrocytomas, Atypical Teratoid/Rhabdoid Tumor, Central Nervous System (Brain Cancer), Basal Cell Carcinoma, Bile Duct Cancer, Bladder Cancer, Bone Cancer, Ewing Sarcoma, Osteosarcoma, Malignant Fibrous Histiocytoma, Brain Tumors, Breast Cancer, Burkitt Lymphoma, Carcinoid Tumor, Carcinoma, Cardiac (Heart) Tumors, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ, Embryonal Tumors, Endometrial Cancer (Uterine Cancer), Ependymoma, Esophageal Cancer, Esthesioneuroblastoma (Head and Neck Cancer), Ewing Sarcoma (Bone Cancer), Extracranial Germ Cell Tumor, Extragonadal Germ Cell Tumor, Eye Cancer, Childhood Intraocular Melanoma, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST) (Soft Tissue Sarcoma), Childhood Gastrointestinal Stromal Tumors, Germ Cell Tumors, Childhood Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Hodgkin Lymphoma, Hypopharyngeal Cancer (Head and Neck Cancer), Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell and Small Cell), Childhood Lung Cancer, Lymphoma, Male Breast Cancer, Malignant Fibrous Histiocytoma of Bone and Osteosarcoma, Melanoma, Merkel Cell Carcinoma (Skin Cancer), Mesothelioma, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer, Osteosarcoma and Malignant Fibrous Histiocytoma of Bone, Ovarian Cancer, Pancreatic Cancer, Pancreatic Neuroendocrine Tumors (Islet Cell Tumors), Papillomatosis, Paraganglioma, Parathyroid Cancer, Penile Cancer, Pharyngeal Cancer (Head and Neck Cancer), Pheochromocytoma, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Childhood (Soft Tissue Sarcoma), Salivary Gland Cancer (Head and Neck Cancer), Sarcoma, Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Uterine Sarcoma, Sezary Syndrome, Lymphoma, Skin Cancer, Small Cell Lung Cancer, Small Intestine Cancer, Soft Tissue Sarcoma, Squamous Cell Carcinoma of the Skin, Squamous Neck Cancer, Stomach (Gastric) Cancer, T-Cell Lymphoma, Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter, Renal Cell Cancer, Urethral Cancer, Uterine Sarcoma, Vaginal Cancer, Vascular Tumors (Soft Tissue Sarcoma), Vulvar Cancer, Wilms Tumor and Other Childhood Kidney Tumors.

In some embodiments of the compositions and methods of the disclosure, a disease or disorder of the disclosure includes, but is not limited to, a proliferative disease or disorder. In some embodiments, the proliferative disease or disorder is a cancer. In some embodiments, the cancer involves the present of a gene fusion that produces a chimeric RNA with sequences derived from two genes due to a deletion or translocation of DNA. Gene fusions pairs include but are not limited to: MAN2A1 and FER, DNAJB1 and PRKACA, BCR-ABL1, TMPRSS2 and ERG, EWSR1 and FLI1, PML and RARA, EML4 and ALK, KIAA1549 and BRAF, CCDC6 and RET, SS18 and SSX1, RUNX1 and RUNX1T1, PAX3 and FOXO1, NCOA4 and RET, ETV6 and RUNX1, FUS and DDIT3, SS18 and SSX2, NPM1 and ALK, KMT2A and AFF1, TCF3 and PBX1, STIL and TAL1, COL1A1 and PDGFB, CRTC1 and MAML2, NAB2 and STAT6, EWSR1 and ATF1, ETV6 and NTRK3, EWSR1 and ERG, EWSR1 and WT1, DNAJB1 and PRKACA, PAX7 and FOXO1, FUS and CREB3L2, CBFA2T3 and GLIS2, PAX8 and PPARG, KMT2A and MLLT1, EWSR1 and NR4A3, KMT2A and MLLT3, ASPSCR1 and TFE3, HMGA2 and LPP, JAZF1 and SUZ12, KIF5B and RET, FUS and ERG, SLC45A3 and ERG, NUP214 and ABL1, SET and NUP214, CD74 and ROS1, ETV6 and ABL1, TPM3 and NTRK1, PRKAR1A and RET, EWSR1 and CREB1, KMT2A and AFDN, EWSR1 and DDIT3, CLTC and ALK, ETV6 and PDGFRB, TPM3 and ALK, KMT2A and MLLT10, TMPRSS2 and ETV1, BRD4 and NUTM1, NUP98 and KDM5A, RANBP2 and ALK, CTNNB1 and PLAG1, KMT2A and ELL, TAF15 and NR4A3, FGFR3 and TACC3, PCM1 and JAK2, YWHAE and NUTM2B, STRN and ALK, CRTC3 and MAML2, CDH11 and USP6, CDKN2D and WDFY2, CIC and DUX4, SLC34A2 and ROS1, ATIC and ALK, CD74 and NRG1, MYB and NFIB, PRCC and TFE3, KIF5B and ALK, TMPRSS2 and ETV4, KMT2A and SEPT9, EWSR1 and POU5F1, FGFR1 and PLAG1, MN1 and ETV6, TBL1XR1 and TP63, KMT2A and EPS15, SLC45A3 and ELK4, DHH and RHEBL1, HEY1 and NCOA2, EZR and ROS1, GOPC and ROS1, HMGA2 and WIF1, KMT2A and CREBBP, SS18 and SSX4B, FAM131B and BRAF, EWSR1 and FEV, EWSR1 and PBX1, TPM4 and ALK, SND1 and BRAF, ACTB and GLI1, KMT2A and KNL1, KMT2A and SEPT6, SDC4 and ROS1, TFG and ALK, HNRNPA2B1 and ETV1, PTPRK and RSPO3, JAZF1 and PHF1, HMGA2 and RAD51B, KMT2A and MLLT11, TPR and NTRK1, AKAP9 and BRAF, FUS and CREB3L1, ETV6 and JAK2, HMGA2 and NFIB, KMT2A and AFF3, CHCHD7 and PLAG1, VTI1A and TCF7L2, LIFR and PLAG1, EWSR1 and ETV1, SRGAP3 and RAF1, KMT2A and AFF4, MEAF6 and PHF1, PAX3 and NCOA1, HAS2 and PLAG1, EWSR1 and NFATC2, HIP1 and ALK, GOLGA5 and RET, BCR and JAK2, EWSR1 and ETV4, DCTN1 and ALK, MBTD1 and CXorf67, NDRG1 and ERG, CARS and ALK, SFPQ and TFE3, KMT2A and ARHGAP26, KMT2A and EP300, KMT2A and TET1, PAX5 and JAK2, PPFIBP1 and ALK, YWHAE and NUTM2A, LRIG3 and ROS1, TFG and NTRK1, TPM3 and ROS1, SLC45A3 and ETV1, ERC1 and RET, SEC16A and NOTCH1, KTN1 and RET, SEC31A and JAK2, TCEA1 and PLAG1, QKI and NTRK2, RNF130 and BRAF, EIF3E and RSPO2, EWSR1 and ZNF444, LMNA and NTRK1, PPFIBP1 and ROS1, PWWP2A and ROS1, EWSR1 and YY1, FUS and ATF1, PAX3 and NCOA2, ZC3H7B and BCOR, BRD3 and NUTM1, CANT1 and ETV4, CIC and FOXO4, COL1A1 and USP6, EWSR1 and ZNF384, KMT2A and ABI1, KMT2A and ACTN4, KMT2A and CEP170B, KMT2A and FOXO3, KMT2A and GAS7, KMT2A and MLLT6, KMT2A and SEPT2, KMT2A and SEPT5, MSN and ALK, VCL and ALK, EZR and ERBB4, RELCH and RET, SLC3A2 and NRG1, TRIM24 and BRAF, KLC1 and ALK, ARID1A and MAST2, GPBP1L1 and MAST2, NFIX and MAST1, NOTCH1 and GABBR2, TADA2A and MAST1, ZNF700 and MAST1, TRIM24 and RET, TRIM33 and RET, SSBP2 and JAK2, KMT2A and EEFSEC, CLCN6 and BRAF, GNAI1 and BRAF, MKRN1 and BRAF, NACC2 and NTRK2, FGFR1 and TACC1, TRIM27 and RET, HMGA2 and FHIT, HOOK3 and RET, PCM1 and RET, CEP89 and BRAF, CLIP1 and ROS1, ERC1 and ROS1, HLA and A and ROS1, LSM14A and BRAF, MYO5A and ROS1, SHTN1 and ROS1, TP53 and NTRK1, TPM3 and ROS1, ZCCHC8 and ROS1, FGFR3 and BAIAP2L1, KLK2 and ETV1, ACSL3 and ETV1, NUP107 and LGR5, HMGA2 and CCNB1IP1, HMGA2 and COX6C, GATM and BRAF, HACL1 and RAF1, HERPUD1 and BRAF, ZSCAN30 and BRAF, SLC45A3 and BRAF, HMGA2 and LHFPL6, COL1A2 and PLAG1, ESRP1 and RAF1, IRF2BP2 and CDX1, TFG and NR4A3, CLTC and TFE3, EWSR1 and MYB, NONO and TFE3, FCHSD1 and BRAF, HMGA2 and EBF1, ACBD6 and RRP15, AGPAT5 and MCPH1, AGTRAP and BRAF, ARFIPI and FHDC1, ATG4C and FBXO38, BBS9 and PKD1L1, CENPK and KMT2A, CNBP and USP6, DDX5 and ETV4, EIF3K and CYP39A1, EPC1 and PHF1, ERO1A and FERMT2, ETV6 and ITPR2, EWSR1 and NFATC1, EWSR1 and PATZ1, EWSR1 and SMARCA5, EWSR1 and SP3, FBXL18 and RNF216, FGFR1 and ZNF703, FN1 and ALK, FUS and FEV, GMDS and PDE8B, HMGA2 and ALDH2, IL6R and ATP8B2, INTS4 and GAB2, JPT1 and USHIG, KLK2 and ETV4, KMT2A and ABI2, KMT2A and ARHGEF12, KMT2A and BTBD18, KMT2A and CASP8AP2, KMT2A and CBL, KMT2A and CIP2A, KMT2A and CT45A2, KMT2A and DAB2IP, KMT2A and FOXO4, KMT2A and FRYL, KMT2A and GMPS, KMT2A and GPHN, KMT2A and LASP1, KMT2A and LPP, KMT2A and MAPRE1, KMT2A and MYOIF, KMT2A and NCKIPSD, KMT2A and NRIP3, KMT2A and PDS5A, KMT2A and PICALM, KMT2A and PRRC1, KMT2A and SARNP, KMT2A and SH3GL1, KMT2A and SORBS2, KMT2A and TOP3A, KMT2A and ZFYVE19, MBOAT2 and PRKCE, MIA2 and GEMIN2, NF1 and ASIC2, NFIA and EHF, NTN1 and ACLY, OMD and USP6, PLA2R1 and RBMS1, PLXND1 and TMCC1, RAF1 and DAZL, RBM14 and PACS1, RGS22 and SYCP1, SEC31A and ALK, SEPT8 and AFF4, SLC22A1 and CUTA, SLC26A6 and PRKAR2A, SLC45A3 and ETV5, SQSTM1 and ALK, SS18L1 and SSX1, SSH2 and SUZ12, SUSD1 and PTBP3, TCF12 and NR4A3, TECTA and TBCEL, THRAP3 and USP6, TMPRSS2 and ETV5, TPR and ALK, UBE2L3 and KRAS, WDCP and ALK, SS18 and USP6

In some embodiments of the methods of the disclosure, a subject of the disclosure has been diagnosed with the disease or disorder. In some embodiments, the subject of the disclosure presents at least one sign or symptom of the disease or disorder. In some embodiments, the subject has a biomarker predictive of a risk of developing the disease or disorder. In some embodiments, the biomarker is a genetic mutation.

In some embodiments of the methods of the disclosure, a subject of the disclosure is female. In some embodiments of the methods of the disclosure, a subject of the disclosure is male. In some embodiments, a subject of the disclosure has two XX or XY chromosomes. In some embodiments, a subject of the disclosure has two XX or XY chromosomes and a third chromosome, either an X or a Y.

In some embodiments of the methods of the disclosure, a subject of the disclosure is a neonate, an infant, a child, an adult, a senior adult, or an elderly adult. In some embodiments of the methods of the disclosure, a subject of the disclosure is at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days, or at least about 31 days old. In some embodiments of the methods of the disclosure, a subject of the disclosure is at least about 1 months, at least about 2 months, at least about 3 months, at least about 4 months, at least about 5 months, at least about 6 months, at least about 7 months, at least about 8 months, at least about 9 months, at least about 10 months, at least about 11 months, or at least about 12 months old. In some embodiments of the methods of the disclosure, a subject of the disclosure is at least about 1 years, at least about 2 years, at least about 3 years, at least about 4 years, at least about 5 years, at least about 6 years, at least about 7 years, at least about 8 years, at least about 9 years, at least about 10 years, at least about 15 years, at least about 20 years, at least about 25 years, at least about 30 years, at least about 35 years, at least about 40 years, at least about 45 years, at least about 50 years, at least about 55 years, at least about 60 years, at least about 65 years, at least about 70 years, at least about 75 years, at least about 80 years, at least about 85 years, at least about 90 years, at least about 95 years, at least about 100 or any number of years or partial years in between of age.

In some embodiments of the methods of the disclosure, a subject of the disclosure is a mammal. In some embodiments, a subject of the disclosure is a non-human mammal.

In some embodiments of the methods of the disclosure, a subject of the disclosure is a human.

In some embodiments of the methods of the disclosure, a therapeutically effective amount comprises a single dose of a composition of the disclosure. In some embodiments, a therapeutically effective amount comprises a therapeutically effective amount comprises at least one dose of a composition of the disclosure. In some embodiments, a therapeutically effective amount comprises a therapeutically effective amount comprises one or more dose(s) of a composition of the disclosure.

In some embodiments of the methods of the disclosure, a therapeutically effective amount eliminates a sign or symptom of the disease or disorder. In some embodiments, a therapeutically effective amount reduces a severity of a sign or symptom of the disease or disorder.

In some embodiments of the methods of the disclosure, a therapeutically effective amount eliminates the disease or disorder.

In some embodiments of the methods of the disclosure, a therapeutically effective amount prevents an onset of a disease or disorder. In some embodiments, a therapeutically effective amount delays the onset of a disease or disorder. In some embodiments, a therapeutically effective amount reduces the severity of a sign or symptom of the disease or disorder. In some embodiments, a therapeutically effective amount improves a prognosis for the subject.

In some embodiments of the methods of the disclosure, a composition of the disclosure is administered to the subject systemically. In some embodiments, the composition of the disclosure is administered to the subject by an intravenous route. In some embodiments, the composition of the disclosure is administered to the subject by an injection or an infusion.

In some embodiments of the methods of the disclosure, a composition of the disclosure is administered to the subject locally. In some embodiments, the composition of the disclosure is administered to the subject by an intraosseous, intraocular, intracerebrospinal or intraspinal route. In some embodiments, the composition of the disclosure is administered directly to the cerebral spinal fluid of the central nervous system. In some embodiments, the composition of the disclosure is administered directly to a tissue or fluid of the eye and does not have bioavailability outside of ocular structures. In some embodiments, the composition of the disclosure is administered to the subject by an injection or an infusion.

In some embodiments, the compositions comprising the RNA donor molecules disclosed herein are formulated as pharmaceutical compositions. Briefly, pharmaceutical compositions for use as disclosed herein may comprise a fusion protein(s) or a polynucleotide encoding the fusion protein(s), optionally comprised in an AAV, which is optionally also immune orthogonal, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the disclosure may be formulated for oral, intravenous, topical, enteral, intraocular, and/or parenteral administration. In certain embodiments, the compositions of the present disclosure are formulated for intravenous administration.

NUMBERED EMBODIMENTS

In certain aspects, disclosed herein are the following embodiments:

1. A composition comprising an RNA donor molecule, comprising: (a) one or more replacement domains that encode a therapeutic sequence operably linked to; (b) one or more intronic domains that promote RNA splicing of the replacement domain; (c) one or more antisense domains that promote binding to a target RNA molecule, and (d) an engineered small nuclear RNA domain that promotes trans-splicing of the RNA donor molecule.

2. A composition comprising an engineered small nuclear RNA molecule and an RNA donor molecule, comprising: (a) one or more replacement domains that encode a therapeutic sequence operably linked to; (b) one or more intronic domains that promote RNA splicing of the replacement domain; and (c) one or more antisense domains that promote binding to a target RNA molecule.

3. The composition of embodiment 2, wherein the engineered small RNA molecule contains a motif that is complementary to a sequence within the RNA donor molecule wherein the motif is one of the following sequences: 5'-CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGCTCGT-3' (SEQ ID NO: 9), 5'-AGAGCTCGTTGCGA-3' (SEQ ID NO: 10), and 5'-GAGCTCGTTG-3' (SEQ ID NO: 11).

4. The composition of embodiment 2, wherein the engineered small nuclear RNA molecule is composed of a sequence, starting the on the 5' end, that is complementary to a sequence in the RNA donor molecule and is followed by a sequence derived or isolated from a human U1 gene.

5. The composition of embodiment 2, wherein the engineered small nuclear RNA molecule is composed of a sequence, starting the on the 5' end, that is complementary to a sequence in the RNA donor molecule and is followed by a sequence derived or isolated from a human snRNA gene.

6. The composition of embodiment 2, wherein the engineered small nuclear RNA is composed of a sequence, starting the on the 5' end, that is synthetic or derived or isolated from a human U1 gene, followed by a sequence that is complementary to a sequence in the RNA donor molecule, and is followed by another sequence derived or isolated from a human snRNA gene.

7. The composition of embodiment 2, wherein the engineered small nuclear RNA is composed of a sequence, starting the on the 5' end, that is derived or isolated from a human U1 gene and is followed by a sequence that is complementary to a sequence in the RNA donor molecule.

8. The composition of embodiments 1-7, wherein the replacement domain is derived or isolated from a human gene selected from the group consisting of: GLB1 (GM1 gangliosidosis); GBA (Gaucher disease); GM2A (GM2 gangliosidosis); PCSK9, LDLR, APOB, APOE (Familial hypercholesterolemia); GAA (Pompe disease); MYOC, OPTN, TBK1, WDR36, CYPIB1 (Open Angle Glaucoma); IDS (Hunter syndrome or Mucopolysaccharidosis 2); IDUA (Hurler syndrome or Mucopolysaccharidosis 1); CLN3 (Batten disease); F9 (Hemophilia B); F8 (Hemophilia A), LAMP2 (Danon disease); GLA (Fabry disease); SLC2A1 (glucose transporter deficiency type 1); UBE3A (Angelman syndrome); MYOC, OPTN, TBK1, WDR36, CYPIB1 (Open Angle Glaucoma); IDUA (Hurler syndrome or Mucopolysaccharidosis 1); IDS (Hunter syndrome or Mucopolysaccharidosis 2); CLN3 (Batten disease); LMNA (Limb-girdle muscular dystrophy type 1B); DMD (Duchenne muscular dystrophy); DYSF (Limb-girdle muscular dystrophy type 2B); SGCB (Limb-girdle muscular dystrophy type 2E); SGCG (Limb-girdle muscular dystrophy type 2C); SGCA (Limb-girdle muscular dystrophy type 2D); SGCD (Limb-girdle muscular dystrophy type 2F); DUX4, D4Z4 (Facioscapulohumeral muscular dystrophy); USHA2A, RPGR, RP2, RHO, PRPF31, USH1F, PRPF3, PRPF6 (Retinitis pigmentosa).

9. The composition of embodiments 1-7, wherein the replacement domain is derived or isolated from an expression-enhancing sequence selected from the group consisting of: Woodchuck Hepatitis Virus (WHV) Post-transcriptional Regulatory Element (WPRE), triplex from MALAT1, the PRE of Hepatitis B virus (HPRE), and an iron response element.

10. The composition of any one of embodiments 1-9, wherein the antisense domain is complementary to sequences derived or isolated from a human gene selected from the group consisting of: TNFRSF13B (common variable immune deficiency), ADA, CECR1 (Adenosine deaminase deficiency), IL2RG (X-linked severe combined immunodeficiency), HBB (Beta-thassalemia), HBA1, HBA2 (alpha-thassalemia), U2AF1 (myelodysplastic syndrome), SOD1, TARDBP, FUS, MATR3, SOD1, C9ORF72 (Amyotrophic lateral sclerosis), MAPT, PGRN (Frontotemporal dementia with parkinsonism), CDH23, MYO7A, USH2A (Usher's syndrome), GALC (Krabbe disease), SMPD1, NPC1, NPC2 (Niemann Pick disease), PRNP (prion disease), SCN1A (Dravet syndrome), PINK 1, ATPGAP2 (early-onset Parkinson's disease), ATXN1, ATXN2, ATXN3, PLEKHG4, SPTBN2, CACNA1A, ATXN7, TTBK2, PPP2R2B, KCNC3, PRKCG, ITRP1, TBP, KCND1, FGF14 (spinocerebellar ataxias), SCN1A, SCN2A, CACNA1A, GRIN2B, GRIN2A, MECP2, FOXG1, SLC6A1, PRRT2, PTEN, KCNQ2, KCNQ3, STARD7, CLRN1 (genetic epilepsy disorders), ATM (Ataxia-telangiectasia), GLB1 (GM1 gangliosidosis), GBA (Gaucher disease), GM2A (GM2 gangliosidosis), UBE3A (Angelman syndrome), SLC2A1 (glucose transporter deficiency type 1), LAMP2 (Danon disease), GLA (Fabry disease), PKD1, PKD2 (Autosomal dominant polycystic kidney disease), GAA (Pompe disease), PCSK9, LDLR, APOB, APOE (Familial hypercholesterolemia), MYOC, OPTN, TBK1, WDR36, CYPIB1 (Open Angle Glaucoma), IDUA (Hurler syndrome or Mucopolysaccharidosis 1), IDS (Hunter syndrome or Mucopolysaccharidosis 2), CLN3 (Batten disease), DMD (Duchenne muscular dystrophy), LMNA (Limb-girdle muscular dystrophy type 1), DYSF (Limb-girdle muscular dystrophy type 2B), SGCA (Limb-girdle muscular dystrophy type 2D), SGCB (Limb-girdle muscular dystrophy type 2E), SGCG (Limb-girdle muscular dystrophy type 2C), SGCD (Limb-girdle muscular dystrophy type 2F), DUX4, D4Z4 (Facioscapulohumeral muscular dystrophy), F9 (Hemophilia B), F8 (Hemophilia A), USHA2A, RPGR, RP2, RHO, PRPF31, USH1F, PRPF3, PRPF6 (Retinitis pigmentosa), CFTR (cystic fibrosis), GJB2, GJB6, STRC, DFNA1, DFNA14 (autosomal dominant hearing impairment), POU3F3 (non-syndromic hearing loss)

11. The composition of any one of embodiments 1-10, wherein the RNA donor molecule comprises an untranslated region that alters the localization, processing, or transport of the RNA donor molecule and/or the esnRNA.

12. The composition of any one of embodiments 1-2, wherein the sequence comprising RNA donor molecule and/or esnRNA comprises a sequence that is bound by an RNA-binding protein that increases the trans-splicing efficiency.

13. The composition of any of one embodiments 1-12, wherein RNA donor molecule is RNA, DNA, a DNA/RNA hybrid, nucleic acid analog, a chemically-modified nucleic acid, or a chimera composed of two or more nucleic acids or nucleic acid analogs.

14. The composition of any of one embodiments 1-13, wherein the wherein the RNA donor molecule further comprises a heterologous promoter.

15. The composition of any of one embodiments 1-14, wherein the esnRNA further comprises a heterologous promoter.

16. The composition of any of one embodiments 15, wherein the promoter is isolated or derived from a promoter capable of driving expression of a transfer RNA (tRNA).

17. A composition comprising an engineered small nuclear RNA that promotes trans-splicing of a target RNA molecule and an RNA donor molecule.

18. A composition comprising an engineered small nuclear RNA that promotes trans-splicing of a target RNA molecule and an RNA donor molecule, the RNA donor molecule comprising: (a) one or more replacement domains that encode a therapeutic sequence operably linked to; (b) one or more intronic domains that promote RNA splicing of the replacement domain; and (c) one or more antisense domains that promote binding to a target RNA molecule.

19. A composition of embodiments 17-18, wherein the engineered small nuclear RNA molecule is isolated or derived from a human small nuclear RNA gene.

20. A composition of embodiment 19, wherein the engineered small nuclear RNA domain is synthetic and binds components of the spliceosome.

21. A composition of embodiments 17-20, wherein the human small nuclear RNA gene is chosen from a group consisting of: U1, U2, U4, U5, U6, U7, U11, and U12.

22. A composition of embodiment 17-21, wherein the engineered small nuclear RNA domain comprises sequences isolated or derived from a variant of the human U1 gene.

23. A composition of embodiment 17-22, wherein the engineered small nuclear RNA molecule is derived or isolated from a U1 small nuclear RNA gene or variant and contains an RNA motif that begins less than 16 nucleobases from the 5' end that is partially or perfectly complementary to the RNA donor molecule.

24. A composition of embodiments 17-23, wherein the engineered small nuclear RNA molecule contains an RNA motif that is partially or perfectly complementary to the RNA donor molecule.

25. A composition of embodiment 24, wherein the RNA motif is chosen from a group consisting of: 5'-CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3' (SEQ ID NO: 9), 5'-AGAGCTCGTTGCGA-3' (SEQ ID NO: 10), and 5'-GAGCTCGTTG-3' (SEQ ID NO: 11).

26. A composition of embodiment 17-25, wherein the RNA donor molecule contains an RNA motif that is at least 4 nucleotides long and is partially or perfectly complementary to a sequence in the RNA donor molecule.

27. A composition of embodiments 17-26, wherein the engineered small RNA molecule comprises sequences derived or isolated from a U1 small nuclear RNA gene or variant.

28. A composition of embodiments 17-27, wherein the engineered small RNA molecule comprises sequences derived or isolated from a U1 small nuclear RNA gene and a variant of the U1 small nuclear RNA gene.

29. The composition of embodiment 17-28, wherein the RNA donor molecule is further comprising an untranslated region that enhances translation 30. The composition of embodiment 29, wherein the translation-enhancing element comprises a sequence derived or isolated from the group consisting of: Woodchuck Hepatitis Virus (WHV) Posttranscriptional Regulatory Element (WPRE), triplex from MALAT1, the PRE of Hepatitis B virus (HPRE), and an iron response element 31. The composition of embodiment 17-30 further comprising an RNA-binding protein that strengthens the interaction among the RNA donor molecule and the target RNA molecule and increases trans-splicing efficiency 32. The composition of embodiments 17-31, wherein the RNA donor molecule and small nuclear RNA molecule is RNA, DNA, a DNA/RNA hybrid, a nucleic acid analog, a chemically-modified nucleic acid, or a chimera composed of two or more nucleic acids or nucleic acid analogs.

33. A composition comprising an RNA donor molecule, comprising: (a) one or more replacement domains that encode a therapeutic sequence operably linked to; (b) one or more intronic domains that promote RNA splicing of the replacement domain; and (c) one or more antisense domains that promote binding to a target RNA molecule; and (d) an engineered small nuclear RNA domain that promotes trans-splicing of the RNA donor molecule.

34. A composition of embodiment 33, wherein the engineered small nuclear RNA molecule is isolated or derived from a human small nuclear RNA gene.

35. A composition of embodiment 33 or 34, wherein the engineered small nuclear RNA domain is isolated or derived from a human small nuclear RNA gene.

36. A composition of embodiment 33-35, wherein the engineered small nuclear RNA domain is synthetic and binds components of the spliceosome.

37. A composition of embodiments 33-36, wherein the human small nuclear RNA gene is chosen from a group consisting of: U1, U2, U4, U5, U6, U7, U11, and U12.

38. A composition of embodiment 37, wherein the engineered small nuclear RNA domain comprises sequences isolated or derived from a variant of the human U1 gene.

39. A composition of embodiment 37, wherein the engineered small nuclear RNA domain comprises sequences derived from the human U1 small nuclear RNA gene and a variant of the U1 small nuclear RNA gene.

40. A composition of embodiment 39, wherein the engineered small nuclear RNA domain is located less than 200 bases away from a splice donor site in the RNA donor molecule.

41. A composition of embodiment 40, wherein the RNA motif is chosen from a group consisting of: 5'-CGAGCTCTCT-3' (SEQ ID NO: 1), 5'-AACGAGCTCT-3' (SEQ ID NO: 2), 5'-CGCAACGAGC-3' (SEQ ID NO: 3), 5'-TATCGCAACG-3' (SEQ ID NO: 4), 5'-AATAATATCG-3' (SEQ ID NO: 5), 5'-TAAGAGAGCT-3' (SEQ ID NO: 6), 5'-AAGAGAGCTC-3' (SEQ ID NO: 7), 5'-AGAGAGCTCGTTGC-3' (SEQ ID NO: 8), 5'-GAGAGCTCGT-3' (SEQ ID NO: 9), 5'-AGAGCTCGTTGCGA-3' (SEQ ID NO: 10), and 5'-GAGCTCGTTG-3' (SEQ ID NO: 11).
42. A composition of embodiment 33-41, wherein the RNA donor molecule contains an RNA motif that is at least 4 nucleotides long and is partially or perfectly complementary to a sequence in the RNA donor molecule.
43. A composition of embodiments 33-42, wherein the engineered small RNA molecule comprises sequences derived or isolated from a U1 small nuclear RNA gene or variant of the U1 small nuclear RNA gene.
44. A composition of embodiments 33-43, wherein the engineered small RNA molecule comprises sequences derived or isolated from a U1 small nuclear RNA gene and a variant of the U1 small nuclear RNA gene.
45. The composition of embodiment 44, wherein the RNA donor molecule is further comprising an untranslated region that enhances translation
46. The composition of embodiment 45, wherein the translation-enhancing element comprises a sequence derived or isolated from the group consisting of: Woodchuck Hepatitis Virus (WHV) Posttranscriptional Regulatory Element (WPRE), triplex from MALAT1, the PRE of Hepatitis B virus (HPRE), and an iron response element
47. The composition of embodiments 17-46 further comprising an RNA-binding protein that strengthens the interaction among the RNA donor molecule and the target RNA molecule and increases trans-splicing efficiency
48. The composition of embodiments 17-47, wherein the RNA donor molecule and small nuclear RNA molecule is RNA, DNA, a DNA/RNA hybrid, a nucleic acid analog, a chemically-modified nucleic acid, or a chimera composed of two or more nucleic acids or nucleic acid analogs.
49. The composition of embodiment 17-48, wherein the nucleic acid molecule further comprises a heterologous promoter.
50. A vector comprising the composition of embodiments 17-49.
51. The vector of embodiment 50, wherein the vector is selected from the group consisting of: adeno-associated virus, retrovirus, lentivirus, adenovirus, nanoparticle, micelle, liposome, lipoplex, polymersome, polyplex, and dendrimer.
52. A cell comprising the vector of embodiment 51.
53. A method for treating a disease comprising administering to a patient in need of a therapeutically effective amount of a treatment comprising an RNA donor molecule and engineered small nuclear RNA molecule according to embodiment 17 or embodiment 18.
54. A method for correcting a genetic defect in a subject comprising administering to said subject an RNA donor molecule and engineered small nuclear RNA molecule according to embodiments 17-49.
55. A method for treating a disease comprising administering to a patient in need of a therapeutically effective amount of a treatment comprising an RNA donor molecule according to embodiments 17-49.
56. A method for correcting a genetic defect in a subject comprising administering to said subject an RNA donor molecule according to embodiments 17-49.

Definitions

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the term "coupled" may refer to a weak or strong interaction between two or more atoms or molecules. The interaction may be directly or indirectly mediated by one or more molecules.

EXAMPLES

The following examples are included for illustrative purposes only and are not intended to limit the scope of the invention.

Example 1: Identification of the Engineered Small Nuclear RNA

Figure 6A:
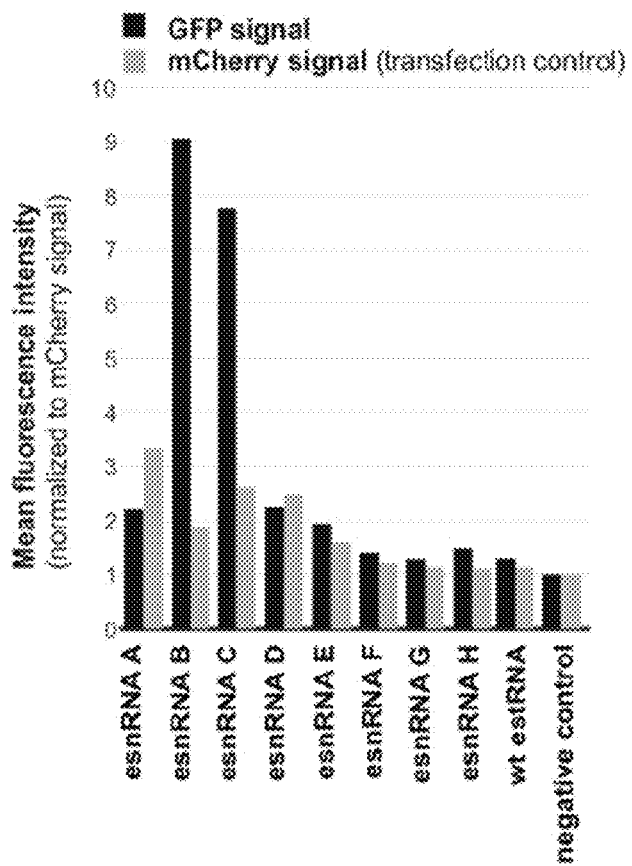
FIG. 6A is experimental data that that investigates the importance of specific features of the esnRNA in the context of replacement of specific sequences within a target RNA. Various esnRNAs (lettered A though H) were constructed that are derived from human U1 snRNA but carry mutations on the 5' end that generate a region that is complementary to the RNA donor molecule. The target of these antisense domains is outlined in FIG. 6B. Human cells were treated with the RNA donor and various esnRNAs along with a reporter system described in FIG. 5. The resulting GFP signal indicates that two esnRNAs ("esnRNA B" and "esnRNA C") yield the highest GFP signal and therefore the most efficient insertion of the RNA donor molecule into the target RNA. These data indicate that target site chose is an important factor to achieve efficient esnRNA-directed insertion of RNA donor sequences into the target RNA. "Negative control" refers to an experimental condition where the RNA donor contains no antisense domain that targets the reporter. "wt esnRNA" refers to an experimental condition where the RNA donor does indeed target the reporter but the esnRNA is identical to the unmodified, wildtype human U1 snRNA.
Figure 6B:
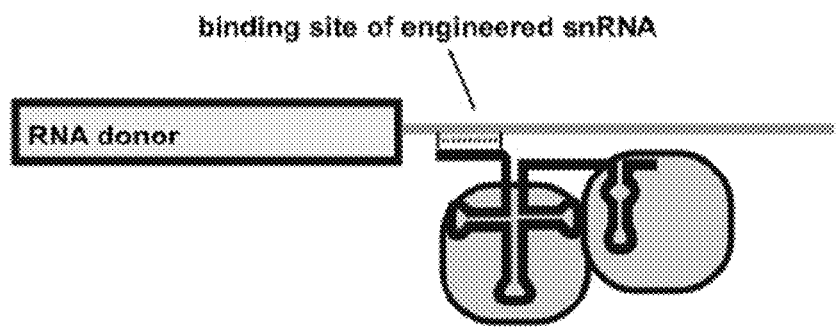

This study evaluates the activity of modified small nuclear RNAs in the context of RNA trans-splicing. First, it was assessed whether 8 engineered small nuclear RNAs could increase the efficiency of RNA-trans-splicing of an RNA donor molecule when they contain various sequences that are complementary to the RNA donor molecule (FIGS. 6A-6B). These variant RNA donor molecules target a split GFP reporter that fluoresces only after successful trans-splicing with the RNA donor molecule (FIGS. 4A-4D, 5A-5D). This assay is qualitative, not fully quantitative, but is useful because it is what end-users in cell biology often use when attempting to answer scientific questions about the presence, absence, or general magnitude of an RNA. GFP trans-splicing reporters has, accordingly, been widely used in the study of RNA trans-splicing technologies. A GFP reporter was used to compare the relative influence of different trans-splicing enhancer sequences on the efficiency of the trans-splicing reaction.

Experiments to collect data described in FIGS. 6A-6B were conducted with three transiently-transfected components: the reporter plasmid, the RNA donor (also encoded in a plasmid, driven by a CMV promoter), and the esnRNA (encoded in a plasmid and driven by the native U1 promoter). The esnRNAs are derived from human U1 snRNA and carry modified 5' ends that carry 10-14 base long regions that are perfectly complementary to various sequences within the RNA donor molecule. A human cell line HEK293T was maintained at 37 degrees C. in 5% CO2 and plated in a 24-well plate with 300,000 cells in each well. Cells were transfected with the above plasmids with Lipofectamine 3000 (Invitrogen) according to manufacturer's directions where $1/5^{th}$ of the total plasmid transfected was the reporter, $1/5^{th}$ was the RNA donor plasmid, $2/5^{th}$ was the esnRNA plasmid, and $1/5^{th}$ was a transfection control plasmid encoding CMV promoter driving expression of mCherry. The purpose of the mCherry control is to provide a means to normalize the signal generated by the GFP reporter. 48 hours after transfection, cells were harvested and subjected to fluorescence measurements using fluorescence-activated cell sorting with a Sony Spectral Analyzer. Cells that were positive for mCherry signal were identified and then the mean GFP and mCherry signal was assessed for this population. GFP signal was normalized to mCherry signal and the results were reported in FIG. 6A-6B. Most esnRNAs with varied complementary sequences do not generate appreciable increases in GFP signal compared to an unmodified U1 snRNA (wildtype or "wt" esnRNA). The full sequences of the esnRNAs used in FIG. 6A-6B are as follows, esnRNA A:
(SEQ ID NO: 71)
GCTCTCTTACgcaggggagataccatgatcacgaaggtgg
ttttcccagggcgaggcttatccattgcactccggatgtg
ctgacccctgcgatttccccaaatgtgggaaactcgactg
cataatttgtggtagtgggggactgcgttcgcgctttccc
ctgactttctggagtttcaaaagtagactgtacgctaagg
gtcatatctttttttgttttggtttgtgtcttggttggcg
tcttaaatgttaatcctacagtggagggctgcggaatagg
aagtaacatgtcgcctgcacgccataggagaaaaagcgag
catcagccgtatcggctttgtaacacaaattagctatcgt
gaagtccgctcag;

esnRNA B:
(SEQ ID NO: 72)
CGAGCTCTCTgcaggggagataccaTGATCAcgaaggtgg
ttttcccagggcgaggcttatccattgcactccggatgtg
ctgacccctgcgatttccccaaatgtgggaaactcgactg
cataatttgtggtagtgggggactgcgttcgcgctttccc
ctgactttctggagtttcaaaagtagactgtacgctaagg
gtcatatctttttttgttttggtttgtgtcttggttggcg
tcttaaatgttaatcctacagtggagggctgcggaatagg
aagtaacatgtcgcctgcacgccataggagaaaaagcgag
catcagccgtatcggctttgtaacacaaattagctatcgt
gaagtccgctcag;

esnRNA C:
(SEQ ID NO: 73)
AACGAGCTCTgcaggggagataccaTGATCAcgaaggtgg
ttttcccagggcgaggcttatccattgcactccggatgtg
ctgacccctgcgatttccccaaatgtgggaaactcgactg
cataatttgtggtagtgggggactgcgttcgcgctttccc
ctgactttctggagtttcaaaagtagactgtacgctaagg
gtcatatctttttttgttttggtttgtgtcttggttggcg
tcttaaatgttaatcctacagtggagggctgcggaatagg
aagtaacatgtcgcctgcacgccataggagaaaaagcgag
catcagccgtatcggctttgtaacacaaattagctatcgt
gaagtccgctcag;

esnRNA D:
(SEQ ID NO: 74)
CGCAACGAGCgcaggggagataccaTGATCAcgaaggtgg
ttttcccagggcgaggcttatccattgcactccggatgtg
ctgacccctgcgatttccccaaatgtgggaaactcgactg
cataatttgtggtagtgggggactgcgttcgcgctttccc
ctgactttctggagtttcaaaagtagactgtacgctaagg
gtcatatctttttttgttttggtttgtgtcttggttggcg
tcttaaatgttaatcctacagtggagggctgcggaatagg
aagtaacatgtcgcctgcacgccataggagaaaaagcgag
catcagccgtatcggctttgtaacacaaattagctatcgt
gaagtccgctcag;

esnRNA E:
(SEQ ID NO: 75)
TATCGCAACGgcaggggagataccaTGATCAcgaaggtgg
ttttcccagggcgaggcttatccattgcactccggatgtg
ctgacccctgcgatttccccaaatgtgggaaactcgactg
cataatttgtggtagtgggggactgcgttcgcgctttccc
ctgactttctggagtttcaaaagtagactgtacgctaagg
gtcatatctttttttgttttggtttgtgtcttggttggcg
tcttaaatgttaatcctacagtggagggctgcggaatagg
aagtaacatgtcgcctgcacgccataggagaaaaagcgag
catcagccgtatcggctttgtaacacaaattagctatcgt
gaagtccgctcag;

esnRNA F:
(SEQ ID NO: 76)
AATAATATCGgcaggggagataccaTGATCAcgaaggtgg
ttttcccagggcgaggcttatccattgcactccggatgtg
ctgacccctgcgatttccccaaatgtgggaaactcgactg
cataatttgtggtagtgggggactgcgttcgcgctttccc
ctgactttctggagtttcaaaagtagactgtacgctaagg
gtcatatctttttttgttttggtttgtgtcttggttggcg
tcttaaatgttaatcctacagtggagggctgcggaatagg
aagtaacatgtcgcctgcacgccataggagaaaaagcgag
catcagccgtatcggctttgtaacacaaattagctatcgt
gaagtccgctcag;

esnRNA G:
(SEQ ID NO: 77)
atCTCTCTTACCTCggggagataccaTGATCAcgaaggtg
gttttcccagggcgaggcttatccattgcactccggatgt
gctgacccctgcgatttccccaaatgtgggaaactcgact
gcataatttgtggtagtgggggactgcgttcgcgctttcc
cctgactttctggagtttcaaaagtagactgtacgctaag
ggtcatatctttttttgttttggtttgtgtcttggttggc -continued gtcttaaatgttaatcctacagtggagggctgcggaatag gaagtaacatgtcgcctgcacgccataggagaaaaagcga gcatcagccgtatcggctttgtaacacaaattagctatcg tgaagtccgctcag;

esnRNA H:

(SEQ ID NO: 78)
atAGCTCTCTTACCTCggagataccaTGATCAcgaaggtg gttttcccagggcgaggcttatccattgcactccggatgt gctgacccctgcgatttccccaaatgtgggaaactcgact gcataatttgtggtagtgggggactgcgttcgcgctttcc cctgactttctggagtttcaaaagtagactgtacgctaag ggtcatatctttttttgttttggtttgtgtcttggttggc gtcttaaatgttaatcctacagtggagggctgcggaatag gaagtaacatgtcgcctgcacgccataggagaaaaagcga gcatcagccgtatcggctttgtaacacaaattagctatcg tgaagtccgctcag.

Figure 6B:
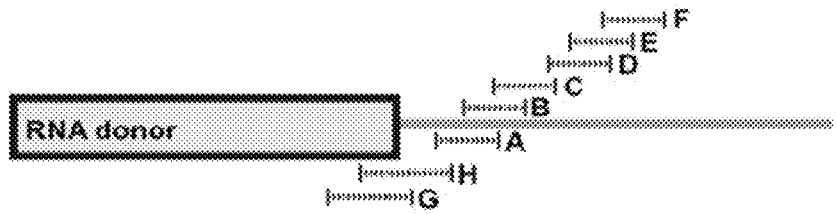

The reporter used in FIG. 6 contains (in the 5' to 3' direction) a CMV promoter, exon 81 of human COL17A1 gene, intron 81 of human COL17A1 gene, and the C-terminal portion of acGFP (127 amino acid residues). The sequence of this reporter is as follows:

(SEQ ID NO: 79)
CGTTACATAACTTACGGTAAATGGCCCGCCTGGCTGACCG

CCCAACGACCCCCGCCCATTGACGTCAATAATGACGTATG

TTCCCATAGTAACGCCAATAGGGACTTTCCATTGACGTCA

ATGGGTGGAGTATTTACGGTAAACTGCCCACTTGGCAGTA

CATCAAGTGTATCATATGCCAAGTACGCCCCCTATTGACG

TCAATGACGGTAAATGGCCCGCCTGGCATTATGCCCAGTA

CATGACCTTATGGGACTTTCCTACTTGGCAGTACATCTAC

GTATTAGTCATCGCTATTACCATGGTGATGCGGTTTTGGC

AGTACATCAATGGGCGTGGATAGCGGTTTGACTCACGGGG

ATTTCCAAGTCTCCACCCCATTGACGTCAATGGGAGTTTG

TTTTGGCACCAAAATCAACGGGACTTTCCAAAATGTCGTA

ACAACTCCGCCCCATTGACGCAAATGGGCGGTAGGCGTGT

ACGGTGGGAGGTCTATATAAGCAGAGCTCTCTGGCTAACT

AGAGAACCCACTGCTTACTGGCTTATCGAAATTAATACGA

CTCACTATAGGGAGACCCAAGCTGGCTAGCGTTTAAACTT

AAGCTTGGTACCGAGCTCGGATCCACTAGTCCAGTGTGGT

GGAATTCAAGCTTGGTGGTCATGGAGACCCTGGACCACCT

GGTGCCCCGgtgagtgaccagggaacactgcctggtgagg gtctggaagggctgggataggcattggccacagctgatga gccaggccttctctgtgttaatccctgagccctgttccct gcccttgaccctttctctGGATCCTTTTCCCTCCAGGTG -continued

AAGTTCGAGGGCGATACCCTGGTGAATCGCATCGAGCTGA

CCGGCACCGATTTCAAGGAGGATGGCAACATCCTGGGCAA

TAAGATGGAGTACAACTACAACGCCCACAATGTGTACATC

ATGACCGACAAGGCCAAGAATGGCATCAAGGTGAACTTCA

AGATCCGCCACAACATCGAGGATGGCAGCGTGCAGCTGGC

CGACCACTACCAGCAGAATACCCCCATCGGCGATGGCCCT

GTGCTGCTGCCCGATAACCACTACCTGTCCACCCAGAGCG

CCCTGTCCAAGGACCCCAACGAGAAGCGCGATCACATGAT

CTACTTCGGCTTCGTGACCGCCGCCGCCATCACCCACGGC

ATGGATGAGCTGTACAAGTGA.

Figure 7:
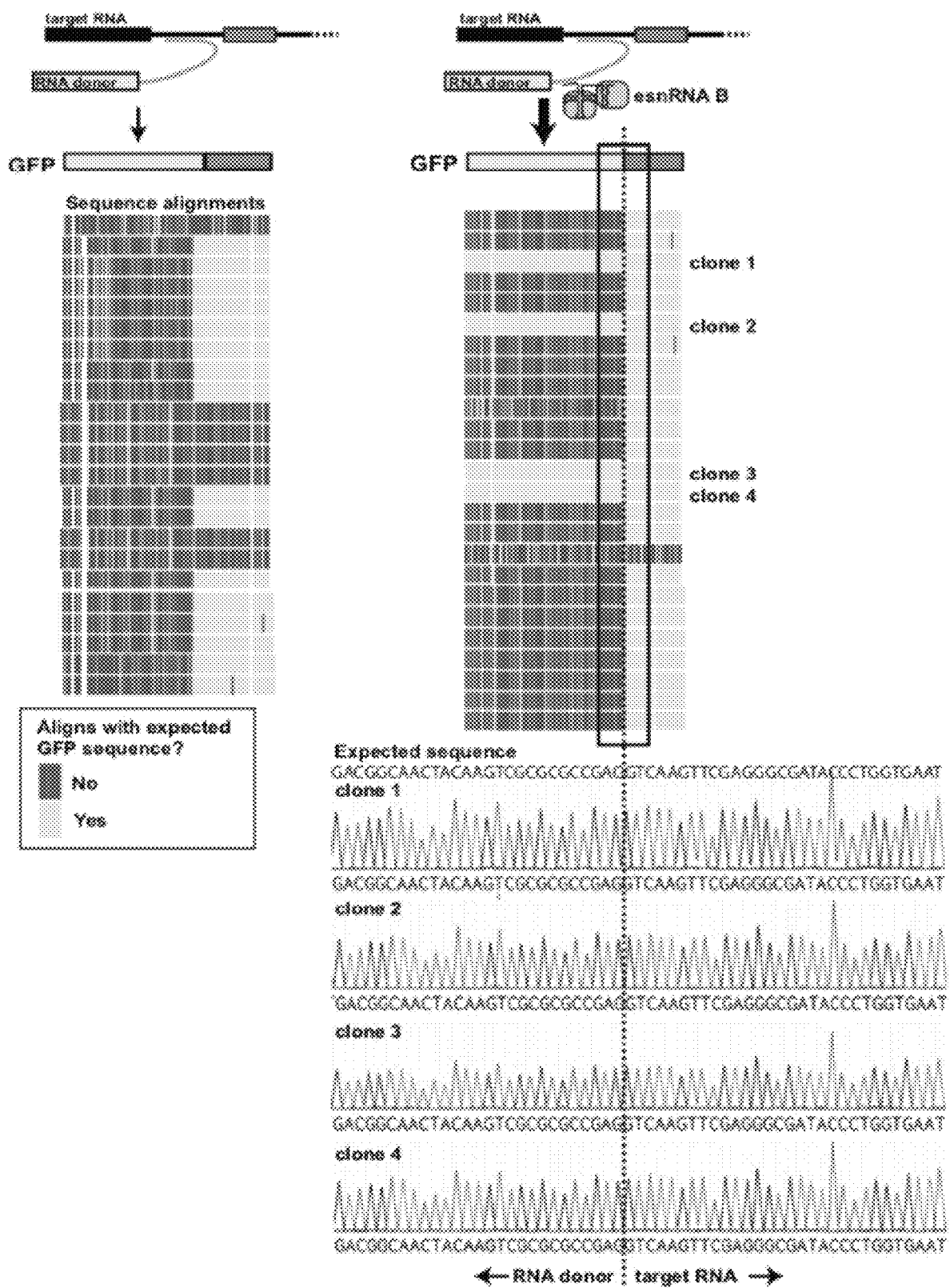
FIG. 7 contains experimental data that investigates the importance of the presence of the esnRNA in the context of replacement of specific sequences within a target RNA. In the absence of the esnRNA molecule, sequenced clones did not align to full length GFP (0 of 23 sequenced clones pictured in the right panel). In the presence of the esnRNA, four clones aligned to full length GFP (4 out of 24 sequenced clones pictured in the right panel). These fully-aligned clones are labeled "clone 1-4". The sequence of these clones flanking the junction of sequences derived from the RNA donor and from the target RNA reveals perfect alignment among all clones and the expected sequence of full length GFP. Figure discloses "GACGGCAACTA-CAAGTCGCGCGCCGAGGTCAAGTTCGAGGGCGA-TACCCTGGTGA AT" as SEQ ID NO: 89.

It was next assessed whether an esnRNA identified in FIGS. 6A-6B could promote high-fidelity RNA trans-splicing in the context of a different reporter system (FIG. 7). In FIG. 6A, the a reporter involving sequences from human COL17A1 gene was used while in FIG. 7, sequences from human SCN1A were used in the reporter. Therefore, successful trans-splicing among these two targets indicates that potential broad applicability of this method to address many targets. A similar assay was used involving a split GFP reporter that fluoresces only after successful trans-splicing of the RNA donor molecule (FIGS. 5A-5D).

Experiments to collect data described in FIG. 7 were conducted with three transiently-transfected components: the reporter plasmid, the RNA donor (also encoded in a plasmid, driven by a CMV promoter), and esnRNA B (encoded in a plasmid and driven by the native U1 promoter). A human cell line HEK293T was maintained at 37 degrees C. in 5% CO2 and plated in a 24-well plate with 300,000 cells in each well. Cells were transfected with the above plasmids with Lipofectamine 3000 (Invitrogen) according to manufacturer's directions where $1/5^{th}$ of the total plasmid transfected was the reporter, $1/5^{th}$ was the RNA donor plasmid, $2/5^{th}$ was the esnRNA plasmid, and $1/5^{th}$ was a transfection control plasmid encoding CMV promoter driving expression of mCherry. 48 hours after transfection, cells were harvested and RNA extracted from the cells using RNAeasy columns (Qiagen). Next, the cells were treated with DNAse (TurboDNAse, Thermo) and subjected to reverse transcription (Superscript III, Thermo). Next, the cDNA was amplified by PCR using primers that amplify both the cis-spliced and trans-spliced reporter products using the following primers: forward: TAATACGACTCAC-TATAGGGAGACCC (SEQ ID NO: 80) and reverse: CTC-CATCTTATTGCCCAGGA (SEQ ID NO: 81). These PCR products were cloned into the TOPO-TA vector (Thermo) and sequenced by the Sanger method. The sequencing results were aligned to full-length GFP (FIG. 7) and clones with perfect or near-perfect alignment were compared in FIG. 7. Full-length was only observed in the presence of the esnRNA where 4 of 25 clones yielded full length GFP (0 of 24 clones yielded full length GFP in the absence of the esnRNA). The reporter used in FIG. 7 contains (in the 5' to 3' direction) a CMV promoter, exon 15 of human SCN1A1 gene, intron 15 of human SCN1A gene, and the C-terminal portion of acGFP (127 amino acid residues). The sequence of this reporter is as follows:

(SEQ ID NO. 82)
GTGATGCGGTTTTGGCAGTACATCAATGGGCGTGGATAGC

GGTTTGACTCACGGGGATTTCCAAGTCTCCACCCCATTGA

CGTCAATGGGAGTTTGTTTTGGCACCAAAATCAACGGGAC

TTTCCAAAATGTCGTAACAACTCCGCCCCATTGACGCAAA

TGGGCGGTAGGCGTGTACGGTGGGAGGTCTATATAAGCAG

AGCTCTCTGGCTAACTAGAGAACCCACTGCTTACTGGCTT

ATCGAAATTAATACGACTCACTATAGGGAGACCCAAGCTG

GCTAGCGTTTAAACTTAAGCTTGGTACCGAGCTCGGATCC

ACTAGTCCAGTGTGGTGGAATTCAAGCTTCTCCGAGTGTT

CAAGTTGGCAAAGTCTTGGCCCACACTGAATATGCTCATT

AAGATCATTGGTAACTCGGTGGGAGCACTGGGCAACCTGA

CTCTGGTGTTGGCCATCATTGTCTTTATTTTTGCCGTGGT

TGGCATGCAGCTGTTTGGAAAAAGTTACAAAGATTGTGTC

TGCAAAATTGCCACTGACTGCAAACTCCCACGTTGGCACA

TGAACGACTTCTTCCACTCGTTCCTGATCGTGTTCCGCGT

GCTGTGTGGGGAGTGGATAGAGACCATGTGGGACTGCATG

GAGGTGGCAGGACAAGCTATGTGCCTTACTGTCTTCATGA

TGGTCATGGTGATTGGGAACCTTGTGtatgtacccaagt tagatatgcatttcagaaatacatcaataacataacaaat ttgtgcccaatttattaaaaaatgactttcatgataaata attttaaatgcctctgatcttaagatatgtttatcttctt attctaaaaatataccgcaacatggcaaagtatagtatca caatctactatggtaatatagaaatacatcttaaaacaaa tgtatgcacattaatattacctatgatattttactctcaa atccatattttacagctctattttttttaagacaaggtttc tttctgtatccctggctgtcctggaacttgctctgtagat ctagctgggcttgaactcagagatccacctgcctctccat cccaagtacttggattaaagtgattgtgccacctggcttc tcaactctattttattcagtcacttcattgcatttagtta ttaaattgcataggactgttaaaaatttacacaaatatgt tatgtgcgtgtgtttgtgtgtgatgtctatgtgtgcgtgt gcatgtgagggagaaaggggggcaattttttgctatagaata gtgctaacaagaatggtccatgcatatgttgaagactttc attctaaatttggtcatgactatgatttttttcagttatc atccaacaacacaaaatcatgaagagagaaaacccaaaat acatttaaataaataattgcaaatattaatcattttaaa tttggaattgttaaagtatctcagtaaatatatcttctttt tactcatataatattaaatataatgataaactaattcatt caagttcttcatttcatgtatgggagatcttgagagcagt agaaagaatgcctcatgtacatagagatggagcaatatca -continued caaattcagagtgctcaaaacttttctagggcggagtgtt gaacccagggcctcatgttttctggtcttggcccacttaa cttctagcaatgcctgtgctgtatcttgctcatatagcat tcggttattcattctatagctaaaggaataagccatccta tgtcctctgtgttgtggtgaacacatacttatgtctgttt tcaagGTcAAGTTCGAGGGCGATACCCTGGTGAATCGCAT

CGAGCTGACCGGCACCGATTTCAAGGAGGATGGCAACATC

CTGGGCAATAAGATGGAGTACAACTACAACGCCCACAATG

TGTACATCATGACCGACAAGGCCAAGAATGGCATCAAGGT

GAACTTCAAGATCCGCCACAACATCGAGGATGGCAGCGTG

CAGCTGGCCGACCACTACCAGCAGAATACCCCCATCGGCG

ATGGCCCTGTGCTGCTGCCCGATAACCACTACCTGTCCAC

CCAGAGCGCCCTGTCCAAGGACCCCAACGAGAAGCGCGAT

CACATGATCTACTTCGGCTTCGTGACCGCCGCCGCCATCA

CCCACGGCATGGATGAGCTGTACAAGTGA

It was next assessed whether specific features of the esnRNA are required for increased trans-splicing efficiency among the RNA donor and the target RNA. Starting with an esnRNA identified in FIG. 6 (esnRNA B), deleted or mutated various portions of the esnRNA that interact with specific spliceosomal components were deleted or mutated (FIG. 8B). Specifically, various stem-loop structures that interact with spliceosome components were either mutated to repetitive tracts of adenosine or deleted. These data reported in FIG. 8A indicate that recruitment of the spliceosome by the esnRNA is required for the observed enhancement of trans-splicing activity.

Figure 8A:
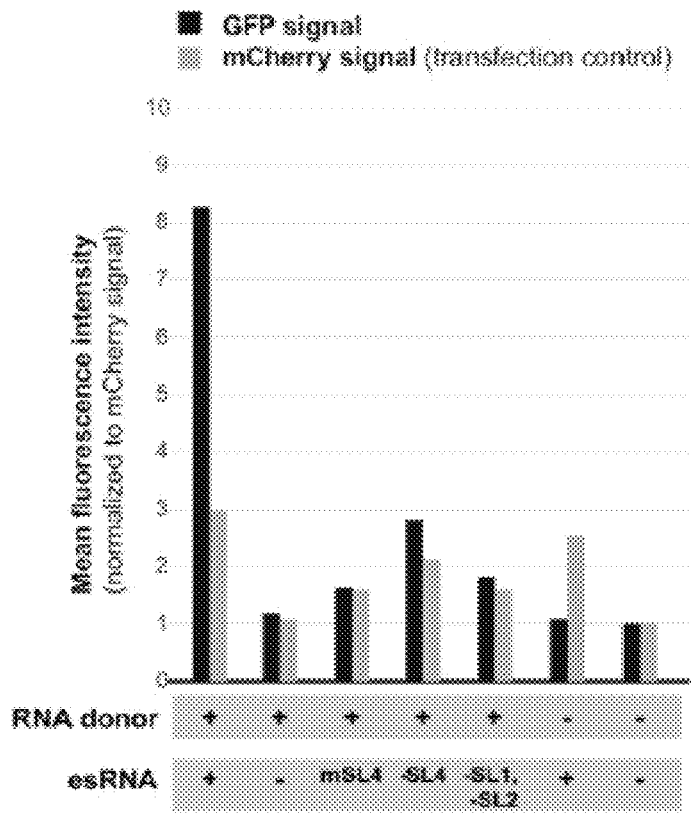
FIGS. 8A-8B contains experimental data that investigates the importance of various features of the esnRNA in the context of replacement of specific sequences within a target RNA. Cells were transfected with esnRNA B or various mutated versions of esnRNA B and the reporter system outlined in FIG. 5 (RNA donor and reporter). The resulting GFP signal indicates that the presence of stem-loop structures within the esnRNA is critical for the activity of the esnRNA. Indeed, removal or mutation of stem-loop structures that recruit spliceosome factors (stem-loop 1, stem-loop 2, or stem-loop 4) reduces the insertion of the RNA donor into the target RNA. Results are depicted in FIG. 8A. The different mutations are depicted in FIG. 8B.
Figure 8B:
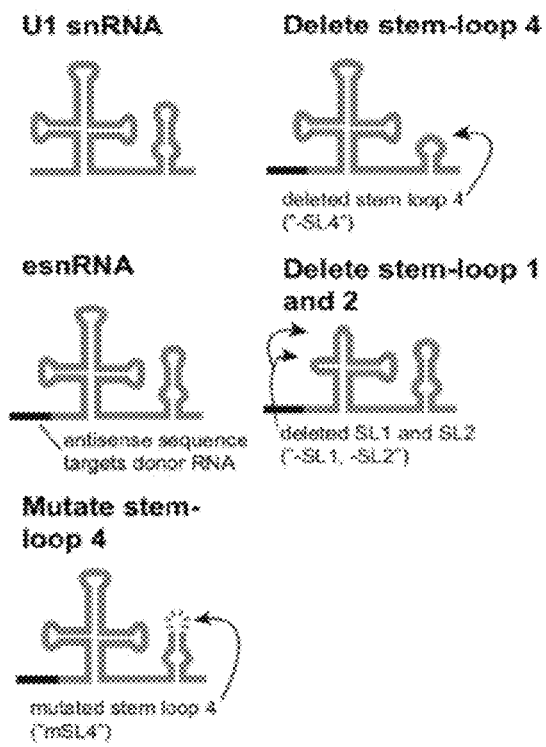

Experiments to collect data described in FIG. 8A were conducted with three transiently-transfected components: the reporter plasmid, the RNA donor (also encoded in a plasmid, driven by a CMV promoter), and esnRNA B (encoded in a plasmid and driven by the native U1 promoter). Variants of esnRNA B were compared that lack various features of wild type human U1 snRNA. A human cell line HEK293T was maintained at 37 degrees C. in 5% CO2 and plated in a 24-well plate with 300,000 cells in each well. Cells were transfected with the above plasmids with Lipofectamine 3000 (Invitrogen) according to manufacturer's directions where $1/5^{th}$ of the total plasmid transfected was the reporter, $1/5^{th}$ was the RNA donor plasmid, $2/5^{th}$ was the esnRNA plasmid, and $1/5^{th}$ was a transfection control plasmid encoding CMV promoter driving expression of mCherry. 48 hours after transfection, cells were harvested and subjected to fluorescence measurements using fluorescence-activated cell sorting with a Sony Spectral Analyzer. Cells that were positive for mCherry signal were identified and then the mean GFP and mCherry signal was assessed for this population. GFP signal was normalized to mCherry signal and the results were reported in FIG. 8. Deletion or mutation stem-loop 1, 2, or 4 resulted in dramatic reductions in GFP signal. This result indicates that recruitment of spliceosome components is the likely mechanism by which esnRNAs increase trans-splicing among the RNA donor and the target RNA. The full sequences of the esnRNAs used in FIGS. 8A-8B are as follow:

esnRNA B:

(SEQ ID NO: 72)
CGAGCTCTCTGcaggggagataccaTGATCAcgaaggggt tttcccagggcgaggcttatccattgcactccggatgtgc tgacccctgcgatttccccaaatgtgggaaactcgactgc ataatttgtggtagtgggggactgcgttcgcgctttcccc tgactttctggagtttcaaaagtagactgtacgctaaggg tcatatcttttttgttttggtttgtgtcttggttggcgt cttaaatgttaatcctacagtggagggctgcggaatagga agtaacatgtcgcctgcacgccataggagaaaaagcgagc atcagccgtatcggctttgtaacacaaattagctatcgtg aagtccgctcag;

esnRNA "mSL4":

(SEQ ID NO: 83)
CGAGCTCTCTGcaggggagataccaTGATCAcgaaggtgg ttttcccagggcgaggcttatccattgcactccggatgtg ctgaccoctgcgatttccccaaatgtgggaaactcgactg cataatttgtggtagtgggggactgcgttcgcgcttAAAA Atgactttctggagtttcaaaagtagactgtacgctaagg gtcatatcttttttgttttggtttgtgtcttggttggcg tcttaaatgttaatcctacagtggagggctgcggaatagg aagtaacatgtcgcctgcacgccataggagaaaaagcgag catcagccgtatcggctttgtaacacaaattagctatcgt gaagtccgctcag, esnRNA "-SL4":

(SEQ ID NO: 84)
CGAGCTCTCTGcaggggagataccaTGATCAcgaaggtgg ttttcccagggcgaggcttatccattgcactccggatgtg ctgaccoctgcgatttccccaaatgtgggaaactcgactg cataatttgtggtaactttctggagtttcaaaagtagact gtacgctaagggtcatatcttttttgttttggtttgtgt cttggttggcgtcttaaatgttaatcctacagtggagggc tgcggaataggaagtaacatgtcgcctgcacgccatagga gaaaaagcgagcatcagccgtatcggctttgtaacacaaa ttagctatcgtgaagtccgctcag, esnRNA "-SL1, -SL2":

(SEQ ID NO: 85)
CGAGCTCTCTGcaggggagataccaTggtggttttcccag ggcgaggcttatatgtgctgaccoctgcgatttccccaaa tgtgggaaactcgactgcataatttgtggtagtggggac tgcgttcgcgctttcccctgactttctggagtttcaaaag tagactgtacgctaagggtcatatcttttttgttttggt ttgtgtcttggttggcgtcttaaatgttaatcctacagtg gagggctgcggaataggaagtaacatgtcgcctgcacgcc ataggagaaaaagcgagcatcagccgtatcggctttgtaa cacaaattagctatcgtgaagtccgctcag.

The reporter used in FIG. 8A contains (in the 5' to 3' direction) a CMV promoter, exon 81 of human COL17A1 gene, intron 81 of human COL17A1 gene, and the C-terminal portion of acGFP (127 amino acid residues). The sequence is listed above.

Figure 9A:
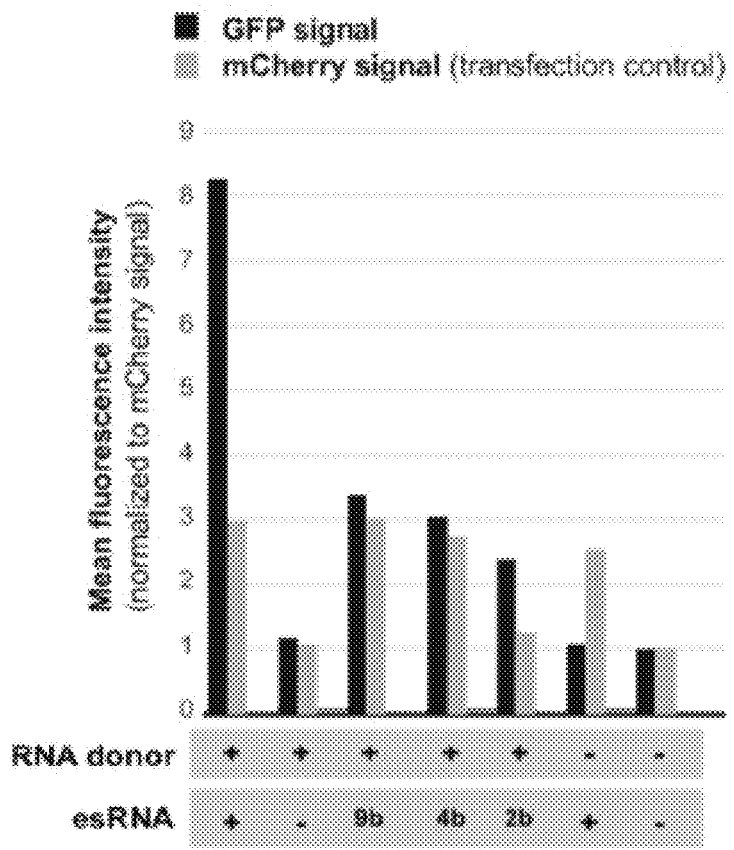
FIGS. 9A-9B contains experimental data that investigates the importance of the antisense domain within the esnRNA in the context of replacement of specific sequences within a target RNA. Cells were transfected with esnRNA B or various mutated versions of esnRNA B and the reporter system outlined in FIG. 5 (RNA donor and reporter). The resulting GFP signal (FIG. 9A) indicates that reducing the length of sequence in the esnRNA that is complementary to the RNA donor results in lower GFP signal and therefore less efficient insertion of the RNA donor in the target RNA. esnRNA "+" indicates the presence of an esnRNA that contains a 10-base complementary sequence to the RNA donor. "9b", "4b", and "2b" indicate 9-base, 4-base, and 2-base complementary sequences among the esnRNA and RNA donor, respectively (FIG. 9B). RNA donor "+" indicates the presence of an RNA donor that contains sequences that are complementary to the target RNA while "–" indicates a control RNA donor that is not complementary to the target RNA. Results are depicted in FIG. 9A. The different mutations are depicted in FIG. 9B.
Figure 9B:
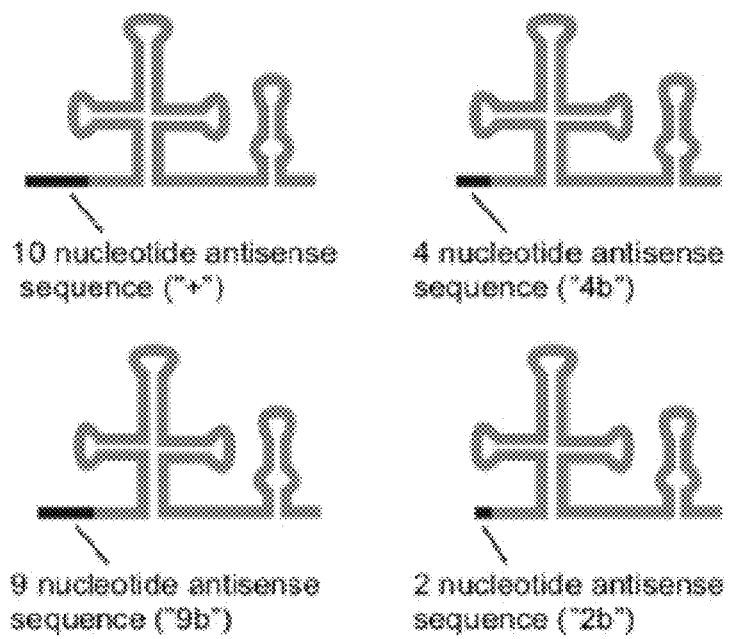

It was next assessed the degree of reverse complementarity among the esnRNA and RNA donor molecule required to induce efficient trans-splicing. While FIGS. 6A-8B indicate that recognition of the RNA donor by the esnRNA and recruitment of spliceosomal factors are required to induce efficient trans-splicing among the RNA donor and the target RNA, it was next investigated whether reducing the reverse complementarity of esnRNA B with an RNA donor molecule would also reduce trans-splicing efficiency. esnRNA B contains a 10 nucleotide sequence that is complementary to the reporter. Sequential mutations of esnRNA B were made that have 9 nucleotide, 4 nucleotide and 2 nucleotide sequences that that are complementary to the reporter (FIG. 9B). Indeed, reducing the degree of reverse complementarity concomitantly reduces the trans-splicing activity (FIG. 9A). This result indicates that association of the esnRNA molecule to the RNA donor molecule is required to increase trans-splicing activity.

Experiments to collect data described in FIG. 9A-9B were conducted with three transiently-transfected components: the reporter plasmid, the RNA donor (also encoded in a plasmid, driven by a CMV promoter), and esnRNA B or various mutants (encoded in a plasmid and driven by the native U1 promoter). A human cell line HEK293T was maintained at 37 degrees C. in 5% CO2 and plated in a 24-well plate with 300,000 cells in each well. Cells were transfected with the above plasmids with Lipofectamine 3000 (Invitrogen) according to manufacturer's directions where $1/5^{th}$ of the total plasmid transfected was the reporter, $1/5^{th}$ was the RNA donor plasmid, $2/5^{th}$ was the esnRNA plasmid, and $1/5^{th}$ was a transfection control plasmid encoding CMV promoter driving expression of mCherry. 48 hours after transfection, cells were harvested and subjected to fluorescence measurements using fluorescence-activated cell sorting with a Sony Spectral Analyzer. Cells that were positive for mCherry signal were identified and then the mean GFP and mCherry signal was assessed for this population. GFP signal was normalized to mCherry signal and the results were reported in FIG. 9A. The full sequences of the esnRNAs used in FIG. 9A are as follow (SEQ ID NO: 72)
CGAGCTCTCTGcaggggagataccaTGATCAcgaaggtgg ttttcccagggcgaggcttatccattgcactccggatgtg ctgaccoctgcgatttccccaaatgtgggaaactcgactg cataatttgtggtagtgggggactgcgttcgcgctttccc ctgactttctggagtttcaaaagtagactgtacgctaagg gtcatatcttttttgttttggtttgtgtcttggttggcg tcttaaatgttaatcctacagtggagggctgcggaatagg -continued
```
aagtaacatgtcgcctgcacgccataggagaaaaagcgag catcagccgtatcggctttgtaacacaaattagctatcgt gaagtccgctcag, esnRNA 9b:
                                    (SEQ ID NO: 86)
GAGCTCTCTgcaggggagataccaTGATCAcgaaggtggt tttcccagggcgaggcttatccattgcactccggatgtgc tgaccctgcgatttccccaaatgtgggaaactgactgc ataatttgtggtagtgggggactgcgttcgcgctttcccc tgactttctggagtttcaaaagtagactgtacgctaaggg tcatatctttttttgttttggtttgtgtcttggttggcgt cttaaatgttaatcctacagtggagggctgcggaatagga agtaacatgtcgcctgcacgccataggagaaaaagcgagc atcagccgtatcggctttgtaacacaaattagctatcgtg aagtccgctcag esnRNA 4b:
                                    (SEQ ID NO: 87)
aagaaaCTCTgcaggggagataccaTGATCAcgaaggtgg ttttcccagggcgaggcttatccattgcactccggatgtg ctgaccctgcgatttccccaaatgtgggaaactcgactg cataatttgtggtagtgggggactgcgttcgcgctttccc ctgactttctggagtttcaaaagtagactgtacgctaagg gtcatatctttttttgttttggtttgtgtcttggttggcg tcttaaatgttaatcctacagtggagggctgcggaatagg aagtaacatgtcgcctgcacgccataggagaaaaagcgag catcagccgtatcggctttgtaacacaaattagctatcgt gaagtccgctcag esnRNA 2b:
                                    (SEQ ID NO: 88)
aagaaaaaCTgcaggggagataccaTGATCAcgaaggtgg ttttcccagggcgaggcttatccattgcactccggatgtg ctgaccctgcgatttccccaaatgtgggaaactcgactg cataatttgtggtagtgggggactgcgttcgcgctttccc ctgactttctggagtttcaaaagtagactgtacgctaagg gtcatatctttttttgttttggtttgtgtcttggttggcg tcttaaatgttaatcctacagtggagggctgcggaatagg aagtaacatgtcgcctgcacgccataggagaaaaagcgag catcagccgtatcggctttgtaacacaaattagctatcgt gaagtccgctcag.
```

The reporter used in FIG. 9 contains (in the 5' to 3' direction) a CMV promoter, exon 81 of human COL17A1 gene, intron 81 of human COL17A1 gene, and the C-terminal portion of acGFP (127 amino acid residues). The sequence is listed above.

Example 2: Use of esnRNA and RNA Donor Molecule to Increase the Translation of Specific Target RNAs In addition to replacing specific mutated sequences within RNAs with non-mutated sequences, another useful operation on target mRNA molecules is increasing the protein produced by mRNAs. There have been many attempts to address this problem of insufficient protein production from specific mRNAs but each approach has major shortcomings. Indeed, small molecule drugs that increase translation by promoting stop codon read-through suffer extensive off-targets due to promotion of read through on non-target mRNAs. Further, pre-mature stop codons are only one of many causes of insufficient protein levels. Engineered tRNAs to block pre-mature termination codons suffer from this same fundamental issue (WO 2018/161032 A1). An RNA trans-splicing system, in contrast, could replace sequences in any target mRNA with translation-amplifying sequences to increase protein production. Efficient RNA trans-splicing mediated by intronic trans-splicing enhancing sequences (trans-splicing enhancer sequences) could address this long-felt but unmet need of a means to promote targeted amplification of protein production from specific mRNAs.

Myotonic dystrophy is caused by RNAs that carry repetitive 'CUG' tracts that bind the splicing factor MBNL1. Titration of MBNL1 away from its typical targets causes widespread dysfunction of RNA alternative splicing and is responsible for most manifestations of disease in patients. Increasing MBNL1 protein production with an efficient RNA trans-splicing approach could address this disease via production of sufficient MBNL1 protein to reconstitute its typical activities in alternative splicing regulation.

To assess the ability of an RNA trans-splicing systems containing trans-splicing enhancer sequences to increase protein production from specific mRNAs, an RNA trans-splicing system carrying various cis-splicing enhancer sequences and a Woodchuck Hepatitis Virus (WHV) post-transcriptional Regulatory Element (WPRE) was created. A reporter that contains a firefly luciferase coding sequence and the last 2 exons and intervening intron of MBNL1 was created.

Figure 10:
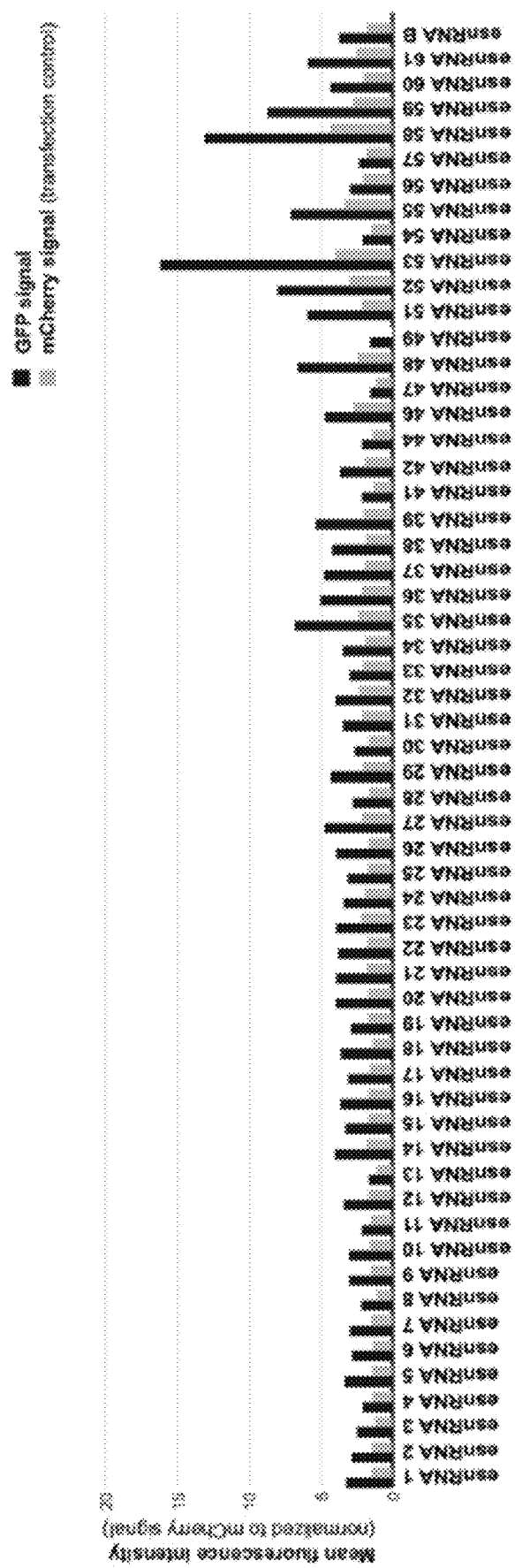
FIG. 10 contains experimental data that describes the activity of various esnRNAs in the context of replacement of specific sequences within a target RNA. Various esnRNAs (numbered 1-61 and compared to esnRNA B) were constructed that are derived from U1 snRNA and variants of U1 snRNA. All esnRNAs carry mutations on the 5' end that generate a region that is complementary to the RNA donor molecule. Human cells were treated with the RNA donor and various esnRNAs along with a reporter system described in FIG. 5. The resulting GFP signal indicates the efficiency associated with RNA editing. These data indicate that the use of sequences derived from the variants of the U1 snRNA is important means to increase RNA editing efficiency by trans-splicing.

Experiments were conducted with either transiently-transfected reporter, RNA donor, and esnRNA or systems packaged in lentivirus using the methods described in Example 1. Some translation-enhancing 3' sequences increased the amount of GFP reporter generated by the RNA donor and esnRNA combination. Results are depicted in FIG. 10.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of delivering an exonic sequence to a cell, comprising bringing the cell in contact with a composition comprising:
 (i) an engineered nucleic acid encoding an RNA trans-splicing nucleic acid comprising, in the 5' to 3' direction: the exonic sequence, an intronic domain, and an antisense domain, and
 (ii) a nucleic acid sequence encoding an engineered small nuclear RNA (esnRNA),
 wherein upon the composition coming in contact with the cell, the engineered nucleic acid and the nucleic acid sequence encoding the esnRNA enter the cell, and the RNA trans-splicing nucleic acid and the esnRNA are generated in the cell as separate molecules;
 wherein the esnRNA comprises an RNA motif at the 5' end of the esnRNA, and wherein the RNA motif is at least 10 nucleotides in length,
 wherein the intronic domain comprises an esnRNA-binding site that is complementary to the RNA motif,
 wherein the 5' end nucleotide of the esnRNA-binding site is between 4 and 30 nucleotides from the 3' end nucleotide of the exonic sequence in the RNA trans-splicing nucleic acid; and
 wherein the antisense domain in the RNA trans-splicing nucleic acid is complementary to a target RNA molecule in the cell,
 whereby the exonic sequence is trans-spliced to the target RNA molecule in the cell.

2. The method of claim 1, wherein the composition comprises a vector comprising the engineered nucleic acid encoding the RNA trans-splicing nucleic acid and the nucleic acid sequence encoding the esnRNA.

3. The method of claim 1, wherein the esnRNA is derived or isolated from a human small nuclear RNA gene selected from the group consisting of: U1, U2, U4, U5, U6, U7, U11, and U12.

4. The method of claim 1, wherein the nucleic acid sequence encoding the esnRNA comprises a sequence derived or isolated from a U1 small nuclear RNA gene or a variant thereof.

5. The method of claim 4, wherein the variant of the U1 small nuclear RNA gene is selected from the group consisting of: vU1.4, vU1.11, vU1.8, vU1.7, vU1.5, and vU1.12.

6. The method of claim 1, wherein the nucleic acid sequence encoding the esnRNA comprises RNA, DNA, a DNA/RNA hybrid, a nucleic acid analog, or a chemically-modified nucleic acid.

7. The method of claim 1, wherein the engineered nucleic acid encoding the RNA trans-splicing nucleic acid comprises RNA, DNA, a DNA/RNA hybrid, a nucleic acid analog, or a chemically-modified nucleic acid.

8. The method of claim 1, wherein the engineered nucleic acid encoding the RNA trans-splicing nucleic acid comprises deoxyribonucleic acid (DNA).

9. The method of claim 1, wherein the engineered nucleic acid further encodes a 5' untranslated region (5' UTR).

10. The method of claim 9, wherein the engineered nucleic acid further encodes a 3' untranslated region (3' UTR).

11. The method of claim 2, wherein the vector is selected from the group consisting of: adeno-associated virus, retrovirus, lentivirus, adenovirus, nanoparticle, micelle, liposome, lipoplex, polymersome, polyplex, and dendrimer.

12. The method of claim 1, wherein the exonic sequence is codon optimized for expression in a human cell.

13. The method of claim 1, wherein the antisense domain in the RNA trans-splicing nucleic acid is complementary to an intronic sequence in the target RNA molecule.

* * * * *